(12) United States Patent
Tamada et al.

(10) Patent No.: US 10,781,249 B2
(45) Date of Patent: *Sep. 22, 2020

(54) ANTI-GPC3 ANTIBODY

(71) Applicants: Yamaguchi University, Yamaguchi-shi, Yamaguchi (JP); National Cancer Center, Chuo-ku, Tokyo (JP); Noile-Immune Biotech, Inc., Minato-ku, Tokyo (JP)

(72) Inventors: Koji Tamada, Yamaguchi (JP); Yukimi Sakoda, Yamaguchi (JP); Tetsuya Nakatsura, Chiba (JP); Keigo Saito, Chiba (JP)

(73) Assignees: Yamaguchi University, Yamaguchi (JP); National Cancer Center, Tokyo (JP); Noile-Immune Biotech, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/546,787

(22) Filed: Aug. 21, 2019

(65) Prior Publication Data
US 2019/0367634 A1 Dec. 5, 2019

Related U.S. Application Data

(63) Continuation of application No. 16/472,356, filed as application No. PCT/JP2018/000257 on Jan. 10, 2018.

(30) Foreign Application Priority Data

Jan. 10, 2017 (JP) ................ 2017-001732

(51) Int. Cl.
| | | |
|---|---|---|
| *C07K 16/18* | (2006.01) | |
| *C12N 5/0783* | (2010.01) | |
| *G01N 33/68* | (2006.01) | |
| *C07K 14/54* | (2006.01) | |
| *C07K 14/725* | (2006.01) | |
| *C07K 16/30* | (2006.01) | |
| *C12N 5/078* | (2010.01) | |

(52) U.S. Cl.
CPC .......... *C07K 16/18* (2013.01); *C07K 14/5418* (2013.01); *C07K 14/7051* (2013.01); *C07K 16/303* (2013.01); *C12N 5/0634* (2013.01); *C12N 5/0636* (2013.01); *G01N 33/68* (2013.01); *C07K 2317/24* (2013.01); *C07K 2317/565* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 2006/0167232 A1 | 7/2006 | Aburatani et al. |
| 2007/0190599 A1 | 8/2007 | Nakano et al. |
| 2016/0215261 A1* | 7/2016 | Li ................... C12N 5/0638 |
| 2017/0010270 A1 | 1/2017 | Ohtomo et al. |
| 2017/0291953 A1 | 10/2017 | Tamada et al. |

FOREIGN PATENT DOCUMENTS

| | | |
|---|---|---|
| JP | 4011100 B2 | 9/2007 |
| JP | 2016-523518 A | 8/2016 |
| WO | WO 2004/022739 A1 | 3/2004 |
| WO | WO 2012/145469 A1 | 10/2012 |
| WO | WO 2013/070468 A1 | 5/2013 |
| WO | WO 2015/097928 A1 | 7/2015 |
| WO | WO-2015/179658 A2 | 11/2015 |
| WO | WO 2016/036973 A1 | 3/2016 |
| WO | WO 2016/049459 A1 | 3/2016 |
| WO | WO 2016/056228 A1 | 4/2016 |

OTHER PUBLICATIONS

Hippo et al., "Identification of Soluble $NH_2$-Terminal Fragment of Glypican-3 as a Serological Marker for Early-Stage Hepatocellular Carcinoma," Cancer Research, Apr. 1, 2004, 64:2418-2423.
Nakano et al., "Anti-glypican 3 antibodies cause ADCC against human hepatocellular carcinoma cells," Biochemical and Biophysical Research Communications, 2009, 378:279-284.
Nakatsura, Tetsuya, "Era of cancer immunotherapy has come," Jpn. J. Clin. Immunol., 2016, 39(2):164-171.
Li et al., "Redirecting T Cells to Glypican-3 with 4-1 BB Zeta Chimeric Antigen Receptors Results in Th1 Polarization and Potent Antitumor Activity," Human Gene Therapy, Aug. 16, 2016, 28(5):437-448.
Phung et al., "High-affinity monoclonal antibodies to cell surface tumor antigen glypican-3 generated through a combination of peptide immunization and flow cytometry screening," MABS, Sep. 1, 2012, 4(5):592-599.

* cited by examiner

*Primary Examiner* — Brad Duffy
(74) *Attorney, Agent, or Firm* — Foley & Lardner LLP

(57) ABSTRACT

An object of the present invention is to provide: an anti-GPC3 antibody that recognizes an epitope different from that for existing antibodies (e.g., GC33 and GC199) and can specifically bind, even in the form of single chain antibody, to GPC3 localized on a cell membrane; CAR comprising the anti-GPC3 single chain antibody; an immunocompetent cell expressing the CAR; a gene of the anti-GPC3 antibody or a gene of the CAR; a vector comprising the anti-GPC3 antibody gene or the CAR gene; a host cell in which the vector has been introduced; a method for specifically detecting GPC3; and a kit for specifically detecting GPC3. An antibody comprising particular heavy chain CDR1 to CDR3 and particular light chain CDR1 to CDR3 defined in claim 1, and specifically binding to a human-derived GPC3 polypeptide specifically binds to GPC3 localized on a cell membrane. CAR-immunocompetent cells prepared on the basis of CAR comprising such single chain antibody are useful for cancer immunotherapy.

8 Claims, 7 Drawing Sheets

Specification includes a Sequence Listing.

ANTI-GPC3 ANTIBODY

CROSS-REFERENCE TO RELATED APPLICATIONS

This application is a Continuation of U.S. application Ser. No. 16/472,356, which is the U.S. National Stage of PCT/JP2018/000257, filed Jan. 10, 2018, which claims priority to JP 2017-001732, filed Jan. 10, 2017.

The instant application contains a Sequence Listing which has been submitted in ASCII format via EFS-WEB and is hereby incorporated by reference in its entirety. Said ASCII copy, created on Aug. 14, 2019, is named sequence.txt and is 207903 bytes.

TECHNICAL FIELD

The present invention relates to: an antibody specifically binding to GPC3 (glypican-3) (anti-GPC3 antibody); a chimeric antigen receptor (hereinafter, also referred to as "CAR") comprising anti-GPC3 single chain antibody, a transmembrane region fused with a carboxyl (C) terminus of the anti-GPC3 single chain antibody, and an immunocompetent cell activation signal transduction region fused with a C terminus of the transmembrane region; an immunocompetent cell expressing the CAR; an anti-GPC3 antibody gene or a CAR gene; a vector comprising the anti-GPC3 antibody gene or the CAR gene; a host cell in which the vector has been introduced; a method for detecting GPC3; and a kit for detecting GPC3.

BACKGROUND ART

Glypican-3 (GPC3) is an extracellular matrix protein that is expressed in embryonic tissues, particularly, the liver or the kidney, and associated with organogenesis. The expression of GPC3 is not observed in human adult tissues except for placenta, but is observed in tissues of various cancers such as hepatocellular carcinoma, melanoma, ovarian clear cell adenocarcinoma, and lung squamous cell carcinoma. Thus, GPC3 is a protein that is expressed in embryonic tissues, as in proteins such as α-fetoprotein (AFP) and carcinoembryonic antigen (CEA), and is therefore classified into embryonal carcinoma antigens. Specifically, GPC3 is useful as a target molecule of cancer treatment, a tumor marker and a diagnostic marker, because its feature is that the protein is not expressed in normal tissue cells, but is specifically expressed in cancer cells.

GPC3 is a member of the proteoglycan family that functions as extracellular matrix in cell adhesion in organogenesis or as a receptor of a cell growth factor. A GPI (glycosylphosphatidylinositol) anchor is added to serine at position 560 located on the carboxyl (C)-terminal side of GPC3. The GPI anchor plays a role in localizing GPC3 on cell surface through covalent binding to cell membrane lipid. Also, serine at position 495 and serine at position 509 of GPC3 are modified with a heparan sulfate chain (HS chain). The HS chain is known to regulate a plurality of growth signal transduction pathways such as Wnt signal, FGF signal, and BMP signal transduction pathways. A growth signal transduction pathway involved is known to differ among the types of cancers. For example, in hepatocellular carcinoma (HCC), cells grow by the stimulation of the Wnt signal pathway. A common feature of the glypican family is the number of cysteine as abundant as 16 in an extracellular region, and these cysteine residues are considered to contribute to the stable formation of a conformation by forming a plurality of intramolecular disulfide bonds. The possibility has been reported that GPC3 on cell membrane surface is cleaved between arginine (R) at position 358 and serine (S) at position 359 (R358/S359) by furin convertase. However, since an amino (N)-terminal subunit of GPC3 is cross-linked through intramolecular disulfide bonds, GPC3, even when cleaved into two subunits, an N-terminal subunit and a C-terminal subunit, by furin convertase may probably retain its full-length structure without dissociating these subunits. The structure of soluble GPC3 remains a controversial subject. Thus, there are many unclear points as to the conformation of GPC3 localized on a cell membrane, also including the structures of isoforms of GPC3.

GPC3 on a cell membrane has a complicated structure. Therefore, for preparing an antibody against GPC3, it has been considered desirable that the simplest structural region is an epitope. A representative existing anti-GPC3 antibody includes a monoclonal antibody 1G12 which is distributed by BioMosaics, Inc. This antibody is an antibody obtained by immunizing Balb/c mice with an antigen (C-terminal 70-residue polypeptide of GPC3) designed so as to circumvent the complicated structure or localization of GPC3, to prepare hybridomas, and screening the hybridomas using the antigen. Antibodies GC33 and GC199 developed by a Japanese pharmaceutical manufacturer are also monoclonal antibodies established on the basis of the same concept as above and are antibodies obtained with the C-terminal partial fragment of GPC3 as an antigen (patent document 1).

PRIOR ART DOCUMENT

Patent Document

Patent document 1: Japanese Patent No. 4011100

SUMMARY OF THE INVENTION

Object to be Solved by the Invention

An object of the present invention is to provide: an anti-GPC3 antibody that recognizes an epitope different from that for existing antibodies (e.g., GC33 and GC199) and can specifically bind, even in the form of single chain antibody, to GPC3 localized on a cell membrane; CAR comprising the anti-GPC3 single chain antibody; an immunocompetent cell expressing the CAR; a gene of the anti-GPC3 antibody or a gene of the CAR; a vector comprising the anti-GPC3 antibody gene or the CAR gene; a host cell in which the vector has been introduced; a method for specifically detecting GPC3; and a kit for specifically detecting GPC3.

Means to Solve the Object

The present inventors are continuing diligent studies to attain the object. In the course of the studies, the present inventors have prepared a novel anti-GPC3 antibody by a phage display method which is an approach different from conventional monoclonal antibody preparation methods involving establishing hybridomas. Specifically, an immune library of antibody genes was synthesized using B cells derived from mice immunized with full-length human GPC3, and the genes were reconstituted into a single chain antibody (scFv) library, which was then incorporated into a phage display and expressed on phage surface, followed by biopanning using recombinant full-length human GPC3 and the GPC3-expressing cell line, and further, if necessary, a competitor C-terminal polypeptide of GPC3 serving as an epitope for the existing antibodies, to prepare an anti-GPC3 antibody. The prepared anti-GPC3 antibody has also been confirmed to be useful for cancer immunotherapy using T cells expressing a chimeric antigen receptor (CAR) (hereinafter, also referred to as "CAR-T cells"). The present invention has been completed on the basis of these findings.

Specifically, the present invention is as follows.

[1] An antibody specifically binding to a human GPC3 (glypican-3)-derived polypeptide consisting of the amino acid sequence represented by SEQ ID NO: 155 (hereinafter, also referred to as the "present antibody"), wherein the antibody (1-1) comprises a heavy chain complementarity determining region (CDR) 1 consisting of the amino acid sequence represented by SEQ ID NO: 1, a heavy chain CDR2 consisting of the amino acid sequence represented by SEQ ID NO: 2, and a heavy chain CDR3 consisting of the amino acid sequence represented by SEQ ID NO: 3, and a light chain CDR1 consisting of the amino acid sequence represented by SEQ ID NO: 4, a light chain CDR2 consisting of the amino acid sequence represented by SEQ ID NO: 5, and a light chain CDR3 consisting of the amino acid sequence represented by SEQ ID NO: 6; or (2-1) comprises a heavy chain CDR1 consisting of the amino acid sequence represented by SEQ ID NO: 11, a heavy chain CDR2 consisting of the amino acid sequence represented by SEQ ID NO: 12, and a heavy chain CDR3 consisting of the amino acid sequence represented by SEQ ID NO: 13, and a light chain CDR1 consisting of the amino acid sequence represented by SEQ ID NO: 14, a light chain CDR2 consisting of the amino acid sequence represented by SEQ ID NO: 15, and a light chain CDR3 consisting of the amino acid sequence represented by SEQ ID NO: 16; or (3-1) comprises a heavy chain CDR1 consisting of the amino acid sequence represented by SEQ ID NO: 21, a heavy chain CDR2 consisting of the amino acid sequence represented by SEQ ID NO: 22, and a heavy chain CDR3 consisting of the amino acid sequence represented by SEQ ID NO: 23, and a light chain CDR1 consisting of the amino acid sequence represented by SEQ ID NO: 24, a light chain CDR2 consisting of the amino acid sequence represented by SEQ ID NO: 25, and a light chain CDR3 consisting of the amino acid sequence represented by SEQ ID NO: 26; or (4-1) comprises a heavy chain CDR1 consisting of the amino acid sequence represented by SEQ ID NO: 31, a heavy chain CDR2 consisting of the amino acid sequence represented by SEQ ID NO: 32, and a heavy chain CDR3 consisting of the amino acid sequence represented by SEQ ID NO: 33, and a light chain CDR1 consisting of the amino acid sequence represented by SEQ ID NO: 34, a light chain CDR2 consisting of the amino acid sequence represented by SEQ ID NO: 35, and a light chain CDR3 consisting of the amino acid sequence represented by SEQ ID NO: 36; or (5-1) comprises a heavy chain CDR1 consisting of the amino acid sequence represented by SEQ ID NO: 41, a heavy chain CDR2 consisting of the amino acid sequence represented by SEQ ID NO: 42, and a heavy chain CDR3 consisting of the amino acid sequence represented by SEQ ID NO: 43, and a light chain CDR1 consisting of the amino acid sequence represented by SEQ ID NO: 44, a light chain CDR2 consisting of the amino acid sequence represented by SEQ ID NO: 45, and a light chain CDR3 consisting of the amino acid sequence represented by SEQ ID NO: 46; or (6-1) comprises a heavy chain CDR1 consisting of the amino acid sequence represented by SEQ ID NO: 51, a heavy chain CDR2 consisting of the amino acid sequence represented by SEQ ID NO: 52, and a heavy chain CDR3 consisting of the amino acid sequence represented by SEQ ID NO: 53, and a light chain CDR1 consisting of the amino acid sequence represented by SEQ ID NO: 54, a light chain CDR2 consisting of the amino acid sequence represented by SEQ ID NO: 55, and a light chain CDR3 consisting of the amino acid sequence represented by SEQ ID NO: 56; or (7-1) comprises a heavy chain CDR1 consisting of the amino acid sequence represented by SEQ ID NO: 61, a heavy chain CDR2 consisting of the amino acid sequence represented by SEQ ID NO: 62, and a heavy chain CDR3 consisting of the amino acid sequence represented by SEQ ID NO: 63, and a light chain CDR1 consisting of the amino acid sequence represented by SEQ ID NO: 64, a light chain CDR2 consisting of the amino acid sequence represented by SEQ ID NO: 65, and a light chain CDR3 consisting of the amino acid sequence represented by SEQ ID NO: 66; or (8-1) comprises heavy chain CDR1 consisting of the amino acid sequence represented by SEQ ID NO: 71, a heavy chain CDR2 consisting of the amino acid sequence represented by SEQ ID NO: 72, and a heavy chain CDR3 consisting of the amino acid sequence represented by SEQ ID NO: 73, and a light chain CDR1 consisting of the amino acid sequence represented by SEQ ID NO: 74, a light chain CDR2 consisting of the amino acid sequence represented by SEQ ID NO: 75, and a light chain CDR3 consisting of the amino acid sequence represented by SEQ ID NO: 76; or (9-1) comprises a heavy chain CDR1 consisting of the amino acid sequence represented by SEQ ID NO: 81, a heavy chain CDR2 consisting of the amino acid sequence represented by SEQ ID NO: 82, and a heavy chain CDR3 consisting of the amino acid sequence represented by SEQ ID NO: 83, and a light chain CDR1 consisting of the amino acid sequence represented by SEQ ID NO: 84, a light chain CDR2 consisting of the amino acid sequence represented by SEQ ID NO: 85, and a light chain CDR3 consisting of the amino acid sequence represented by SEQ ID NO: 86; or (10-1) comprises a heavy chain CDR1 consisting of the amino acid sequence represented by SEQ ID NO: 91, a heavy chain CDR2 consisting of the amino acid sequence represented by SEQ ID NO: 92, and a heavy chain CDR3 consisting of the amino acid sequence represented by SEQ ID NO: 93, and a light chain CDR1 consisting of the amino acid sequence represented by SEQ ID NO: 94, a light chain CDR2 consisting of the amino acid sequence represented by SEQ ID NO: 95, and a light chain CDR3 consisting of the amino acid sequence represented by SEQ ID NO: 96; or (11-1) comprises a heavy chain CDR1 consisting of the amino acid sequence represented by SEQ ID NO: 101, a heavy chain CDR2 consisting of the amino acid sequence represented by SEQ ID NO: 102, and a heavy chain CDR3 consisting of the amino acid sequence represented by SEQ ID NO: 103, and a light chain CDR1 consisting of the amino acid sequence represented by SEQ ID NO: 104, a light chain CDR2 consisting of the amino acid sequence represented by SEQ ID NO: 105, and a light chain CDR3 consisting of the amino acid sequence represented by SEQ ID NO: 106.

[2] The antibody according to [1], wherein the antibody (1-2) comprises a heavy chain variable region consisting of an amino acid sequence having at least 80% or higher sequence identity to the amino acid sequence represented by SEQ ID NO: 7, and a light chain variable region consisting of an amino acid sequence having at least 80% or higher sequence identity to the amino acid sequence represented by SEQ ID NO: 8; or (2-2) comprises a heavy chain variable region consisting of an amino acid sequence having at least 80% or higher sequence identity to the amino acid sequence represented by SEQ ID NO: 17, and a light chain variable region consisting of an amino acid sequence having at least 80% or higher sequence identity to the amino acid sequence represented by SEQ ID NO: 18; or (3-2) comprises a heavy chain variable region consisting of an amino acid sequence having at least 80% or higher sequence identity to the amino acid sequence represented by SEQ ID NO: 27, and a light chain variable region consisting of an amino acid sequence having at least 80% or higher sequence identity to the amino acid sequence represented by SEQ ID NO: 28; or (4-2) comprises a heavy chain variable region consisting of an amino acid sequence having at least 80% or higher sequence identity to the amino acid sequence represented by SEQ ID NO: 37, and a light chain variable region consisting of an amino acid sequence having at least 80% or higher sequence identity to the amino acid sequence represented by SEQ ID NO: 38; or (5-2) comprises a heavy chain variable region consisting of an amino acid sequence having at least 80% or higher sequence identity to the amino acid sequence represented by SEQ ID NO: 47, and a light chain variable region consisting of an amino acid sequence having at least 80% or higher sequence identity to the amino acid sequence represented by SEQ ID NO: 48; or (6-2) comprises a heavy chain variable region consisting of an amino acid sequence having at least 80% or higher sequence identity to the amino acid sequence represented by SEQ ID NO: 57, and a light chain variable region consisting of an amino acid sequence having at least 80% or higher sequence identity to the amino acid sequence represented by SEQ ID NO: 58; or (7-2) comprises a heavy chain variable region consisting of an amino acid sequence having at least 80% or higher sequence identity to the amino acid sequence represented by SEQ ID NO: 67, and a light chain variable region consisting of an amino acid sequence having at least 80% or higher sequence identity to the amino acid sequence represented by SEQ ID NO: 68; or (8-2) comprises a heavy chain variable region consisting of an amino acid sequence having at least 80% or higher sequence identity to the amino acid sequence represented by SEQ ID NO: 77, and a light chain variable region consisting of an amino acid sequence having at least 80% or higher sequence identity to the amino acid sequence represented by SEQ ID NO: 78; or (9-2) comprises a heavy chain variable region consisting of an amino acid sequence having at least 80% or higher sequence identity to the amino acid sequence represented by SEQ ID NO: 87, and a light chain variable region consisting of an amino acid sequence having at least 80% or higher sequence identity to the amino acid sequence represented by SEQ ID NO: 88; or (10-2) comprises a heavy chain variable region consisting of an amino acid sequence having at least 80% or higher sequence identity to the amino acid sequence represented by SEQ ID NO: 97, and a light chain variable region consisting of an amino acid sequence having at least 80% or higher sequence identity to the amino acid sequence represented by SEQ ID NO: 98; or (11-2) comprises a heavy chain variable region consisting of an amino acid sequence having at least 80% or higher sequence identity to the amino acid sequence represented by SEQ ID NO: 107, and a light chain variable region consisting of an amino acid sequence having at least 80% or higher sequence identity to the amino acid sequence represented by SEQ ID NO: 108.

[3] The antibody according to [1] or [2], wherein the antibody is single chain antibody.

[4] The antibody according to [3], wherein the single chain antibody (1-3) comprises an amino acid sequence having at least 80% or higher sequence identity to the amino acid sequence represented by SEQ ID NO: 165; or (2-3) comprises an amino acid sequence having at least 80% or higher sequence identity to the amino acid sequence represented by SEQ ID NO: 166; or (3-3) comprises an amino acid sequence having at least 80% or higher sequence identity to the amino acid sequence represented by SEQ ID NO: 167; or (4-3) comprises an amino acid sequence having at least 80% or higher sequence identity to the amino acid sequence represented by SEQ ID NO: 168; or (5-3) comprises an amino acid sequence having at least 80% or higher sequence identity to the amino acid sequence represented by SEQ ID NO: 169; or (6-3) comprises an amino acid sequence having at least 80% or higher sequence identity to the amino acid sequence represented by SEQ ID NO: 170; or (7-3) comprises an amino acid sequence having at least 80% or higher sequence identity to the amino acid sequence represented by SEQ ID NO: 171; or (8-3) comprises an amino acid sequence having at least 80% or higher sequence identity to the amino acid sequence represented by SEQ ID NO: 172; or (9-3) comprises an amino acid sequence having at least 80% or higher sequence identity to the amino acid sequence represented by SEQ ID NO: 173; or (10-3) comprises an amino acid sequence having at least 80% or higher sequence identity to the amino acid sequence represented by SEQ ID NO: 174; or (11-3) comprises an amino acid sequence having at least 80% or higher sequence identity to the amino acid sequence represented by SEQ ID NO: 175.

[5] The antibody according to [3], wherein the single chain antibody (1-3'-1) comprises an amino acid sequence having at least 80% or higher sequence identity to the amino acid sequence represented by SEQ ID NO: 178; or (1-3'-2) comprises an amino acid sequence having at least 80% or higher sequence identity to the amino acid sequence represented by SEQ ID NO: 179; or (1-3'-3) comprises an amino acid sequence having at least 80% or higher sequence identity to the amino acid sequence represented by SEQ ID NO: 180; or (2-3'-1) comprises an amino acid sequence having at least 80% or higher sequence identity to the amino acid sequence represented by SEQ ID NO: 181; or (2-3'-2) comprises an amino acid sequence having at least 80% or higher sequence identity to the amino acid sequence represented by SEQ ID NO: 182; or (2-3'-3) comprises an amino acid sequence having at least 80% or higher sequence identity to the amino acid sequence represented by SEQ ID NO: 183; or (2-3'-4) comprises an amino acid sequence having at least 80% or higher sequence identity to the amino acid sequence represented by SEQ ID NO: 184.

[6] The antibody according to [1] or [2], wherein the antibody (1-4) comprises a heavy chain consisting of an amino acid sequence having at least 80% or higher sequence identity to the amino acid sequence represented by SEQ ID NO: 9, and a light chain consisting of an amino acid sequence having at least 80% or higher sequence identity to the amino acid sequence represented by SEQ ID NO: 10; or (2-4) comprises a heavy chain consisting of an amino acid sequence having at least 80% or higher sequence identity to the amino acid sequence represented by SEQ ID NO: 19, and a light chain consisting of an amino acid sequence having at least 80% or higher sequence identity to the amino acid sequence represented by SEQ ID NO: 20; or (3-4) comprises a heavy chain consisting of an amino acid sequence having at least 80% or higher sequence identity to the amino acid sequence represented by SEQ ID NO: 29, and a light chain consisting of an amino acid sequence having at least 80% or higher sequence identity to the amino acid sequence represented by SEQ ID NO: 30; or (4-4) comprises a heavy chain consisting of an amino acid sequence having at least 80% or higher sequence identity to the amino acid sequence represented by SEQ ID NO: 39, and a light chain consisting of an amino acid sequence having at least 80% or higher sequence identity to the amino acid sequence represented by SEQ ID NO: 40; or (5-4) comprises a heavy chain consisting of an amino acid sequence having at least 80% or higher sequence identity to the amino acid sequence represented by SEQ ID NO: 49, and a light chain consisting of an amino acid sequence having at least 80% or higher sequence identity to the amino acid sequence represented by SEQ ID NO: 50; or (6-4) comprises a heavy chain consisting of an amino acid sequence having at least 80% or higher sequence identity to the amino acid sequence represented by SEQ ID NO: 59, and a light chain consisting of an amino acid sequence having at least 80% or higher sequence identity to the amino acid sequence represented by SEQ ID NO: 60; or (7-4) comprises a heavy chain consisting of an amino acid sequence having at least 80% or higher sequence identity to the amino acid sequence represented by SEQ ID NO: 69, and a light chain consisting of an amino acid sequence having at least 80% or higher sequence identity to the amino acid sequence represented by SEQ ID NO: 70; or (8-4) comprises a heavy chain consisting of an amino acid sequence having at least 80% or higher sequence identity to the amino acid sequence represented by SEQ ID NO: 79, and a light chain consisting of an amino acid sequence having at least 80% or higher sequence identity to the amino acid sequence represented by SEQ ID NO: 80; or (9-4) comprises a heavy chain consisting of an amino acid sequence having at least 80% or higher sequence identity to the amino acid sequence represented by SEQ ID NO: 89, and a light chain consisting of an amino acid sequence having at least 80% or higher sequence identity to the amino acid sequence represented by SEQ ID NO: 90; or (10-4) comprises a heavy chain consisting of an amino acid sequence having at least 80% or higher sequence identity to the amino acid sequence represented by SEQ ID NO: 99, and a light chain consisting of an amino acid sequence having at least 80% or higher sequence identity to the amino acid sequence represented by SEQ ID NO: 100; or (11-4) comprises a heavy chain consisting of an amino acid sequence having at least 80% or higher sequence identity to the amino acid sequence represented by SEQ ID NO: 109, and a light chain consisting of an amino acid sequence having at least 80% or higher sequence identity to the amino acid sequence represented by SEQ ID NO: 110.

[7] CAR comprising the antibody according to any one of [3] to [5] (hereinafter, also referred to as the "present single chain antibody"), a transmembrane region fused with a carboxyl terminus of the present single chain antibody, and an immunocompetent cell activation signal transduction region fused with a carboxyl terminus of the transmembrane region (hereinafter, also referred to as the "present CAR").

[8] The CAR according to [7], comprising the amino acid sequence represented by any of SEQ ID NOs: 185 to 187.

[9] An immunocompetent cell expressing the CAR according to [7] or [8] (hereinafter, also referred to as the "present immunocompetent cell").

[10] The immunocompetent cell according to [9], further expressing interleukin 7 (IL-7) and chemokine ligand 19 (CCL19).

[11] An antibody gene encoding the antibody according to any one of [1] to [6] (hereinafter, also referred to as the "present antibody gene"), or a CAR gene encoding the CAR according to [7] or [8] (hereinafter, also referred to as the "present CAR gene").

[12] An antibody gene encoding the antibody according to any one of [1] to [4] and [6].

[13] A vector comprising a promoter, and the antibody gene according to [11] or the CAR gene encoding the CAR according to [11] operably linked downstream of the promoter (hereinafter, also referred to as the "present vector").

[14] A vector comprising a promoter, and the antibody gene according to [12] operably linked downstream of the promoter.

[15] A host cell in which the vector according to [13] or [14] has been introduced (hereinafter, also referred to as the "present host cell").

[16] A method for detecting GPC3 (glypican-3), comprising the step of detecting GPC3 using the antibody according to any one of [1] to [6] (hereinafter, also referred to as the "present detection method").

[17] A kit for the detection of GPC3 (glypican-3), comprising the antibody according to any one of [1] to [6], or a labeled form thereof (hereinafter, also referred to as the "present kit for detection").

Examples of other embodiments of the present invention can include the present antibody for use in the detection of GPC3, and a method for producing the present antibody, comprising the steps of: immunizing nonhuman animals (e.g., mice and rats) with full-length human GPC3 consisting of the amino acid sequence represented by SEQ ID NO: 157; synthesizing cDNA by reverse transcription reaction from total RNA of B cells derived from the immunized nonhuman animals, and amplifying antibody genes to prepare an antibody gene library; and constructing a scFv phage library from the antibody gene library, and infecting *E. coli* with the library so that cells express scFv, followed by biopanning using the full-length human GPC3 and the GPC3-expressing cell line, and further, if necessary, a competitor C-terminal polypeptide of GPC3 (human-derived GPC3 polypeptide consisting of the amino acid sequence represented by SEQ ID NO: 156).

Effect of the Invention

The present antibody is an antibody specifically binding to GPC3 localized on a cell membrane not only in the form of IgG but in the form of scFv. CAR-T cells using the present antibody as scFv in CAR have excellent cytotoxic activity and the ability to produce IFN-γ. Hence, the present antibody is useful for cancer immunotherapy.

MODE OF CARRYING OUT THE INVENTION

Figure 1:
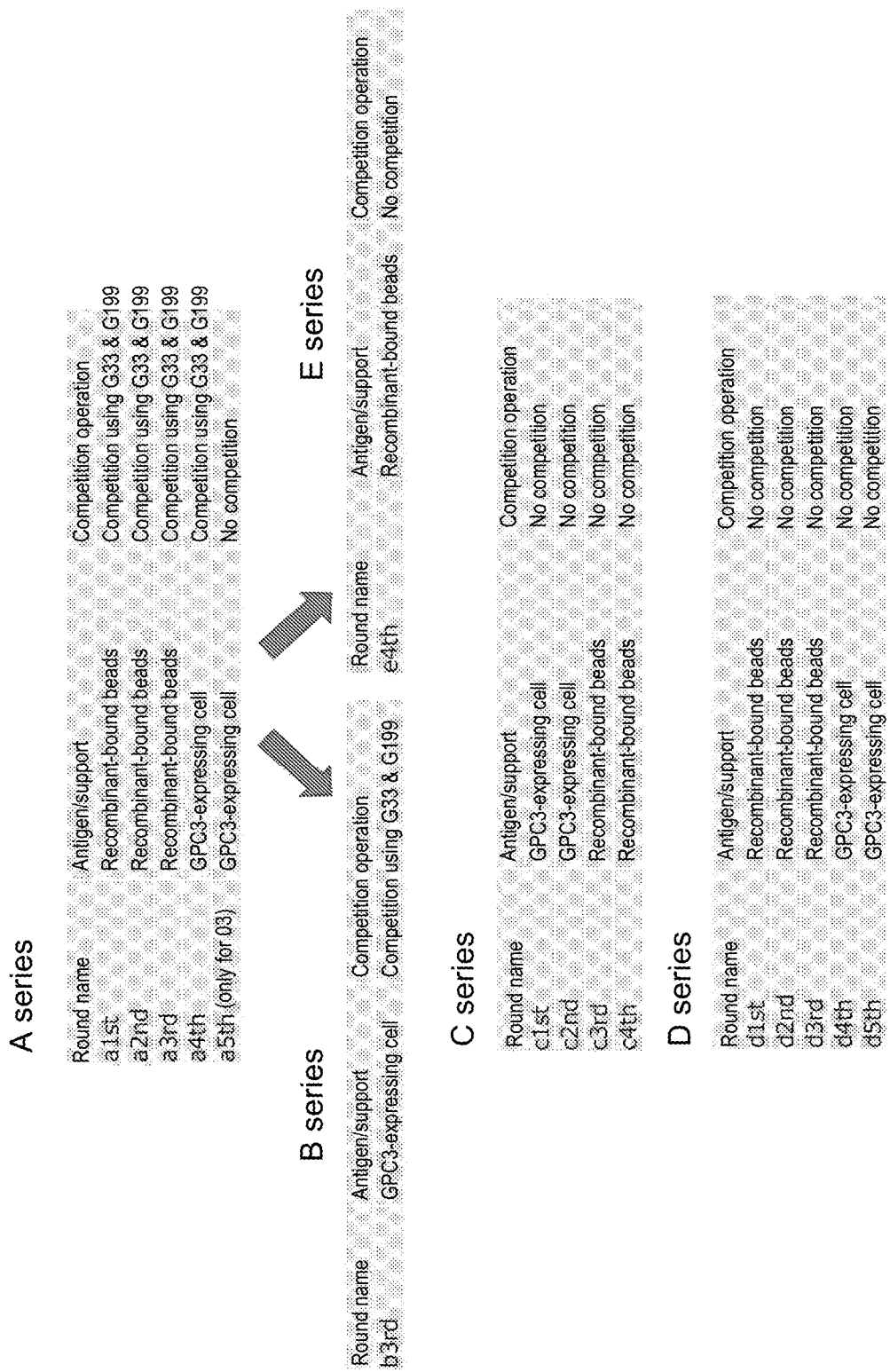
FIG. 1 is a diagram showing each round (step) of biopanning consisting of 5 types of series (A to E series). A series involves performing 3 rounds of biopanning with recombinant GPC3 immobilized on magnetic beads as a bait, and performing biopanning in rounds 4 and 5 with a GPC3-expressing cell line as a bait (round 5 was carried out only for 1413 #3). In rounds 1 to 4, existing anti-GPC3 antibodies (GC33 and GC199) were added as competitive antibodies. B series involves performing biopanning with GPC3-expressing cells as a bait in the presence of the competitive antibodies after round 2 of A series. E series involves performing biopanning with recombinant GPC3 immobilized on magnetic beads as a bait under conditions of no competitive antibody after round 3 of A series. In C series, 4 rounds in total of biopanning with a GPC3-expressing cell line as a bait in 2 rounds and recombinant GPC3 immobilized on magnetic beads as a bait in 2 rounds were performed in the absence of the competitive antibodies. D series involves performing the same biopanning as that of A series in the absence of the competitive antibodies.

The present antibody is an antibody comprising the heavy (H) chain and light (L) chain CDR1 to CDR3 described above in any of (1-1) to (11-1), and specifically binding to, as an epitope, at least a portion (usually within the range of 3 to 30 amino acid residues, preferably 4 to 20 amino acid residues, more preferably 5 to 15 amino acid residues) of a human-derived GPC3 polypeptide consisting of the amino acid sequence represented by SEQ ID NO: 155 (amino [N]-terminal polypeptide consisting of amino acid residues 32 to 471 [exons 1 to 7] of human-derived full-length GPC3 consisting of the amino acid sequence represented by SEQ ID NO: 157). This antibody specifically binds not only in the form of IgG but in the form of scFv to GPC3 localized on a cell membrane, and usually comprises a H chain variable region comprising the H chain CDR1 to CDR3 described above in any of (1-1) to (11-1), and a L chain variable region comprising the L chain CDR1 to CDR3 described above in any of (1-1) to (11-1). In this context, the phrase "specifically binding" means that the antibody recognizes and binds to the polypeptide consisting of the amino acid sequence represented by SEQ ID NO: 155 through a recognition mechanism with high antigen-antibody specificity. Thus, the present antibody does not specifically bind to a human-derived GPC3 polypeptide consisting of the amino acid sequence represented by SEQ ID NO: 156 (carboxyl [C]-terminal polypeptide consisting of amino acid residues 472 to 580 [exons 8 and 9] of human-derived full-length GPC3 consisting of the amino acid sequence represented by SEQ ID NO: 157).

The present antibody is not particularly limited by its origin, type, class, morphology, etc. The present antibody includes, for example: a human-derived antibody; an antibody derived from a nonhuman animal such as a mouse or a rat; a polyclonal antibody, an oligoclonal antibody (mixture of several to several tens of antibodies), and a monoclonal antibody; and a chimeric antibody or a humanized antibody in which a partial region (e.g., constant regions) of an antibody has been substituted by a region derived from a different organism species, an antibody fragment such as a F(ab')₂ antibody fragment obtained by digesting a monoclonal antibody with pepsin, a Fab' antibody fragment obtained by reducing a F(ab')₂ antibody fragment, and Fab obtained by digesting a monoclonal antibody with papain, and a recombinant antibody such as scFv containing an antibody heavy (H) chain variable region and an antibody light (H) chain variable region linked through amino acid cross-links. In the case of using the present antibody as CAR, scFv is preferred.

The present antibody is preferably in a separated form. In this context, the term "separated" means that the antibody is present in a state different from the state where the antibody is originally present in such a way that the antibody is taken out of an environment originally involving the antibody or expressed in an environment different from the environment originally involving the antibody by an artificial operation. Specifically, the "separated antibody" does not include an antibody that is derived from a certain individual and is in a state contained in the body of the individual without an external operation (artificial operation) or in a tissue or a body fluid (blood, plasma, serum, etc.) derived from the body. The present antibody is preferably an antibody prepared by an artificial operation (e.g., the recombinant antibody described above). Such an "antibody derived from a cell prepared by an artificial operation or an antibody produced from the cell" does not include an antibody that is not subjected to an artificial operation, for example, an antibody produced from a naturally occurring B cell.

In the present antibody, a framework region (FR) is usually linked to the N terminus and/or C terminus of each of H chain and L chain CDR1 to CDR3 regions. Among such FRs, examples of the H chain FRs can include H chain FR1 linked to the N terminus of H chain CDR1, H chain FR2 linked to the C terminus of H chain CDR1 (N terminus of H chain CDR2), H chain FR3 linked to the C terminus of H chain CDR2 (N terminus of H chain CDR3), and H chain FR4 linked to the C terminus of H chain CDR3. Among the FRs, examples of the L chain FRs can include L chain FR1 linked to the N terminus of L chain CDR1, L chain FR2 linked to the C terminus of L chain CDR1 (N terminus of L chain CDR2), L chain FR3 linked to the C terminus of L chain CDR2 (N terminus of L chain CDR3), and L chain FR4 linked to the C terminus of L chain CDR3.

Examples of the H chain FR1 can specifically include: (1-HFR1) a polypeptide consisting of amino acid residues 1 to 30 of the amino acid sequence represented by SEQ ID NO: 7, or a polypeptide consisting of an amino acid sequence having at least 80% or higher sequence identity to the amino acid sequence of the polypeptide; (2-HFR1) a polypeptide consisting of amino acid residues 1 to 30 of the amino acid sequence represented by SEQ ID NO: 17, or a polypeptide consisting of an amino acid sequence having at least 80% or higher sequence identity to the amino acid sequence of the polypeptide; (3-HFR1) a polypeptide consisting of amino acid residues 1 to 30 of the amino acid sequence represented by SEQ ID NO: 27, or a polypeptide consisting of an amino acid sequence having at least 80% or higher sequence identity to the amino acid sequence of the polypeptide; (4-HFR1) a polypeptide consisting of amino acid residues 1 to 30 of the amino acid sequence represented by SEQ ID NO: 37, or a polypeptide consisting of an amino acid sequence having at least 80% or higher sequence identity to the amino acid sequence of the polypeptide; (5-HFR1) a polypeptide consisting of amino acid residues 1 to 30 of the amino acid sequence represented by SEQ ID NO: 47, or a polypeptide consisting of an amino acid sequence having at least 80% or higher sequence identity to the amino acid sequence of the polypeptide; (6-HFR1) a polypeptide consisting of amino acid residues 1 to 30 of the amino acid sequence represented by SEQ ID NO: 57, or a polypeptide consisting of an amino acid sequence having at least 80% or higher sequence identity to the amino acid sequence of the polypeptide; (7-HFR1) a polypeptide consisting of amino acid residues 1 to 30 of the amino acid sequence represented by SEQ ID NO: 67, or a polypeptide consisting of an amino acid sequence having at least 80% or higher sequence identity to the amino acid sequence of the polypeptide; (8-HFR1) a polypeptide consisting of amino acid residues 1 to 30 of the amino acid sequence represented by SEQ ID NO: 77, or a polypeptide consisting of an amino acid sequence having at least 80% or higher sequence identity to the amino acid sequence of the polypeptide; (9-HFR1) a polypeptide consisting of amino acid residues 1 to 30 of the amino acid sequence represented by SEQ ID NO: 87, or a polypeptide consisting of an amino acid sequence having at least 80% or higher sequence identity to the amino acid sequence of the polypeptide; (10-HFR1) a polypeptide consisting of amino acid residues 1 to 30 of the amino acid sequence represented by SEQ ID NO: 97, or a polypeptide consisting of an amino acid sequence having at least 80% or higher sequence identity to the amino acid sequence of the polypeptide; and (11-HFR1) a polypeptide consisting of amino acid residues 1 to 30 of the amino acid sequence represented by SEQ ID NO: 107, or a polypeptide consisting of an amino acid sequence having at least 80% or higher sequence identity to the amino acid sequence of the polypeptide.

Examples of the H chain FR2 can specifically include: (1-HFR2) a polypeptide consisting of amino acid residues 36 to 49 of the amino acid sequence represented by SEQ ID NO: 7, or a polypeptide consisting of an amino acid sequence having at least 80% or higher sequence identity to the amino acid sequence of the polypeptide; (2-HFR2) a polypeptide consisting of amino acid residues 36 to 49 of the amino acid sequence represented by SEQ ID NO: 17, or a polypeptide consisting of an amino acid sequence having at least 80% or higher sequence identity to the amino acid sequence of the polypeptide; (3-HFR2) a polypeptide consisting of amino acid residues 36 to 49 of the amino acid sequence represented by SEQ ID NO: 27, or a polypeptide consisting of an amino acid sequence having at least 80% or higher sequence identity to the amino acid sequence of the polypeptide; (4-HFR2) a polypeptide consisting of amino acid residues 36 to 49 of the amino acid sequence represented by SEQ ID NO: 37, or a polypeptide consisting of an amino acid sequence having at least 80% or higher sequence identity to the amino acid sequence of the polypeptide; (5-HFR2) a polypeptide consisting of amino acid residues 36 to 49 of the amino acid sequence represented by SEQ ID NO: 47, or a polypeptide consisting of an amino acid sequence having at least 80% or higher sequence identity to the amino acid sequence of the polypeptide; (6-HFR2) a polypeptide consisting of amino acid residues 36 to 49 of the amino acid sequence represented by SEQ ID NO: 57, or a polypeptide consisting of an amino acid sequence having at least 80% or higher sequence identity to the amino acid sequence of the polypeptide; (7-HFR2) a polypeptide consisting of amino acid residues 36 to 49 of the amino acid sequence represented by SEQ ID NO: 67, or a polypeptide consisting of an amino acid sequence having at least 80% or higher sequence identity to the amino acid sequence of the polypeptide; (8-HFR2) a polypeptide consisting of amino acid residues 36 to 49 of the amino acid sequence represented by SEQ ID NO: 77, or a polypeptide consisting of an amino acid sequence having at least 80% or higher sequence identity to the amino acid sequence of the polypeptide; (9-HFR2) a polypeptide consisting of amino acid residues 36 to 49 of the amino acid sequence represented by SEQ ID NO: 87, or a polypeptide consisting of an amino acid sequence having at least 80% or higher sequence identity to the amino acid sequence of the polypeptide; (10-HFR2) a polypeptide consisting of amino acid residues 36 to 49 of the amino acid sequence represented by SEQ ID NO: 97, or a polypeptide consisting of an amino acid sequence having at least 80% or higher sequence identity to the amino acid sequence of the polypeptide; and (11-HFR2) a polypeptide consisting of amino acid residues 36 to 49 of the amino acid sequence represented by SEQ ID NO: 107, or a polypeptide consisting of an amino acid sequence having at least 80% or higher sequence identity to the amino acid sequence of the polypeptide.

Examples of the H chain FR3 can specifically include: (1-HFR3) a polypeptide consisting of amino acid residues 67 to 98 of the amino acid sequence represented by SEQ ID NO: 7, or a polypeptide consisting of an amino acid sequence having at least 80% or higher sequence identity to the amino acid sequence of the polypeptide; (2-HFR3) a polypeptide consisting of amino acid residues 67 to 98 of the amino acid sequence represented by SEQ ID NO: 17, or a polypeptide consisting of an amino acid sequence having at least 80% or higher sequence identity to the amino acid sequence of the polypeptide; (3-HFR3) a polypeptide consisting of amino acid residues 67 to 98 of the amino acid sequence represented by SEQ ID NO: 27, or a polypeptide consisting of an amino acid sequence having at least 80% or higher sequence identity to the amino acid sequence of the polypeptide; (4-HFR3) a polypeptide consisting of amino acid residues 67 to 99 of the amino acid sequence represented by SEQ ID NO: 37, or a polypeptide consisting of an amino acid sequence having at least 80% or higher sequence identity to the amino acid sequence of the polypeptide; (5-HFR3) a polypeptide consisting of amino acid residues 67 to 99 of the amino acid sequence represented by SEQ ID NO: 47, or a polypeptide consisting of an amino acid sequence having at least 80% or higher sequence identity to the amino acid sequence of the polypeptide; (6-HFR3) a polypeptide consisting of amino acid residues 67 to 98 of the amino acid sequence represented by SEQ ID NO: 57, or a polypeptide consisting of an amino acid sequence having at least 80% or higher sequence identity to the amino acid sequence of the polypeptide; (7-HFR3) a polypeptide consisting of amino acid residues 67 to 98 of the amino acid sequence represented by SEQ ID NO: 67, or a polypeptide consisting of an amino acid sequence having at least 80% or higher sequence identity to the amino acid sequence of the polypeptide; (8-HFR3) a polypeptide consisting of amino acid residues 67 to 98 of the amino acid sequence represented by SEQ ID NO: 77, or a polypeptide consisting of an amino acid sequence having at least 80% or higher sequence identity to the amino acid sequence of the polypeptide; (9-HFR3) a polypeptide consisting of amino acid residues 67 to 99 of the amino acid sequence represented by SEQ ID NO: 87, or a polypeptide consisting of an amino acid sequence having at least 80% or higher sequence identity to the amino acid sequence of the polypeptide; (10-HFR3) a polypeptide consisting of amino acid residues 67 to 98 of the amino acid sequence represented by SEQ ID NO: 97, or a polypeptide consisting of an amino acid sequence having at least 80% or higher sequence identity to the amino acid sequence of the polypeptide; and (11-HFR3) a polypeptide consisting of amino acid residues 67 to 98 of the amino acid sequence represented by SEQ ID NO: 107, or a polypeptide consisting of an amino acid sequence having at least 80% or higher sequence identity to the amino acid sequence of the polypeptide.

Examples of the H chain FR4 can specifically include: (1-HFR4) a polypeptide consisting of amino acid residues 109 to 118 of the amino acid sequence represented by SEQ ID NO: 7, or a polypeptide consisting of an amino acid sequence having at least 80% or higher sequence identity to the amino acid sequence of the polypeptide; (2-HFR4) a polypeptide consisting of amino acid residues 108 to 117 of the amino acid sequence represented by SEQ ID NO: 17, or a polypeptide consisting of an amino acid sequence having at least 80% or higher sequence identity to the amino acid sequence of the polypeptide; (3-HFR4) a polypeptide consisting of amino acid residues 106 to 115 of the amino acid sequence represented by SEQ ID NO: 27, or a polypeptide consisting of an amino acid sequence having at least 80% or higher sequence identity to the amino acid sequence of the polypeptide; (4-HFR4) a polypeptide consisting of amino acid residues 111 to 120 of the amino acid sequence represented by SEQ ID NO: 37, or a polypeptide consisting of an amino acid sequence having at least 80% or higher sequence identity to the amino acid sequence of the polypeptide; (5-HFR4) a polypeptide consisting of amino acid residues 108 to 117 of the amino acid sequence represented by SEQ ID NO: 47, or a polypeptide consisting of an amino acid sequence having at least 80% or higher sequence identity to the amino acid sequence of the polypeptide; (6-HFR4) a polypeptide consisting of amino acid residues 107 to 116 of the amino acid sequence represented by SEQ ID NO: 57, or a polypeptide consisting of an amino acid sequence having at least 80% or higher sequence identity to the amino acid sequence of the polypeptide; (7-HFR4) a polypeptide consisting of amino acid residues 106 to 115 of the amino acid sequence represented by SEQ ID NO: 67, or a polypeptide consisting of an amino acid sequence having at least 80% or higher sequence identity to the amino acid sequence of the polypeptide; (8-HFR4) a polypeptide consisting of amino acid residues 106 to 115 of the amino acid sequence represented by SEQ ID NO: 77, or a polypeptide consisting of an amino acid sequence having at least 80% or higher sequence identity to the amino acid sequence of the polypeptide; (9-HFR4) a polypeptide consisting of amino acid residues 111 to 120 of the amino acid sequence represented by SEQ ID NO: 87, or a polypeptide consisting of an amino acid sequence having at least 80% or higher sequence identity to the amino acid sequence of the polypeptide; (10-HFR4) a polypeptide consisting of amino acid residues 110 to 119 of the amino acid sequence represented by SEQ ID NO: 97, or a polypeptide consisting of an amino acid sequence having at least 80% or higher sequence identity to the amino acid sequence of the polypeptide; and (11-HFR4) a polypeptide consisting of amino acid residues 109 to 118 of the amino acid sequence represented by SEQ ID NO: 107, or a polypeptide consisting of an amino acid sequence having at least 80% or higher sequence identity to the amino acid sequence of the polypeptide.

Examples of the L chain FR1 can specifically include: (1-LFR1) a polypeptide consisting of amino acid residues 1 to 23 of the amino acid sequence represented by SEQ ID NO: 8, or a polypeptide consisting of an amino acid sequence having at least 80% or higher sequence identity to the amino acid sequence of the polypeptide; (2-LFR1) a polypeptide consisting of amino acid residues 1 to 23 of the amino acid sequence represented by SEQ ID NO: 18, or a polypeptide consisting of an amino acid sequence having at least 80% or higher sequence identity to the amino acid sequence of the polypeptide; (3-LFR1) a polypeptide consisting of amino acid residues 1 to 23 of the amino acid sequence represented by SEQ ID NO: 28, or a polypeptide consisting of an amino acid sequence having at least 80% or higher sequence identity to the amino acid sequence of the polypeptide; (4-LFR1) a polypeptide consisting of amino acid residues 1 to 23 of the amino acid sequence represented by SEQ ID NO: 38, or a polypeptide consisting of an amino acid sequence having at least 80% or higher sequence identity to the amino acid sequence of the polypeptide; (5-LFR1) a polypeptide consisting of amino acid residues 1 to 23 of the amino acid sequence represented by SEQ ID NO: 48, or a polypeptide consisting of an amino acid sequence having at least 80% or higher sequence identity to the amino acid sequence of the polypeptide; (6-LFR1) a polypeptide consisting of amino acid residues 1 to 23 of the amino acid sequence represented by SEQ ID NO: 58, or a polypeptide consisting of an amino acid sequence having at least 80% or higher sequence identity to the amino acid sequence of the polypeptide; (7-LFR1) a polypeptide consisting of amino acid residues 1 to 23 of the amino acid sequence represented by SEQ ID NO: 68, or a polypeptide consisting of an amino acid sequence having at least 80% or higher sequence identity to the amino acid sequence of the polypeptide; (8-LFR1) a polypeptide consisting of amino acid residues 1 to 23 of the amino acid sequence represented by SEQ ID NO: 78, or a polypeptide consisting of an amino acid sequence having at least 80% or higher sequence identity to the amino acid sequence of the polypeptide; (9-LFR1) a polypeptide consisting of amino acid residues 1 to 23 of the amino acid sequence represented by SEQ ID NO: 88, or a polypeptide consisting of an amino acid sequence having at least 80% or higher sequence identity to the amino acid sequence of the polypeptide; (10-LFR1) a polypeptide consisting of amino acid residues 1 to 23 of the amino acid sequence represented by SEQ ID NO: 98, or a polypeptide consisting of an amino acid sequence having at least 80% or higher sequence identity to the amino acid sequence of the polypeptide; and (11-LFR1) a polypeptide consisting of amino acid residues 1 to 23 of the amino acid sequence represented by SEQ ID NO: 108, or a polypeptide consisting of an amino acid sequence having at least 80% or higher sequence identity to the amino acid sequence of the polypeptide.

Examples of the L chain FR2 can specifically include: (1-LFR2) a polypeptide consisting of amino acid residues 35 to 49 of the amino acid sequence represented by SEQ ID NO: 8, or a polypeptide consisting of an amino acid sequence having at least 80% or higher sequence identity to the amino acid sequence of the polypeptide; (2-LFR2) a polypeptide consisting of amino acid residues 40 to 54 of the amino acid sequence represented by SEQ ID NO: 18, or a polypeptide consisting of an amino acid sequence having at least 80% or higher sequence identity to the amino acid sequence of the polypeptide; (3-LFR2) a polypeptide consisting of amino acid residues 35 to 49 of the amino acid sequence represented by SEQ ID NO: 28, or a polypeptide consisting of an amino acid sequence having at least 80% or higher sequence identity to the amino acid sequence of the polypeptide; (4-LFR2) a polypeptide consisting of amino acid residues 35 to 49 of the amino acid sequence represented by SEQ ID NO: 38, or a polypeptide consisting of an amino acid sequence having at least 80% or higher sequence identity to the amino acid sequence of the polypeptide; (5-LFR2) a polypeptide consisting of amino acid residues 41 to 55 of the amino acid sequence represented by SEQ ID NO: 48, or a polypeptide consisting of an amino acid sequence having at least 80% or higher sequence identity to the amino acid sequence of the polypeptide; (6-LFR2) a polypeptide consisting of amino acid residues 35 to 49 of the amino acid sequence represented by SEQ ID NO: 58, or a polypeptide consisting of an amino acid sequence having at least 80% or higher sequence identity to the amino acid sequence of the polypeptide; (7-LFR2) a polypeptide consisting of amino acid residues 35 to 49 of the amino acid sequence represented by SEQ ID NO: 68, or a polypeptide consisting of an amino acid sequence having at least 80% or higher sequence identity to the amino acid sequence of the polypeptide; (8-LFR2) a polypeptide consisting of amino acid residues 35 to 49 of the amino acid sequence represented by SEQ ID NO: 78, or a polypeptide consisting of an amino acid sequence having at least 80% or higher sequence identity to the amino acid sequence of the polypeptide; (9-LFR2) a polypeptide consisting of amino acid residues 35 to 49 of the amino acid sequence represented by SEQ ID NO: 88, or a polypeptide consisting of an amino acid sequence having at least 80% or higher sequence identity to the amino acid sequence of the polypeptide; (10-LFR2) a polypeptide consisting of amino acid residues 35 to 49 of the amino acid sequence represented by SEQ ID NO: 98, or a polypeptide consisting of an amino acid sequence having at least 80% or higher sequence identity to the amino acid sequence of the polypeptide; and (11-LFR2) a polypeptide consisting of amino acid residues 35 to 49 of the amino acid sequence represented by SEQ ID NO: 108, or a polypeptide consisting of an amino acid sequence having at least 80% or higher sequence identity to the amino acid sequence of the polypeptide.

Examples of the L chain FR3 can specifically include: (1-LFR3) a polypeptide consisting of amino acid residues 57 to 88 of the amino acid sequence represented by SEQ ID NO: 8, or a polypeptide consisting of an amino acid sequence having at least 80% or higher sequence identity to the amino acid sequence of the polypeptide; (2-LFR3) a polypeptide consisting of amino acid residues 62 to 93 of the amino acid sequence represented by SEQ ID NO: 18, or a polypeptide consisting of an amino acid sequence having at least 80% or higher sequence identity to the amino acid sequence of the polypeptide; (3-LFR3) a polypeptide consisting of amino acid residues 57 to 88 of the amino acid sequence represented by SEQ ID NO: 28, or a polypeptide consisting of an amino acid sequence having at least 80% or higher sequence identity to the amino acid sequence of the polypeptide; (4-LFR3) a polypeptide consisting of amino acid residues 57 to 88 of the amino acid sequence represented by SEQ ID NO: 38, or a polypeptide consisting of an amino acid sequence having at least 80% or higher sequence identity to the amino acid sequence of the polypeptide; (5-LFR3) a polypeptide consisting of amino acid residues 63 to 94 of the amino acid sequence represented by SEQ ID NO: 48, or a polypeptide consisting of an amino acid sequence having at least 80% or higher sequence identity to the amino acid sequence of the polypeptide; (6-LFR3) a polypeptide consisting of amino acid residues 57 to 88 of the amino acid sequence represented by SEQ ID NO: 58, or a polypeptide consisting of an amino acid sequence having at least 80% or higher sequence identity to the amino acid sequence of the polypeptide; (7-LFR3) a polypeptide consisting of amino acid residues 57 to 88 of the amino acid sequence represented by SEQ ID NO: 68, or a polypeptide consisting of an amino acid sequence having at least 80% or higher sequence identity to the amino acid sequence of the polypeptide; (8-LFR3) a polypeptide consisting of amino acid residues 57 to 88 of the amino acid sequence represented by SEQ ID NO: 78, or a polypeptide consisting of an amino acid sequence having at least 80% or higher sequence identity to the amino acid sequence of the polypeptide; (9-LFR3) a polypeptide consisting of amino acid residues 57 to 88 of the amino acid sequence represented by SEQ ID NO: 88, or a polypeptide consisting of an amino acid sequence having at least 80% or higher sequence identity to the amino acid sequence of the polypeptide; (10-LFR3) a polypeptide consisting of amino acid residues 57 to 88 of the amino acid sequence represented by SEQ ID NO: 98, or a polypeptide consisting of an amino acid sequence having at least 80% or higher sequence identity to the amino acid sequence of the polypeptide; and (11-LFR3) a polypeptide consisting of amino acid residues 57 to 88 of the amino acid sequence represented by SEQ ID NO: 108, or a polypeptide consisting of an amino acid sequence having at least 80% or higher sequence identity to the amino acid sequence of the polypeptide.

Examples of the L chain FR4 can specifically include: (1-LFR4) a polypeptide consisting of amino acid residues 98 to 108 of the amino acid sequence represented by SEQ ID NO: 8, or a polypeptide consisting of an amino acid sequence having at least 80% or higher sequence identity to the amino acid sequence of the polypeptide; (2-LFR4) a polypeptide consisting of amino acid residues 103 to 113 of the amino acid sequence represented by SEQ ID NO: 18, or a polypeptide consisting of an amino acid sequence having at least 80% or higher sequence identity to the amino acid sequence of the polypeptide; (3-LFR4) a polypeptide consisting of amino acid residues 97 to 107 of the amino acid sequence represented by SEQ ID NO: 28, or a polypeptide consisting of an amino acid sequence having at least 80% or higher sequence identity to the amino acid sequence of the polypeptide; (4-LFR4) a polypeptide consisting of amino acid residues 98 to 108 of the amino acid sequence represented by SEQ ID NO: 38, or a polypeptide consisting of an amino acid sequence having at least 80% or higher sequence identity to the amino acid sequence of the polypeptide; (5-LFR4) a polypeptide consisting of amino acid residues 104 to 114 of the amino acid sequence represented by SEQ ID NO: 48, or a polypeptide consisting of an amino acid sequence having at least 80% or higher sequence identity to the amino acid sequence of the polypeptide; (6-LFR4) a polypeptide consisting of amino acid residues 98 to 108 of the amino acid sequence represented by SEQ ID NO: 58, or a polypeptide consisting of an amino acid sequence having at least 80% or higher sequence identity to the amino acid sequence of the polypeptide; (7-LFR4) a polypeptide consisting of amino acid residues 98 to 108 of the amino acid sequence represented by SEQ ID NO: 68, or a polypeptide consisting of an amino acid sequence having at least 80% or higher sequence identity to the amino acid sequence of the polypeptide; (8-LFR4) a polypeptide consisting of amino acid residues 98 to 108 of the amino acid sequence represented by SEQ ID NO: 78, or a polypeptide consisting of an amino acid sequence having at least 80% or higher sequence identity to the amino acid sequence of the polypeptide; (9-LFR4) a polypeptide consisting of amino acid residues 98 to 108 of the amino acid sequence represented by SEQ ID NO: 88, or a polypeptide consisting of an amino acid sequence having at least 80% or higher sequence identity to the amino acid sequence of the polypeptide; (10-LFR4) a polypeptide consisting of amino acid residues 98 to 108 of the amino acid sequence represented by SEQ ID NO: 98, or a polypeptide consisting of an amino acid sequence having at least 80% or higher sequence identity to the amino acid sequence of the polypeptide; and (11-LFR4) a polypeptide consisting of amino acid residues 98 to 108 of the amino acid sequence represented by SEQ ID NO: 108, or a polypeptide consisting of an amino acid sequence having at least 80% or higher sequence identity to the amino acid sequence of the polypeptide.

The FRs of the present antibody are preferably FRs of a known human antibody. Examples of such "FRs of a known human antibody" can include FRs of a human antibody registered in a sequence database known in the art such as GenBank, and FRs selected from a common sequence (human most homologous consensus sequence; Kabat, E. A. et al., Sequences of Proteins of Immunological Interest, US Dept. Health and Human Services, 1991) derived from each subgroup of a human antibody.

The H chain CDR1 in the present antibody usually resides at positions H31 to H35 based on Kabat numbering (see the document "Kabat, E. A. et al., (1991) NIH Publication No. 91-3242, sequences of proteins of immunological interest"). The H chain CDR2 in the present antibody usually resides at positions H50 to H52, H52A, and H53 to H65 based on Kabat numbering. The H chain CDR3 in the present antibody usually resides at positions H95 to H100, H100A, H100B, H101, and H102 based on Kabat numbering. The L chain CDR1 in the present antibody usually resides at positions L24 to L34 based on Kabat numbering. The L chain CDR2 in the present antibody usually resides at positions L50 to L56 based on Kabat numbering. The L chain CDR3 in the present antibody usually resides at positions L89 to L97 based on Kabat numbering.

Examples of the antibody comprising the H chain and L chain CDR1 to CDR3 described above in (1-1) as the present antibody can include an antibody comprising the H chain and L chain variable (V) regions described above in (1-2) and can specifically include: the single chain antibody described above in (1-3); the single chain antibody described above in (1-3'-1), the single chain antibody described above in (1-3'-2), and the single chain antibody described above in (1-3'-3); and an antibody comprising the H chain and the L chain described above in (1-4). Examples of the antibody comprising the H chain and L chain CDR1 to CDR3 described above in (2-1) can include an antibody comprising the H chain and L chain V regions described above in (2-2) and can specifically include: the single chain antibody described above in (2-3); the single chain antibody described above in (2-3'-1), the single chain antibody described above in (2-3'-2), the single chain antibody described above in (2-3'-3), and the single chain antibody described above in (2-3'-4); and an antibody comprising the H chain and the L chain described above in (2-4). Examples of the antibody comprising the H chain and L chain CDR1 to CDR3 described above in (3-1) can include an antibody comprising the H chain and L chain V regions described above in (3-2) and can specifically include: the single chain antibody described above in (3-3); and an antibody comprising the H chain and the L chain described above in (3-4). Examples of the antibody comprising the H chain and L chain CDR1 to CDR3 described above in (4-1) can include an antibody comprising the H chain and L chain V regions described above in (4-2) and can specifically include: the single chain antibody described above in (4-3); and an antibody comprising the H chain and the L chain described above in (4-4). Examples of the antibody comprising the H chain and L chain CDR1 to CDR3 described above in (5-1) can include an antibody comprising the H chain and L chain V regions described above in (5-2) and can specifically include: the single chain antibody described above in (5-3); and an antibody comprising the H chain and the L chain described above in (5-4). Examples of the antibody comprising the H chain and L chain CDR1 to CDR3 described above in (6-1) can include an antibody comprising the H chain and L chain V regions described above in (6-2) and can specifically include: the single chain antibody described above in (6-3); and an antibody comprising the H chain and the L chain described above in (6-4). Examples of the antibody comprising the H chain and L chain CDR1 to CDR3 described above in (7-1) can include an antibody comprising the H chain and L chain V regions described above in (7-2) and can specifically include: the single chain antibody described above in (7-3); and an antibody comprising the H chain and the L chain described above in (7-4). Examples of the antibody comprising the H chain and L chain CDR1 to CDR3 described above in (8-1) can include an antibody comprising the H chain and L chain V regions described above in (8-2) and can specifically include: the single chain antibody described above in (8-3); and an antibody comprising the H chain and the L chain described above in (8-4). Examples of the antibody comprising the H chain and L chain CDR1 to CDR3 described above in (9-1) can include an antibody comprising the H chain and L chain V regions described above in (9-2) and can specifically include: the single chain antibody described above in (9-3); and an antibody comprising the H chain and the L chain described above in (9-4). Examples of the antibody comprising the H chain and L chain CDR1 to CDR3 described above in (10-1) can include an antibody comprising the H chain and L chain V regions described above in (10-2) and can specifically include: the single chain antibody described above in (10-3); and an antibody comprising the H chain and the L chain described above in (10-4). Examples of the antibody comprising the H chain and L chain CDR1 to CDR3 described above in (11-1) can include an antibody comprising the H chain and L chain V regions described above in (11-2) and can specifically include: the single chain antibody described above in (11-3); and an antibody comprising the H chain and the L chain described above in (11-4). The heavy chain variable region and the light chain variable region in the single chain antibody are usually bound via a peptide linker.

The present CAR can comprise the present single chain antibody, a transmembrane region fused with the C terminus of the present single chain antibody, and an immunocompetent cell activation signal transduction region fused with the C terminus of the transmembrane region. In this context, the fusion between the present single chain antibody and the transmembrane region, or between the transmembrane region and the immunocompetent cell activation signal transduction region may be mediated by a peptide linker or an IgG4 hinge region.

Examples of the length of the peptide linker in the present antibody can include 1 to 100 amino acid residues, preferably 10 to 50 amino acid residues. Examples of the peptide linker in the present antibody can specifically include a consecutive linkage of 3 amino acid sequences each consisting of 1 to 4 glycine residues and 1 serine residue.

The transmembrane region can be any peptide that can penetrate a cell membrane. Examples thereof can include a transmembrane region derived from CD8, a T cell receptor α or β chain, CD3ζ, CD28, CD3ε, CD45, CD4, CD5, CD8, CD9, CD16, CD22, CD33, CD37, CD64, CD80, CD86, CD134, CD137, ICOS, CD154, EGFR (epidermal growth factor receptor), or GITR and can specifically include a human CD8 transmembrane region consisting of amino acid residues 1 to 83 of the amino acid sequence represented by SEQ ID NO: 185. Alternatively, the transmembrane region may be derived from a peptide that can penetrate cell membrane by the truncation of C-terminal 1 to 10 amino acid residues, preferably 6 or 7 amino acid residues. Examples thereof can include engineered form 1 of the human CD8 transmembrane region consisting of amino acid residues 1 to 77 of the amino acid sequence represented by SEQ ID NO: 186, and engineered form 2 of the human CD8 transmembrane region consisting of amino acid residues 1 to 76 of the amino acid sequence represented by SEQ ID NO: 187.

The immunocompetent cell activation signal transduction region can be any region capable of transducing a signal into immunocompetent cells upon binding of the present single chain antibody to human GPC3. The immunocompetent cell activation signal transduction region preferably comprises at least one or more members selected from polypeptides of the intracellular regions of CD28, 4-1BB (CD137), GITR, CD27, OX40, HVEM, CD3ζ, and Fc receptor-associated γ chain, and more preferably comprises three polypeptides of the intracellular regions of CD28, 4-1BB, and CD3ζ. Examples of such a polypeptide of the intracellular region of CD28 can specifically include a polypeptide of the intracellular region of human CD28 consisting of amino acid residues 85 to 124 of the amino acid sequence represented by SEQ ID NO: 185. Examples of the "polypeptide of the intracellular region of 4-1BB" can specifically include a polypeptide of the intracellular region of human 4-1BB consisting of amino acid residues 125 to 170 of the amino acid sequence represented by SEQ ID NO: 185. Examples of the polypeptide of the intracellular region of CD3ζ can specifically include a polypeptide of the intracellular region of human CD3ζ consisting of amino acid residues 172 to 283 of the amino acid sequence represented by SEQ ID NO: 185.

Arginine (Arg) at position 84 of the amino acid sequence represented by SEQ ID NO: 185, arginine at position 78 of the amino acid sequence represented by SEQ ID NO: 186, and arginine at position 77 of the amino acid sequence represented by SEQ ID NO: 187 are a common sequence between the polypeptide of the transmembrane region derived from human CD8 and the polypeptide of the intracellular region of human CD28. Leucine (Leu) at position 171 of the amino acid sequence represented by SEQ ID NO: 185, leucine at position 165 of the amino acid sequence represented by SEQ ID NO: 186, and leucine at position 164 of the amino acid sequence represented by SEQ ID NO: 187 are a common sequence between the polypeptide of the intracellular region of human 4-1BB and the polypeptide of the intracellular region of human CD3.

In the present specification, the "immunocompetent cell" means a cell responsible for immune functions in a living body. Examples of the immunocompetent cell can include: a lymphoid cell such as a T cell, a natural killer cell (NK cell), and a B cell; an antigen-presenting cell such as a monocyte, a macrophage, and a dendritic cell; and a granulocyte such as a neutrophil, an eosinophil, a basophil, and a mast cell. Specific examples thereof can preferably include a T cell derived from a mammal such as a human, a dog, a cat, a pig, or a mouse, preferably a human-derived T cell. The T cell can be obtained by isolation or purification from an immunocompetent cell infiltrating a body fluid such as blood or bone marrow fluid, a tissue of the spleen, the thymus, lymph node or the like, or a cancer tissue of primary tumor, metastatic tumor, cancerous ascites or the like. Alternatively, a T cell prepared from an ES cell or an iPS cell may be utilized. Examples of such a T cell can include an alpha-beta T cell, a gamma-delta T cell, a $CD8^+$ T cell, a $CD4^+$ T cell, a tumor-infiltrating T cell, a memory T cell, a naive T cell, and a NKT cell. The origin of the immunocompetent cell may be the same as or different from an administration subject. When the administration subject is a human, an autologous cell collected from a patient as the administration subject may be used as the immunocompetent cell, or any of other cells collected from a person other than the administration subject may be used as the immunocompetent cell. Specifically, the donor and the recipient may be the same or different and is preferably the same.

Examples of the administration subject can preferably include a mammal and a mammalian cell. Examples of the mammal can more preferably include a human, a mouse, a dog, a rat, a guinea pig, a rabbit, a bird, sheep, a pig, cattle, a horse, a cat, a monkey, and a chimpanzee, particularly preferably a human.

The present CAR is preferably used for ex vivo expression on the cell surface of the immunocompetent cell collected from a cancer patient in cancer treatment. In the case of using a T cell as the immunocompetent cell, examples of the peptide consisting of the transmembrane region and the immunocompetent cell activation signal transduction region fused with the C terminus of the transmembrane region in the present CAR can specifically include a peptide consisting of the amino acid sequence represented by any of SEQ ID NOs: 185 to 187. Examples of the present CAR can specifically include CAR comprising single chain antibody selected from the group consisting of the single chain antibody described above in (1-3), the single chain antibody described above in (2-3), the single chain antibody described above in (1-3'-1), the single chain antibody described above in (1-3'-2), the single chain antibody described above in (1-3'-3), the single chain antibody described above in (2-3'-1), the single chain antibody described above in (2-3'-2), the single chain antibody described above in (2-3'-3), and the single chain antibody described above in (2-3'-4), and a peptide consisting of the amino acid sequence represented by any of SEQ ID NOs: 185 to 187, fused with the C terminus of the single chain antibody.

Specifically, examples of the present CAR can include CAR comprising the single chain antibody described above in (1-3), and a peptide consisting of the amino acid sequence represented by SEQ ID NO: 185,
CAR comprising the single chain antibody described above in (1-3), and a peptide consisting of the amino acid sequence represented by SEQ ID NO: 186,
CAR comprising the single chain antibody described above in (1-3), and a peptide consisting of the amino acid sequence represented by SEQ ID NO: 187,
CAR comprising the single chain antibody described above in (1-3'-1), and a peptide consisting of the amino acid sequence represented by SEQ ID NO: 185,
CAR comprising the single chain antibody described above in (1-3'-1), and a peptide consisting of the amino acid sequence represented by SEQ ID NO: 186,
CAR comprising the single chain antibody described above in (1-3'-1), and a peptide consisting of the amino acid sequence represented by SEQ ID NO: 187,
CAR comprising the single chain antibody described above in (1-3'-2), and a peptide consisting of the amino acid sequence represented by SEQ ID NO: 185,
CAR comprising the single chain antibody described above in (1-3'-2), and a peptide consisting of the amino acid sequence represented by SEQ ID NO: 186,
CAR comprising the single chain antibody described above in (1-3'-2), and a peptide consisting of the amino acid sequence represented by SEQ ID NO: 187,
CAR comprising the single chain antibody described above in (1-3'-3), and a peptide consisting of the amino acid sequence represented by SEQ ID NO: 185,
CAR comprising the single chain antibody described above in (1-3'-3), and a peptide consisting of the amino acid sequence represented by SEQ ID NO: 186,
CAR comprising the single chain antibody described above in (1-3'-3), and a peptide consisting of the amino acid sequence represented by SEQ ID NO: 187,
CAR comprising the single chain antibody described above in (2-3), and a peptide consisting of the amino acid sequence represented by SEQ ID NO: 185,
CAR comprising the single chain antibody described above in (2-3), and a peptide consisting of the amino acid sequence represented by SEQ ID NO: 186,
CAR comprising the single chain antibody described above in (2-3), and a peptide consisting of the amino acid sequence represented by SEQ ID NO: 187,
CAR comprising the single chain antibody described above in (2-3'-1), and a peptide consisting of the amino acid sequence represented by SEQ ID NO: 185,
CAR comprising the single chain antibody described above in (2-3'-1), and a peptide consisting of the amino acid sequence represented by SEQ ID NO: 186,
CAR comprising the single chain antibody described above in (2-3'-1), and a peptide consisting of the amino acid sequence represented by SEQ ID NO: 187,
CAR comprising the single chain antibody described above in (2-3'-2), and a peptide consisting of the amino acid sequence represented by SEQ ID NO: 185,
CAR comprising the single chain antibody described above in (2-3'-2), and a peptide consisting of the amino acid sequence represented by SEQ ID NO: 186,
CAR comprising the single chain antibody described above in (2-3'-2), and a peptide consisting of the amino acid sequence represented by SEQ ID NO: 187,
CAR comprising the single chain antibody described above in (2-3'-3), and a peptide consisting of the amino acid sequence represented by SEQ ID NO: 185,
CAR comprising the single chain antibody described above in (2-3'-3), and a peptide consisting of the amino acid sequence represented by SEQ ID NO: 186,
CAR comprising the single chain antibody described above in (2-3'-3), and a peptide consisting of the amino acid sequence represented by SEQ ID NO: 187,
CAR comprising the single chain antibody described above in (2-3'-4), and a peptide consisting of the amino acid sequence represented by SEQ ID NO: 185,
CAR comprising the single chain antibody described above in (2-3'-4), and a peptide consisting of the amino acid sequence represented by SEQ ID NO: 186, and
CAR comprising the single chain antibody described above in (2-3'-4), and a peptide consisting of the amino acid sequence represented by SEQ ID NO: 187.

The present immunocompetent cell can be any immunocompetent cell expressing CAR. Since CAR usually does not occur naturally, the immunocompetent cell expresses foreign CAR, not endogenous CAR. The present immunocompetent cell preferably further expresses IL-7 and/or CCL19. When the immunocompetent cell is a cell found to not express IL-7 and/or CCL19, for example, a T cell, or when the immunocompetent cell is a cell, other than a T cell, low expressing IL-7 and/or CCL19, the present immunocompetent cell preferably expresses foreign IL-7 and/or CCL19.

The present immunocompetent cell can be prepared by introducing the present vector comprising the present CAR gene, and a vector comprising IL-7 and/or CCL19 gene to an immunocompetent cell. The introduction method can be any method for introducing DNA to mammalian cells. Examples thereof can include a method such as electroporation (Cytotechnology, 3, 133 (1990)), calcium phosphate method (Japanese unexamined Patent Application Publication No. 2-227075), lipofection (Proc. Natl. Acad. Sci. U.S.A., 84, 7413 (1987)), and viral infection method. Examples of such a viral infection method can include a method which involves transfecting a packaging cell such as a GP2-293 cell (manufactured by Takara Bio Inc.), a Plat-GP cell (manufactured by Cosmo Bio Co., Ltd.), a PG13 cell (ATCC CRL-10686), or a PA317 cell (ATCC CRL-9078) with a CAR expression vector (International Publication No. WO 2016/056228) and a packaging plasmid to prepare a recombinant virus, and infecting a T cell with the recombinant virus.

The present immunocompetent cell may be produced by incorporating a nucleotide encoding the present CAR and a nucleotide encoding IL-7 and/or CCL19 into the genome of a cell by use of a gene editing technique known in the art such that the nucleotides are expressible under the control of an appropriate promoter. Examples of the gene editing technique known in the art include a technique using endonuclease such as zinc finger nuclease, TALEN (transcription activator-like effector nuclease), or CRISPR (clustered regularly interspaced short palindromic repeat)-Cas system.

The present immunocompetent cell can be used in combination with an additional anticancer agent. Examples of the additional anticancer agent can include: an alkylating drug such as cyclophosphamide, bendamustine, ifosfamide, and dacarbazine; an antimetabolite such as pentostatin, fludarabine, cladribine, methotrexate, 5-fluorouracil, 6-mercaptopurine, and enocitabine; a molecular targeting drug such as rituximab, cetuximab, and trastuzumab; a kinase inhibitor such as imatinib, gefitinib, erlotinib, afatinib, dasatinib, sunitinib, and trametinib; a proteasome inhibitor such as bortezomib; a calcineurin inhibitory drug such as cyclosporin and tacrolimus; an anticancer antibiotic such as idarubicin and doxorubicin mitomycin C; a vegetable alkaloid such as irinotecan and etoposide; a platinum-containing drug such as cisplatin, oxaliplatin, and carboplatin; a hormone therapeutic such as tamoxifen and bicalutamide; and an immunosuppressive drug such as interferon, nivolumab, and pembrolizumab.

Examples of the method for "using the present immunocompetent cell in combination with the additional anticancer agent" can include a method using treatment with the additional anticancer agent followed by use of the present immunocompetent cell, a method using the present immunocompetent cell and the additional anticancer agent at the same time, and a method using treatment with the present immunocompetent cell followed by use of the additional anticancer agent. Use of the present immunocompetent cell in combination with the additional anticancer agent can further improve a therapeutic effect on a cancer and can also reduce their respective adverse reactions by decreasing their respective numbers of administration or doses.

The present antibody gene is not particularly limited as long as the antibody gene (nucleotide) encodes the present antibody. Examples thereof can include (1-1D) an antibody gene comprising: a H chain CDR1 gene consisting of nucleotide residues 91 to 105 of a H chain V region gene consisting of the nucleotide sequence represented by SEQ ID NO: 111 (gene encoding the H chain CDR1 described above in (1-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 111 (gene encoding the H chain CDR2 described above in (1-1)), or a degenerate codon engineered form of the H chain CDR2 gene; and a H chain CDR3 gene consisting of nucleotide residues 295 to 324 of the H chain V region gene consisting of the nucleotide sequence represented by SEQ ID NO: 111 (gene encoding the H chain CDR3 described above in (1-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 112 (gene encoding the L chain CDR1 described above in (1-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 112 (gene encoding the L chain CDR2 described above in (1-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 112 (gene encoding the L chain CDR3 described above in (1-1)), or a degenerate codon engineered form of the L chain CDR3 gene, (2-1D) an antibody gene comprising: a H chain CDR1 gene consisting of nucleotide residues 91 to 105 of a H chain V region gene consisting of the nucleotide sequence represented by SEQ ID NO: 115 (gene encoding the H chain CDR1 described above in (2-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 115 (gene encoding the H chain CDR2 described above in (2-1)), or a degenerate codon engineered form of the H chain CDR2 gene; and a H chain CDR3 gene consisting of nucleotide residues 295 to 321 of the H chain V region gene consisting of the nucleotide sequence represented by SEQ ID NO: 115 (gene encoding the H chain CDR3 described above in (2-1)), or a degenerate codon engineered form of the H chain CDR3 gene; and a L chain CDR1 gene consisting of nucleotide residues 70 to 117 of a L chain V region gene consisting of the nucleotide sequence represented by SEQ ID NO: 116 (gene encoding the L chain CDR1 described above in (2-1)), or a degenerate codon engineered form of the L chain CDR1 gene; a L chain CDR2 gene consisting of nucleotide residues 163 to 183 of the L chain V region gene consisting of the nucleotide sequence represented by SEQ ID NO: 116 (gene encoding the L chain CDR2 described above in (2-1)), or a degenerate codon engineered form of the L chain CDR2 gene; and a L chain CDR3 gene consisting of nucleotide residues 280 to 306 of the L chain V region gene consisting of the nucleotide sequence represented by SEQ ID NO: 116 (gene encoding the L chain CDR3 described above in (2-1)), or a degenerate codon engineered form of the L chain CDR3 gene, (3-1D) an antibody gene comprising: a H chain CDR1 gene consisting of nucleotide residues 91 to 105 of a H chain V region gene consisting of the nucleotide sequence represented by SEQ ID NO: 119 (gene encoding the H chain CDR1 described above in (3-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 119 (gene encoding the H chain CDR2 described above in (3-1)), or a degenerate codon engineered form of the H chain CDR2 gene; and a H chain CDR3 gene consisting of nucleotide residues 295 to 315 of the H chain V region gene consisting of the nucleotide sequence represented by SEQ ID NO: 119 (gene encoding the H chain CDR3 described above in (3-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 120 (gene encoding the L chain CDR1 described above in (3-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 120 (gene encoding the L chain CDR2 described above in (3-1)), or a degenerate codon engineered form of the L chain CDR2 gene; and a L chain CDR3 gene consisting of nucleotide residues 265 to 288 of the L chain V region gene consisting of the nucleotide sequence represented by SEQ ID NO: 120 (gene encoding the L chain CDR3 described above in (3-1)), or a degenerate codon engineered form of the L chain CDR3 gene, (4-1D) an antibody gene comprising: a H chain CDR1 gene consisting of nucleotide residues 91 to 105 of a H chain V region gene consisting of the nucleotide sequence represented by SEQ ID NO: 123 (gene encoding the H chain CDR1 described above in (4-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 123 (gene encoding the H chain CDR2 described above in (4-1)), or a degenerate codon engineered form of the H chain CDR2 gene; and a H chain CDR3 gene consisting of nucleotide residues 298 to 330 of the H chain V region gene consisting of the nucleotide sequence represented by SEQ ID NO: 123 (gene encoding the H chain CDR3 described above in (4-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 124 (gene encoding the L chain CDR1 described above in (4-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 124 (gene encoding the L chain CDR2 described above in (4-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 124 (gene encoding the L chain CDR3 described above in (4-1)), or a degenerate codon engineered form of the L chain CDR3 gene, (5-1D) an antibody gene comprising: a H chain CDR1 gene consisting of nucleotide residues 91 to 105 of a H chain V region gene consisting of the nucleotide sequence represented by SEQ ID NO: 127 (gene encoding the H chain CDR1 described above in (5-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 127 (gene encoding the H chain CDR2 described above in (5-1)), or a degenerate codon engineered form of the H chain CDR2 gene; and a H chain CDR3 gene consisting of nucleotide residues 298 to 321 of the H chain V region gene consisting of the nucleotide sequence represented by SEQ ID NO: 127 (gene encoding the H chain CDR3 described above in (5-1)), or a degenerate codon engineered form of the H chain CDR3 gene; and a L chain CDR1 gene consisting of nucleotide residues 70 to 120 of a L chain V region gene consisting of the nucleotide sequence represented by SEQ ID NO: 128 (gene encoding the L chain CDR1 described above in (5-1)), or a degenerate codon engineered form of the L chain CDR1 gene; a L chain CDR2 gene consisting of nucleotide residues 166 to 186 of the L chain V region gene consisting of the nucleotide sequence represented by SEQ ID NO: 128 (gene encoding the L chain CDR2 described above in (5-1)), or a degenerate codon engineered form of the L chain CDR2 gene; and a L chain CDR3 gene consisting of nucleotide residues 283 to 309 of the L chain V region gene consisting of the nucleotide sequence represented by SEQ ID NO: 128 (gene encoding the L chain CDR3 described above in (5-1)), or a degenerate codon engineered form of the L chain CDR3 gene, (6-1D) an antibody gene comprising: a H chain CDR1 gene consisting of nucleotide residues 91 to 105 of a H chain V region gene consisting of the nucleotide sequence represented by SEQ ID NO: 131 (gene encoding the H chain CDR1 described above in (6-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 131 (gene encoding the H chain CDR2 described above in (6-1)), or a degenerate codon engineered form of the H chain CDR2 gene; and a H chain CDR3 gene consisting of nucleotide residues 295 to 318 of the H chain V region gene consisting of the nucleotide sequence represented by SEQ ID NO: 131 (gene encoding the H chain CDR3 described above in (6-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 132 (gene encoding the L chain CDR1 described above in (6-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 132 (gene encoding the L chain CDR2 described above in (6-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 132 (gene encoding the L chain CDR3 described above in (6-1)), or a degenerate codon engineered form of the L chain CDR3 gene, (7-1D) an antibody gene comprising: a H chain CDR1 gene consisting of nucleotide residues 91 to 105 of a H chain V region gene consisting of the nucleotide sequence represented by SEQ ID NO: 135 (gene encoding the H chain CDR1 described above in (7-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 135 (gene encoding the H chain CDR2 described above in (7-1)), or a degenerate codon engineered form of the H chain CDR2 gene; and a H chain CDR3 gene consisting of nucleotide residues 295 to 315 of the H chain V region gene consisting of the nucleotide sequence represented by SEQ ID NO: 135 (gene encoding the H chain CDR3 described above in (7-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 136 (gene encoding the L chain CDR1 described above in (7-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 136 (gene encoding the L chain CDR2 described above in (7-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 136 (gene encoding the L chain CDR3 described above in (7-1)), or a degenerate codon engineered form of the L chain CDR3 gene, (8-1D) an antibody gene comprising: a H chain CDR1 gene consisting of nucleotide residues 91 to 105 of a H chain V region gene consisting of the nucleotide sequence represented by SEQ ID NO: 139 (gene encoding the H chain CDR1 described above in (8-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 139 (gene encoding the H chain CDR2 described above in (8-1)), or a degenerate codon engineered form of the H chain CDR2 gene; and a H chain CDR3 gene consisting of nucleotide residues 295 to 315 of the H chain V region gene consisting of the nucleotide sequence represented by SEQ ID NO: 139 (gene encoding the H chain CDR3 described above in (8-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 140 (gene encoding the L chain CDR1 described above in (8-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 140 (gene encoding the L chain CDR2 described above in (8-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 140 (gene encoding the L chain CDR3 described above in (8-1)), or a degenerate codon engineered form of the L chain CDR3 gene, (9-1D) an antibody gene comprising: a H chain CDR1 gene consisting of nucleotide residues 91 to 105 of a H chain V region gene consisting of the nucleotide sequence represented by SEQ ID NO: 143 (gene encoding the H chain CDR1 described above in (9-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 143 (gene encoding the H chain CDR2 described above in (9-1)), or a degenerate codon engineered form of the H chain CDR2 gene; and a H chain CDR3 gene consisting of nucleotide residues 298 to 330 of the H chain V region gene consisting of the nucleotide sequence represented by SEQ ID NO: 143 (gene encoding the H chain CDR3 described above in (9-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 144 (gene encoding the L chain CDR1 described above in (9-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 144 (gene encoding the L chain CDR2 described above in (9-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 144 (gene encoding the L chain CDR3 described above in (9-1)), or a degenerate codon engineered form of the L chain CDR3 gene, (10-1D) an antibody gene comprising: a H chain CDR1 gene consisting of nucleotide residues 91 to 105 of a H chain V region gene consisting of the nucleotide sequence represented by SEQ ID NO: 147 (gene encoding the H chain CDR1 described above in (10-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 147 (gene encoding the H chain CDR2 described above in (10-1)), or a degenerate codon engineered form of the H chain CDR2 gene; and a H chain CDR3 gene consisting of nucleotide residues 295 to 327 of the H chain V region gene consisting of the nucleotide sequence represented by SEQ ID NO: 147 (gene encoding the H chain CDR3 described above in (10-1)), or a degenerate codon engineered form of the H chain CDR3 gene; and a L chain CDR1 gene consisting of nucleotide residues 70 to 102 of a L chain V region gene consisting of the nucleotide sequence represented by SEQ ID NO: 148 (gene encoding the L chain CDR1 described above in (10-1)), or a degenerate codon engineered form of the L chain CDR1 gene; a L chain CDR2 gene consisting of nucleotide residues 148 to 168 of the L chain V region gene consisting of the nucleotide sequence represented by SEQ ID NO: 148 (gene encoding the L chain CDR2 described above in (10-1)), or a degenerate codon engineered form of the L chain CDR2 gene; and a L chain CDR3 gene consisting of nucleotide residues 265 to 291 of the L chain V region gene consisting of the nucleotide sequence represented by SEQ ID NO: 148 (gene encoding the L chain CDR3 described above in (10-1)), or a degenerate codon engineered form of the L chain CDR3 gene, and (11-1D) an antibody gene comprising: a H chain CDR1 gene consisting of nucleotide residues 91 to 105 of a H chain V region gene consisting of the nucleotide sequence represented by SEQ ID NO: 151 (gene encoding the H chain CDR1 described above in (11-1)), or a degenerate codon engineered form of the H chain CDR1 gene; a H chain CDR2 gene consisting of nucleotide residues 148 to 198 of the H chain V region gene consisting of the nucleotide sequence represented by SEQ ID NO: 151 (gene encoding the H chain CDR2 described above in (11-1)), or a degenerate codon engineered form of the H chain CDR2 gene; and a H chain CDR3 gene consisting of nucleotide residues 295 to 324 of the H chain V region consisting of the nucleotide sequence represented by SEQ ID NO: 151 (gene encoding the H chain CDR3 described above in (11-1)), or a degenerate codon engineered form of the H chain CDR3 gene.

Further examples of the present antibody gene can include (1-2D) an antibody gene comprising a H chain variable region gene consisting of a nucleotide sequence having at least 80% or higher sequence identity to the nucleotide sequence represented by SEQ ID NO: 111 (gene encoding a H chain variable region consisting of an amino acid sequence having at least 80% or higher sequence identity to the amino acid sequence represented by SEQ ID NO: 7), and a L chain variable region gene consisting of a nucleotide sequence having at least 80% or higher sequence identity to the nucleotide sequence represented by SEQ ID NO: 112 (gene encoding a L chain variable region consisting of an amino acid sequence having at least 80% or higher sequence identity to the amino acid sequence represented by SEQ ID NO: 8), (2-2D) an antibody gene comprising a H chain variable region gene consisting of a nucleotide sequence having at least 80% or higher sequence identity to the nucleotide sequence represented by SEQ ID NO: 115 (gene encoding a H chain variable region consisting of an amino acid sequence having at least 80% or higher sequence identity to the amino acid sequence represented by SEQ ID NO: 17), and a L chain variable region gene consisting of a nucleotide sequence having at least 80% or higher sequence identity to the nucleotide sequence represented by SEQ ID NO: 116 (gene encoding a L chain variable region consisting of an amino acid sequence having at least 80% or higher sequence identity to the amino acid sequence represented by SEQ ID NO: 18), (3-2D) an antibody gene comprising a H chain variable region gene consisting of a nucleotide sequence having at least 80% or higher sequence identity to the nucleotide sequence represented by SEQ ID NO: 119 (gene encoding a H chain variable region consisting of an amino acid sequence having at least 80% or higher sequence identity to the amino acid sequence represented by SEQ ID NO: 27), and a L chain variable region gene consisting of a nucleotide sequence having at least 80% or higher sequence identity to the nucleotide sequence represented by SEQ ID NO: 120 (gene encoding a L chain variable region consisting of an amino acid sequence having at least 80% or higher sequence identity to the amino acid sequence represented by SEQ ID NO: 28), (4-2D) an antibody gene comprising a H chain variable region gene consisting of a nucleotide sequence having at least 80% or higher sequence identity to the nucleotide sequence represented by SEQ ID NO: 123 (gene encoding a H chain variable region consisting of an amino acid sequence having at least 80% or higher sequence identity to the amino acid sequence represented by SEQ ID NO: 37), and a L chain variable region gene consisting of a nucleotide sequence having at least 80% or higher sequence identity to the nucleotide sequence represented by SEQ ID NO: 124 (gene encoding a L chain variable region consisting of an amino acid sequence having at least 80% or higher sequence identity to the amino acid sequence represented by SEQ ID NO: 38), (5-2D) an antibody gene comprising a H chain variable region gene consisting of a nucleotide sequence having at least 80% or higher sequence identity to the nucleotide sequence represented by SEQ ID NO: 127 (gene encoding a H chain variable region consisting of an amino acid sequence having at least 80% or higher sequence identity to the amino acid sequence represented by SEQ ID NO: 47), and a L chain variable region gene consisting of a nucleotide sequence having at least 80% or higher sequence identity to the nucleotide sequence represented by SEQ ID NO: 128 (gene encoding a L chain variable region consisting of an amino acid sequence having at least 80% or higher sequence identity to the amino acid sequence represented by SEQ ID NO: 48), (6-2D) an antibody gene comprising a H chain variable region gene consisting of a nucleotide sequence having at least 80% or higher sequence identity to the nucleotide sequence represented by SEQ ID NO: 131 (gene encoding a H chain variable region consisting of an amino acid sequence having at least 80% or higher sequence identity to the amino acid sequence represented by SEQ ID NO: 57), and a L chain variable region gene consisting of a nucleotide sequence having at least 80% or higher sequence identity to the nucleotide sequence represented by SEQ ID NO: 132 (gene encoding a L chain variable region consisting of an amino acid sequence having at least 80% or higher sequence identity to the amino acid sequence represented by SEQ ID NO: 58), (7-2D) an antibody gene comprising a H chain variable region gene consisting of a nucleotide sequence having at least 80% or higher sequence identity to the nucleotide sequence represented by SEQ ID NO: 135 (gene encoding a H chain variable region consisting of an amino acid sequence having at least 80% or higher sequence identity to the amino acid sequence represented by SEQ ID NO: 67), and a L chain variable region gene consisting of a nucleotide sequence having at least 80% or higher sequence identity to the nucleotide sequence represented by SEQ ID NO: 136 (gene encoding a L chain variable region consisting of an amino acid sequence having at least 80% or higher sequence identity to the amino acid sequence represented by SEQ ID NO: 68), (8-2D) an antibody gene comprising a H chain variable region gene consisting of a nucleotide sequence having at least 80% or higher sequence identity to the nucleotide sequence represented by SEQ ID NO: 139 (gene encoding a H chain variable region consisting of an amino acid sequence having at least 80% or higher sequence identity to the amino acid sequence represented by SEQ ID NO: 77), and a L chain variable region gene consisting of a nucleotide sequence having at least 80% or higher sequence identity to the nucleotide sequence represented by SEQ ID NO: 140 (gene encoding a L chain variable region consisting of an amino acid sequence having at least 80% or higher sequence identity to the amino acid sequence represented by SEQ ID NO: 78), (9-2D) an antibody gene comprising a H chain variable region gene consisting of a nucleotide sequence having at least 80% or higher sequence identity to the nucleotide sequence represented by SEQ ID NO: 143 (gene encoding a H chain variable region consisting of an amino acid sequence having at least 80% or higher sequence identity to the amino acid sequence represented by SEQ ID NO: 87), and a L chain variable region gene consisting of a nucleotide sequence having at least 80% or higher sequence identity to the nucleotide sequence represented by SEQ ID NO: 144 (gene encoding a L chain variable region consisting of an amino acid sequence having at least 80% or higher sequence identity to the amino acid sequence represented by SEQ ID NO: 88), (10-2D) an antibody gene comprising a H chain variable region gene consisting of a nucleotide sequence having at least 80% or higher sequence identity to the nucleotide sequence represented by SEQ ID NO: 147 (gene encoding a H chain variable region consisting of an amino acid sequence having at least 80% or higher sequence identity to the amino acid sequence represented by SEQ ID NO: 97), and a L chain variable region gene consisting of a nucleotide sequence having at least 80% or higher sequence identity to the nucleotide sequence represented by SEQ ID NO: 148 (gene encoding a L chain variable region consisting of an amino acid sequence having at least 80% or higher sequence identity to the amino acid sequence represented by SEQ ID NO: 98), and (11-2D) an antibody gene comprising a H chain variable region gene consisting of a nucleotide sequence having at least 80% or higher sequence identity to the nucleotide sequence represented by SEQ ID NO: 151 (gene encoding a H chain variable region consisting of an amino acid sequence having at least 80% or higher sequence identity to the amino acid sequence represented by SEQ ID NO: 107), and a L chain variable region gene consisting of a nucleotide sequence having at least 80% or higher sequence identity to the nucleotide sequence represented by SEQ ID NO: 152 (gene encoding a L chain variable region consisting of an amino acid sequence having at least 80% or higher sequence identity to the amino acid sequence represented by SEQ ID NO: 108).

Particularly, examples of the present antibody gene can specifically include (1-4D) an antibody gene comprising a H chain gene consisting of a nucleotide sequence having at least 80% or higher sequence identity to the nucleotide sequence represented by SEQ ID NO: 113 (gene encoding a H chain consisting of an amino acid sequence having at least 80% or higher sequence identity to the amino acid sequence represented by SEQ ID NO: 9), and a L chain gene consisting of a nucleotide sequence having at least 80% or higher sequence identity to the nucleotide sequence represented by SEQ ID NO: 114 (gene encoding a L chain consisting of an amino acid sequence having at least 80% or higher sequence identity to the amino acid sequence represented by SEQ ID NO: 10), (2-4D) an antibody gene comprising a H chain gene consisting of a nucleotide sequence having at least 80% or higher sequence identity to the nucleotide sequence represented by SEQ ID NO: 117 (gene encoding a H chain consisting of an amino acid sequence having at least 80% or higher sequence identity to the amino acid sequence represented by SEQ ID NO: 19), and a L chain gene consisting of a nucleotide sequence having at least 80% or higher sequence identity to the nucleotide sequence represented by SEQ ID NO: 118 (gene encoding a L chain consisting of an amino acid sequence having at least 80% or higher sequence identity to the amino acid sequence represented by SEQ ID NO: 20), (3-4D) an antibody gene comprising a H chain gene consisting of a nucleotide sequence having at least 80% or higher sequence identity to the nucleotide sequence represented by SEQ ID NO: 121 (gene encoding a H chain consisting of an amino acid sequence having at least 80% or higher sequence identity to the amino acid sequence represented by SEQ ID NO: 29), and a L chain gene consisting of a nucleotide sequence having at least 80% or higher sequence identity to the nucleotide sequence represented by SEQ ID NO: 122 (gene encoding a L chain consisting of an amino acid sequence having at least 80% or higher sequence identity to the amino acid sequence represented by SEQ ID NO: 30), (4-4D) an antibody gene comprising a H chain gene consisting of a nucleotide sequence having at least 80% or higher sequence identity to the nucleotide sequence represented by SEQ ID NO: 125 (gene encoding a H chain consisting of an amino acid sequence having at least 80% or higher sequence identity to the amino acid sequence represented by SEQ ID NO: 39), and a L chain gene consisting of a nucleotide sequence having at least 80% or higher sequence identity to the nucleotide sequence represented by SEQ ID NO: 126 (gene encoding a L chain consisting of an amino acid sequence having at least 80% or higher sequence identity to the amino acid sequence represented by SEQ ID NO: 40), (5-4D) an antibody gene comprising a H chain gene consisting of a nucleotide sequence having at least 80% or higher sequence identity to the nucleotide sequence represented by SEQ ID NO: 129 (gene encoding a H chain consisting of an amino acid sequence having at least 80% or higher sequence identity to the amino acid sequence represented by SEQ ID NO: 49), and a L chain gene consisting of a nucleotide sequence having at least 80% or higher sequence identity to the nucleotide sequence represented by SEQ ID NO: 130 (gene encoding a L chain consisting of an amino acid sequence having at least 80% or higher sequence identity to the amino acid sequence represented by SEQ ID NO: 50), (6-4D) an antibody gene comprising a H chain gene consisting of a nucleotide sequence having at least 80% or higher sequence identity to the nucleotide sequence represented by SEQ ID NO: 133 (gene encoding a H chain consisting of an amino acid sequence having at least 80% or higher sequence identity to the amino acid sequence represented by SEQ ID NO: 59), and a L chain gene consisting of a nucleotide sequence having at least 80% or higher sequence identity to the nucleotide sequence represented by SEQ ID NO: 134 (gene encoding a L chain consisting of an amino acid sequence having at least 80% or higher sequence identity to the amino acid sequence represented by SEQ ID NO: 60), (7-4D) an antibody gene comprising a H chain gene consisting of a nucleotide sequence having at least 80% or higher sequence identity to the nucleotide sequence represented by SEQ ID NO: 137 (gene encoding a H chain consisting of an amino acid sequence having at least 80% or higher sequence identity to the amino acid sequence represented by SEQ ID NO: 69), and a L chain gene consisting of a nucleotide sequence having at least 80% or higher sequence identity to the nucleotide sequence represented by SEQ ID NO: 138 (gene encoding a L chain consisting of an amino acid sequence having at least 80% or higher sequence identity to the amino acid sequence represented by SEQ ID NO: 70), (8-4D) an antibody gene comprising a H chain gene consisting of a nucleotide sequence having at least 80% or higher sequence identity to the nucleotide sequence represented by SEQ ID NO: 141 (gene encoding a H chain consisting of an amino acid sequence having at least 80% or higher sequence identity to the amino acid sequence represented by SEQ ID NO: 79), and a L chain gene consisting of a nucleotide sequence having at least 80% or higher sequence identity to the nucleotide sequence represented by SEQ ID NO: 142 (gene encoding a L chain consisting of an amino acid sequence having at least 80% or higher sequence identity to the amino acid sequence represented by SEQ ID NO: 80), (9-4D) an antibody gene comprising a H chain gene consisting of a nucleotide sequence having at least 80% or higher sequence identity to the nucleotide sequence represented by SEQ ID NO: 145 (gene encoding a H chain consisting of an amino acid sequence having at least 80% or higher sequence identity to the amino acid sequence represented by SEQ ID NO: 89), and a L chain gene consisting of a nucleotide sequence having at least 80% or higher sequence identity to the nucleotide sequence represented by SEQ ID NO: 146 (gene encoding a L chain consisting of an amino acid sequence having at least 80% or higher sequence identity to the amino acid sequence represented by SEQ ID NO: 90), (10-4D) an antibody gene comprising a H chain gene consisting of a nucleotide sequence having at least 80% or higher sequence identity to the nucleotide sequence represented by SEQ ID NO: 149 (gene encoding a H chain consisting of an amino acid sequence having at least 80% or higher sequence identity to the amino acid sequence represented by SEQ ID NO: 99), and a L chain gene consisting of a nucleotide sequence having at least 80% or higher sequence identity to the nucleotide sequence represented by SEQ ID NO: 150 (gene encoding a L chain consisting of an amino acid sequence having at least 80% or higher sequence identity to the amino acid sequence represented by SEQ ID NO: 100), and (11-4D) an antibody gene comprising a H chain gene consisting of a nucleotide sequence having at least 80% or higher sequence identity to the nucleotide sequence represented by SEQ ID NO: 153 (gene encoding a H chain consisting of an amino acid sequence having at least 80% or higher sequence identity to the amino acid sequence represented by SEQ ID NO: 109), and a L chain gene consisting of a nucleotide sequence having at least 80% or higher sequence identity to the nucleotide sequence represented by SEQ ID NO: 154 (gene encoding a L chain consisting of an amino acid sequence having at least 80% or higher sequence identity to the amino acid sequence represented by SEQ ID NO: 110).

The present CAR gene is not particularly limited as long as the gene (nucleotide) encodes the present CAR. Examples thereof can specifically include (1-3D) a CAR gene comprising a gene encoding the single chain antibody described above in (1-3), or a degenerate codon engineered form of the gene,
(2-3D) a CAR gene comprising a gene encoding the single chain antibody described above in (2-3), or a degenerate codon engineered form of the gene,
(3-3D) a CAR gene comprising a gene encoding the single chain antibody described above in (3-3), or a degenerate codon engineered form of the gene,
(4-3D) a CAR gene comprising a gene encoding the single chain antibody described above in (4-3), or a degenerate codon engineered form of the gene,
(5-3D) a CAR gene comprising a gene encoding the single chain antibody described above in (5-3), or a degenerate codon engineered form of the gene,
(6-3D) a CAR gene comprising a gene encoding the single chain antibody described above in (6-3), or a degenerate codon engineered form of the gene,
(7-3D) a CAR gene comprising a gene encoding the single chain antibody described above in (7-3), or a degenerate codon engineered form of the gene,
(8-3D) a CAR gene comprising a gene encoding the single chain antibody described above in (8-3), or a degenerate codon engineered form of the gene,
(9-3D) a CAR gene comprising a gene encoding the single chain antibody described above in (9-3), or a degenerate codon engineered form of the gene,
(10-3D) a CAR gene comprising a gene encoding the single chain antibody described above in (10-3), or a degenerate codon engineered form of the gene,
(11-3D) a CAR gene comprising a gene encoding the single chain antibody described above in (11-3), or a degenerate codon engineered form of the gene,
(1-3'-1D) a CAR gene comprising a gene encoding the single chain antibody described above in (1-3'-1), or a degenerate codon engineered form of the gene,
(1-3'-2D) a CAR gene comprising a gene encoding the single chain antibody described above in (1-3'-2), or a degenerate codon engineered form of the gene,
(1-3'-3D) a CAR gene comprising a gene encoding the single chain antibody described above in (1-3'-3), or a degenerate codon engineered form of the gene,
(2-3'-1D) a CAR gene comprising a gene encoding the single chain antibody described above in (2-3'-1), or a degenerate codon engineered form of the gene,
(2-3'-2D) a CAR gene comprising a gene encoding the single chain antibody described above in (2-3'-2), or a degenerate codon engineered form of the gene,
(2-3'-3D) a CAR gene comprising a gene encoding the single chain antibody described above in (2-3'-3), or a degenerate codon engineered form of the gene, and
(2-3'-4D) a CAR gene comprising a gene encoding the single chain antibody described above in (2-3'-4), or a degenerate codon engineered form of the gene.

In the present specification, the phrase "at least 80% or higher identity" means that the identity is 80% or higher, preferably 85% or higher, more preferably 88% or higher, further preferably 90% or higher, still further preferably 93% or higher, particularly preferably 95% or higher, particularly more preferably 98% or higher, most preferably 100%.

In the present specification, the term "identity" means the degree of similarity between polypeptide or polynucleotide sequences (this degree is determined by matching a query sequence to another sequence, preferably of the same type (nucleic acid or protein sequence)). Examples of a preferred computer program method for calculating and determining the "identity" include, but are not limited to, GCG BLAST (Basic Local Alignment Search Tool) (Altschul et al., J. Mol. Biol. 1990, 215: 403-410; Altschul et al., Nucleic Acids Res. 1997, 25: 3389-3402; and Devereux et al., Nucleic Acid Res. 1984, 12: 387), BLASTN 2.0 (Gish W., http://blast.wustl.edu,1996-2002), FASTA (Pearson and Lipman, Proc. Natl. Acad. Sci. USA 1988, 85: 2444-2448), and GCG GelMerge which determines and aligns a pair of the longest overlapping contigs (Wibur and Lipman, SIAM J. Appl. Math. 1984, 44: 557-567; and Needleman and Wunsch, J. Mol. Biol. 1970, 48: 443-453).

In the present specification, the "amino acid sequence having at least 80% or higher sequence identity to the amino acid sequence represented by SEQ ID NO: X" is, in other words, an "amino acid sequence derived from the amino acid sequence represented by SEQ ID NO: X by the deletion, substitution, insertion, and/or addition of 0, 1 or several amino acid residues" and has functions equivalent to those of the amino acid sequence represented by SEQ ID NO: X. In this context, the "amino acid sequence derived by the deletion, substitution, insertion, and/or addition of 1 or several amino acid residues" means an amino acid sequence in which amino acid residues have been deleted, substituted, inserted, and/or added, for example, within the range of 1 to 30 residues, preferably within the range of 1 to 20 residues, more preferably within the range of 1 to 15 residues, further preferably within the range of 1 to 10 residues, further preferably within the range of 1 to 5 residues, further preferably within the range of 1 to 3 residues, further preferably within the range of 1 or 2 residues. The mutation treatment of these amino acid residues can be performed by an arbitrary method known to those skilled in the art such as chemical synthesis, a gene engineering approach, or mutagenesis.

The promoter in the present vector can be any region that starts the transcription of mRNA encoded by the present antibody gene located downstream of the promoter. The promoter usually comprises a transcription start site (TSS).

The type of the promoter or the vector in the present vector can be appropriately selected according to the type of a host cell (or a host organism) to which the present vector is introduced.

The host cell can express the present antibody by the transcription of the present antibody gene, or can express the present CAR by the transcription of mRNA of the present CAR gene. In the case of introducing a "vector comprising the present antibody gene" as the present vector, a yeast, a mammalian cell, an insect cell, or a plant cell given below can be used as the host cell. In the case of introducing a "vector comprising the present CAR gene" as the present vector, the immunocompetent cell described above can be used as the host cell.

In the case of using a yeast (e.g., *Saccharomyces cerevisiae* and *Schizosaccharomyces pombe*) as the host cell, examples of the present vector can include a vector such as YEP13 (ATCC37115), YEp24 (ATCC37051), and YCp50 (ATCC37419), and a vector derived from the vector. Examples of the promoter can include glycolysis gene (e.g., hexose kinase gene) promoter, PHO5 promoter, PGK promoter, GAP promoter, ADH promoter, gal1 promoter, gal10 promoter, heat shock protein promoter, MFα1 promoter, and CUP1 promoter.

In the case of using a mammalian cell (e.g., a human-derived Namalwa cell, a monkey-derived COS cell, a Chinese hamster ovary-derived CHO cell, and a human- or mouse-derived T cell) as the host cell and using a vector comprising the antibody gene as the present vector, examples of the present vector can include a vector such as pcDNAI, pcDM8 (manufactured by Funakoshi Co., Ltd.), pAGE107 (Japanese unexamined Patent Application Publication No. 3-22979; and Cytotechnology, 3, 133, (1990)), pAS3-3 (Japanese unexamined Patent Application Publication No. 2-227075), pCDM8 (Nature, 329, 840, (1987)), pcDNAI/Amp (manufactured by Invitrogen Corp.), pREP4 (manufactured by Invitrogen Corp.), pAGE103 (J. Biochemistry, 101, 1307 (1987)), and pAGE210, and a vector derived from the vector. On the other hand, in the case of using a mammalian cell (e.g., the human-derived immunocompetent cell described above) as the host cell and using a vector comprising the CAR gene as the present vector, examples of the present vector can include a retrovirus vector such as a pMSGV vector (Tamada k et al., Clin Cancer Res 18: 6436-6445 (2002)) and a pMSCV vector (manufactured by Takara Bio Inc.), and a vector derived from the vector.

Examples of the promoter in the present vector can include cytomegalovirus (CMV) IE (immediate early) gene promoter, SV40 early promoter, retrovirus promoter, metallothionein promoter, heat shock promoter, SRα promoter, NFAT promoter, and HIF promoter.

In the case of using an insect cell (e.g., a Sf9 cell and a Sf21 cell which are *Spodoptera frugiperda* ovarian cells, and a High5 cell which is a *Trichoplusia ni* ovarian cell) as the host cell, examples of the present vector can include a transfer vector for use in recombinant baculovirus preparation methods, specifically, a vector such as pVL1392, pVL1393, and pBlueBacIII (all manufactured by Invitrogen Corp.), and a vector derived from the vector. Examples of the promoter can include polyhedrin promoter and p10 promoter.

In the case of using a plant cell (e.g., tobacco, potato, tomato, carrot, soybean, rapeseed, alfalfa, rice, wheat, and barley cells) as the host cell, examples of the expression vector can include a vector such as Ti plasmid and tobacco mosaic virus vector, and a vector derived from the vector. Examples of the promoter can include cauliflower mosaic virus (CaMV) 35S promoter and rice actin 1 promoter.

The present vector preferably further comprises the nucleotide sequences of an enhancer region and a ribosome binding site (RBS) for further enhancing gene expression efficiency, and further comprises a drug resistance gene (e.g., spectinomycin resistance gene, chloramphenicol resistance gene, tetracycline resistance gene, kanamycin resistance gene, ampicillin resistance gene, puromycin resistance gene, hygromycin resistance gene, blasticidin resistance gene, and geneticin resistance gene) appropriate for the type of the host cell for screening for the present host cell. The enhancer region is usually arranged upstream of the promoter, and RBS is usually arranged between the promoter and the present gene. The nucleotide sequence of the present antibody gene to be incorporated into the present vector may be subjected to the optimization of a codon sequence according to the host cell for expression. The present vector can be prepared by a method known in the art using a gene recombination technique.

The present host cell can be obtained by introducing the present vector to the host cell (transfecting the host cell therewith) by a method appropriate for the type of the host cell.

In the case of using the yeast described above as the host cell, the method for introducing the present vector to the yeast can be any method for introducing DNA to the yeast. Examples thereof can include a method such as electroporation (Methods Enzymol., 194, 182 (1990)), spheroplast method (Proc. Natl. Acad. Sci. U.S.A, 84, 1929 (1978)), and lithium acetate method (J. Bacteriology, 153, 163 (1983)).

In the case of using the mammalian cell described above as the host cell, the method for introducing the present vector to the mammalian cell can be any method for introducing DNA to the mammalian cell. Examples thereof can include a method such as electroporation (Cytotechnology, 3, 133 (1990)), calcium phosphate method (Japanese unexamined Patent Application Publication No. 2-227075), lipofection (Proc. Natl. Acad. Sci. U.S.A., 84, 7413 (1987)), and viral infection method, as mentioned above. Examples of such a viral infection method can include a method which involves transfecting a packaging cell such as a GP2-293 cell (manufactured by Takara Bio Inc.), a Plat-GP cell (manufactured by Cosmo Bio Co., Ltd.), a PG13 cell (ATCC CRL-10686), or a PA317 cell (ATCC CRL-9078) with a CAR expression vector (International Publication No. WO 2016/056228) and a packaging plasmid to prepare a recombinant virus, and infecting a T cell with the recombinant virus, as mentioned above.

In the case of using the insect cell described above as the host cell, examples of the method for introducing the present vector to the insect cell can include a method which involves cotransfecting the insect cell with the present vector (transfer vector) and baculovirus-derived genomic DNA to prepare a recombinant baculovirus, according to a method described in "Current Protocols in Molecular Biology", "Baculovirus Expression Vectors, A Laboratory Manual, W.H. Freeman and Company, New York (1992)", "Bio/Technology, 6, 47 (1988)", etc. Examples of such a cotransfection method can include a method such as calcium phosphate method (Japanese unexamined Patent Application Publication No. 2-227075) and lipofection (Proc. Natl. Acad. Sci. U.S.A., 84, 7413 (1987).

In the case of using the plant cell described above as the host cell, examples of the method for introducing the present vector to the plant cell can include a method such as a method using *Agrobacterium* (Japanese unexamined Patent Application Publication Nos. 59-140885 and 60-70080), electroporation (Japanese unexamined Patent Application Publication No. 60-251887), and a method using a particle gun (gene gun) (Japanese Patent Nos. 2606856 and 2517813).

The present antibody can be obtained by culturing the present host cell obtained by the method mentioned above in a culture solution appropriate for the host cell.

A transgenic animal, such as a mouse, cattle, a goat, sheep, a chicken, or a pig, in which the present antibody gene (the present vector) has been incorporated is prepared by use of a transgenic animal preparation technique, and an antibody derived from the present antibody gene can also be produced in a large amount from the blood, milk, or the like of the transgenic animal.

Nonhuman animals (e.g., mice and rats) are immunized with a substance comprising a human-derived GPC3 polypeptide consisting of the amino acid sequence represented by SEQ ID NO: 155 (GPC3 polypeptide antigen). A phage library of scFv genes is prepared by a phage display method. The present scFv can be obtained by a biopanning method using the GPC3 polypeptide antigen and/or a cell line expressing the GPC3 polypeptide antigen (preferably a cell line expressing no endogenous GPC3), and further, preferably, a competitor C-terminal polypeptide of GPC3 consisting of the amino acid sequence represented by SEQ ID NO: 159. From the nonhuman animals thus immunized with the antigen, antibody-producing hybridomas are prepared by use of a cell fusion technique. A culture supernatant containing the present antibody can also be obtained through screening by ELISA using a plate in which the antigen has been immobilized on a solid phase. The present antibody can be separated and purified from the culture supernatant by use of an antibody purification technique known in the art.

The present detection method can be any method comprising the step of detecting GPC3 localized on a cell membrane (anchored on a cell membrane) in a sample (e.g., blood, a tissue, and urine) using the present antibody. Specific examples of the detection method can include immunofluorescent staining, Western blotting, and ELISA using the present antibody.

The present kit for detection is a kit comprising the present antibody or a labeled form thereof and is limited by the purpose of "detecting GPC3". The kit usually comprises components generally used in this kind of kit, for example, a carrier, a pH buffering agent, and a stabilizer as well as an attached document such as a manual and an instruction for detecting GPC3.

The organism species of GPC3 to be detected in the present detection method or the present kit for detection may be a nonhuman animal such as a mouse or a rat and is usually a human.

Examples of the labeling material for the labeled form of the present antibody can include: an enzyme such as peroxidase (e.g., horseradish peroxidase [HRP]), alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase and acetylcholinesterase; a fluorescent material such as fluorescein isothiocyanate, phycobiliprotein, rare earth metal chelates, dansyl chloride and tetramethylrhodamine isothiocyanate; a fluorescence protein such as green fluorescence protein (GFP), cyan fluorescence protein (CFP), blue fluorescence protein (BFP), yellow fluorescence protein (YFP), red fluorescence protein (RFP) and luciferase; a radioisotope such as 3H, $^{14}$C, $^{125}$I and $^{131}$I; biotin; avidin; and a chemiluminescence material.

References, such as scientific literatures, patents, and patent applications, cited herein are incorporated herein by reference in their entirety to the same extent as if each individual reference was specifically described. The present application claims the priority based on Japanese Patent Application No. 2017-001732 (filed on Jan. 10, 2017), the contents of which are incorporated herein by reference in their entirety.

Hereinafter, the present invention will be described more specifically with reference to Examples. However, the technical scope of the present invention is not limited by these examples.

Example 1

1. Preparation of Novel Anti-GPC3 Antibody Recognizing N-Terminal Polypeptide of Human GPC3
[Summary]

SKG/Jcl mice were used as animals to be immunized for preparing an anti-human GPC3 antibody, and full-length human GPC3 protein was used as an immunizing antigen. The SKG/Jcl mice were autoimmune disease model mice that spontaneously develop rheumatoid arthritis and are known to produce antibodies in response even to self-components depending on aging or a rearing environment. Meanwhile, GPC3 is highly homologous between humans and mice and is usually less likely to cause antibody production even by the immunization of normal mice. Therefore, the SKG/Jcl mice were used as animals to be immunized. A scFv phage library was prepared from cDNA derived from B cells of the mice immunized with GPC3, and an anti-human GPC3 antibody was isolated by the application of the phage display method.

Although the antiserum of immunized mice contains many types of antibodies, it is necessary to select mice producing antibodies having specificity for the N-terminal polypeptide of GPC3 by excluding mice producing antibodies low specific for GPC3 or antibodies recognizing the C-terminal polypeptide of GPC3. Accordingly, mouse individuals that exhibited the production of an antibody specifically binding to the N-terminal polypeptide of GPC3 were selected by use of ELISA and FCM. Specifically, cDNA was synthesized by reverse transcription reaction from total RNA of the B cells derived from the immunized mice, and antibody genes were amplified to prepare an antibody gene library. A scFv phage library was constructed from the antibody gene library, and *E. coli* was infected with the library so that *E. coli* expressed scFv, followed by biopanning using recombinant GPC3, the GPC3-expressing cell line, and the C-terminal polypeptide of GPC3 to enrich phages expressing the target scFv, i.e., an antibody against the N-terminal polypeptide of GPC3. In order to further analyze the obtained scFv for binding specificity for GPC3 in cells, i.e., GPC3 localized on (bound to) a cell membrane (membrane-bound GPC3) via a GPI (glycosylphosphatidylinositol) anchor, verification was made by use of cell based-ELISA and FCM. Furthermore, the nucleotide sequences of H chain and L chain variable regions of clones having binding specificity were sequenced, and the nucleotide sequences of the anti-GPC3 antibodies produced by the B cells derived from the immunized mice were determined on the basis of these sequences. Finally, the mammalian display method which involved expressing the N-terminal polypeptide fragment and the C-terminal polypeptide fragment of GPC3 on cell surface was used to confirm that the epitope for the scFv was the N-terminal polypeptide fragment of GPC3. Hereinafter, detailed methods and results will be shown.

1-1 Material and Method

[Cell Culture]

A JHH7 cell line, a HepG2 cell line, and a SK-Hep-1 cell line forced to express full-length human GPC3 (hereinafter, also referred to as a "GPC3-expressing cell line") were used as human GPC3-expressing cells to perform the biopanning and screening of an anti-GPC3 antibody. The JHH7 cell line is a GPC3-expressing cell line derived from hepatocellular carcinoma, and the cells constitutively express GPC3 bound to a cell membrane (membrane-bound GPC3) via a GPI (glycosylphosphatidylinositol) anchor. On the other hand, the HepG2 cell line is a GPC3-expressing cell line derived from hepatocellular carcinoma, as in the JHH7 cell line, but is a cell line in which the expression of secretory GPC3 that is not bound to a cell membrane is dominant over membrane-bound GPC3. The Sk-Hep-1 cell line is a hepatocellular carcinoma-derived cell line expressing no GPC3. Hence, a cell line expressing only membrane-bound full-length GPC3 or membrane-bound GPC3 having a partial length deficient in a portion of exons can be prepared by forced expression.

The culture of 4 types of cell lines (JHH7 cell line, HepG2 cell line, GPC3-expressing cell line, and human embryonic kidney epithelium-derived 293T cell line) was performed under conditions of 37° C. and 5% $CO_2$ in a DMEM culture solution (manufactured by Sigma-Aldrich Co. LLC) containing 10% FBS (manufactured by Gibco/Thermo Fisher Scientific Inc.) and 1% penicillin-streptomycin (manufactured by Gibco/Thermo Fisher Scientific Inc.) (hereinafter, simply referred to as a "DMEM culture solution"). The culture of a CHO-K1 cell line was performed under conditions of 37° C. and 5% $CO_2$ in a Ham's F12 culture solution (manufactured by Sigma-Aldrich Co. LLC) containing 10% FBS (manufactured by Gibco/Thermo Fisher Scientific Inc.).

[Immunizing Antigen]

C-terminally 6×His-tagged recombinant GPC3 (manufactured by R & D Systems Inc.) was adjusted to 0.1 mg/mL with PBS and mixed with an artificial adjuvant TiterMax Gold (manufactured by TiterMax USA, Inc.) or CFA (Freund's Adjuvant Complete) (F5881, manufactured by Sigma-Aldrich Co. LLC) in equal amounts to prepare an emulsion, which was then used as an initial immunizing antigen. Recombinant GPC3 was adjusted to a concentration from 10 to 100 μg/mL with PBS and used as the second or later immunizing antigens.

[Preparation of GPC3-Expressing Cell Line]

A gene encoding full-length human GPC3 consisting of the amino acid sequence represented by SEQ ID NO: 157 (full-length human GPC3 gene consisting of the nucleotide sequence represented by SEQ ID NO: 160) was inserted to a pcDNA3.1 vector (manufactured by Thermo Fisher Scientific Inc.) to prepare a GPC3 expression vector. A SK-Hep-1 cell line was transfected with the GPC3 expression vector according to a standard method and then cultured in a DMEM culture solution containing G418 (manufactured by Roche Diagnostics K.K.) to establish a SK-Hep-1 cell line stably expressing full-length GPC3 (GPC3-expressing cell line).

[Immunization of Mouse]

SKG/Jcl mice (CLEA Japan, Inc., 8-week-old female, SPF) were used as animals to be immunized, and immunized through footpads with recombinant GPC3 a total of 4 times on 1-week intervals. On 5 weeks from the start of immunization, blood was collected, and serum was prepared according to a standard method and used as a specimen for the confirmation of an antibody titer.

[Serum Antibody Titer of Antiserum Using ELISA]

In order to confirm the response of the immunized mice to produce an anti-GPC3 antibody, a serum antibody titer was measured by use of antigen-immobilized ELISA. 0.5 or 2 μg/mL recombinant GPC3 was added at 50 μL/well to a 96-well microplate (manufactured by Nalge Nunc International), and the plate was incubated at room temperature for 1 hour or at 4° C. for 12 hours. Then, 2% Block ACE (manufactured by DS Pharma Biomedical Co., Ltd.) was added at 200 μL/well to perform blocking treatment. The serum derived from the GPC3-immunized mice was serially diluted from 100-fold to 16500-fold with 0.1% Block ACE/PBS solution. Each diluted serum sample was added at 50 μL/well, and the plate was incubated at room temperature for 2 hours to perform antigen-antibody reaction treatment. After washing of the wells with a Tween 20-containing PBS (PBST) solution, goat anti-mouse IgG (manufactured by Jackson ImmunoResearch Laboratories Inc.) conjugated with 2 μg/mL peroxidase was added thereto, and the plate was incubated at room temperature for 2 hours to perform secondary antibody reaction treatment. After washing of the well five times with a PBST solution, moisture was removed, and a TMB substrate (manufactured by Thermo Fisher Scientific Inc.) was then added at 50 μL/well to perform color reaction. 15 minutes later, the color reaction was terminated by the addition of 0.18 M sulfuric acid at 50 μL/well, followed by the measurement of absorbance at 450 nm and 540 nm using a plate reader (manufactured by Bio-Rad Laboratories, Inc.). Quantification was performed using a corrected value obtained by subtracting the measurement value of 540 nm from the measurement value of 450 nm.

[Specificity of Antibody in Antiserum Using FCM]

In order to further confirm the specific binding activity of the antiserum against membrane-bound GPC3 as to the immunized mice, the mouse serum diluted 100-fold and $5 \times 10^3$ cells of the GPC3-expressing cell line were mixed and incubated for 30 minutes on ice. A FACS buffer (1% BSA/PBS solution) was added thereto, and the mixture was centrifuged to remove a supernatant. Then, 100 μL of 1 μg/mL goat anti-mouse IgG (H+L) Alexa Fluor 488 (manufactured by Thermo Fisher Scientific Inc.) was added as a secondary antibody, and the mixture was incubated for 30 minutes on ice to perform secondary antibody reaction treatment. The detection of Alexa Fluor 488 and the measurement of a fluorescence level were performed using a flow cytometer (FACSCanto) (manufactured by BD Biosciences).

[Preparation of scFv Phage Library]

B cells-derived total RNA was extracted according to a standard method as to the mice shown to produce an antibody binding to membrane-bound GPC3 by the method described above in the section [Flow cytometer]. RT-PCR with the total RNA as a template was performed according to a standard method to prepare cDNA. Antibody H chain and L chain variable region genes were amplified by PCR.

A nucleotide sequence encoding a fusion protein of scFv having the H chain and L chain variable regions linked via a flexible linker, and coat protein g3p (cp3) of fibrous bacteriophage M13 was inserted to the multicloning site of a pTZ19R phagemid vector to prepare a scFv expression vector. The scFv library size was calculated from the transformation efficiency of an E. coli DH12S strain (manufactured by Invitrogen Corp.). The transformed DH12S strain was infected with a helper phage M13K07 (manufactured by Invitrogen Corp.) to prepare a phage library expressing scFv.

[Biopanning and Cloning of Phage scFv]

The biopanning of phage scFv using a combination of recombinant GPC3 immobilized on Dynabeads His-Tag Isolation & Pulldown magnetic beads (manufactured by VERITAS Corp.) via 6×His tag, and the GPC3-expressing cell line as a bait was performed according to the method described in a document such as "J Mol Biol. 1991 Dec. 5; 222 (3): 581-97", "J Med Virol. 2007 June; 79 (6): 852-62", "Proc Natl Acad Sci USA. 2008 May 20; 105 (20): 7287-92", or "JOURNAL OF VIROLOGY, April 2004, p. 3325-3332 Vol. 78, No. 7". In each round (step) of biopanning consisting of types of series (A to E series) (see FIG. 1), an aliquot of polyclonal phage antibodies was sampled. In order to confirm the binding specificity of scFv, antigen-immobilized ELISA was performed according to the method described above in the section [Serum antibody titer of antiserum using ELISA] (method using the culture supernatant of E. coli containing a phage instead of the serum), while cell-based ELISA was performed according to the method described below in the section [Screening of scFv by cell-based ELISA]. Each step of this biopanning was devised so as not to select a scFv phage binding to the same portion as the C-terminal epitope of GPC3 recognized by existing antibodies, by binding in advance the existing anti-GPC3 antibodies GC33 (manufactured by Chugai Pharmaceutical Co., Ltd.) and GC199 (manufactured by Chugai Pharmaceutical Co., Ltd.) to the bait. Specifically, this competition method enables selective panning of a novel antibody recognizing a GPC3 epitope different from that for the existing anti-GPC3 antibodies. E. coli DH12S was transformed with the phages enriched by biopanning and inoculated to an LB agarose agar medium to separate single colonies. The E. coli was further cultured in a small-scale LB liquid medium, followed by the extraction and purification of plasmids. The purified plasmids were subjected to DNA sequencing to determine the nucleotide sequences of scFv H chain and L chain variable regions.

[Screening of scFv by FCM]

100 µL of the culture supernatant in which scFv phages were secreted was added to a GPC3-expressing cell line ($5\times10^5$ cells per sample) and mixed therewith, and the mixture was then incubated for 30 minutes on ice. A FACS buffer (1% BSA/PBS solution) was added thereto, and the mixture was centrifuged and washed. Then, 1 µg/mL anti-mouse antibody-Alexa 488 (manufactured by Thermo Fisher Scientific Inc.) was added thereto as a secondary antibody, and the mixture was incubated for 30 minutes on ice. Then, the fluorescent staining of the cells was measured using a flow cytometer (FACSCanto, manufactured by BD Biosciences).

[Screening of scFv by Cell-Based ELISA]

After removal of a DMEM culture solution from a 96-well microplate in which $2\times10^3$ GPC3-expressing cells were attached per well, 2% BSA-PBS solution was added for the purpose of preventing the nonspecific binding of scFv to the cells or the plate, and the plate was incubated for minutes on ice. Then, 100 µL of the culture supernatant of E. coli in which scFv phages were secreted was added to each well, and the plate was incubated for 45 minutes on ice. Then, 5 µg/mL rabbit anti-cp3 antibody (manufactured by Medical & Biological Laboratories Co., Ltd.) against cp3 fused on the C-terminal side of scFv was added at 100 µL per well, and the plate was further incubated for 45 minutes on ice. A HRP-labeled anti-rabbit IgG antibody (manufactured by Medical & Biological Laboratories Co., Ltd.) diluted 5000-fold was added at 100 µL per well as a tertiary antibody for anti-cp3 antibody detection, and the plate was incubated for 45 minutes on ice. Then, o-phenylenediamine (OPD) and hydrogen peroxide were added as substrates of HRP for color development. Quantification was performed using a numeric value obtained by subtracting absorbance at 620 nm as a background from absorbance at 492 nm. When cell-based ELISA was carried out using an antibody already converted to an IgG type antibody, not scFv, a HRP-labeled anti-mouse IgG antibody (manufactured by Medical & Biological Laboratories Co., Ltd.) diluted 2000-fold was used as a secondary antibody for the detection of the IgG type antibody instead of the anti-cp3 antibody and the HRP-labeled anti-rabbit IgG antibody among the conditions described above.

[Determination of Variable Region Gene Sequences of scFv]

The variable region gene sequences of phage scFv binding to membrane-bound GPC3 were decoded in a sequencer (CEQ2000XL, manufactured by Beckman Coulter, Inc.) using a T7 primer (primer consisting of the nucleotide sequence represented by SEQ ID NO: 176), which is a universal primer, and a cp3R primer (primer consisting of the nucleotide sequence represented by SEQ ID NO: 177) as a forward primer for H chain V region ($V_H$) decoding and a reverse primer for L chain V region ($V_L$) decoding, respectively.

[Preparation of Cell Line for Use in Antibody Epitope Mapping]

In order to identify an epitope for the cloned scFv, the mammalian display method was applied. A gene consisting of human GPC3 exons 1 to 7 and encoding a GPC3 N-terminal fragment (polypeptide consisting of the amino acid sequence represented by SEQ ID NO: 155), and a gene consisting of human GPC3 exons 8 and 9 and encoding a GPC3 C-terminal fragment (polypeptide consisting of the amino acid sequence represented by SEQ ID NO: 156) were amplified by PCR and each inserted to the multicloning site (MSC) of a pDisplay expression vector (manufactured by Thermo Fisher Scientific Inc.). The pDisplay expression vector is an expression vector capable of fusing a transmembrane domain of platelet-derived growth factor receptor (PDGFR) to the C terminus of the target protein and displaying the fusion product on the cell surface of arbitrary mammalian cells. Also, the pDisplay expression vector is constituted so as to add a HA tag to the N terminus of the target protein and to add a myc tag to the C terminus of the PDGFR. The pDisplay expression vector for expressing the GPC3 N-terminal fragment or the GPC3 C-terminal fragment was gene-transferred to a SK-Hep-cell line or a 293T cell line, and a cell line expressing the GPC3 N-terminal fragment or the GPC3 C-terminal fragment on the cell surface (GPC3 N-terminal fragment-expressing cell line and GPC3 C-terminal fragment-expressing cell line) was isolated and used in the epitope mapping of scFv.

[Antibody Epitope Mapping by FCM]

The GPC3 N-terminal fragment-expressing cell line, the GPC3 C-terminal fragment-expressing cell line, and the GPC3-expressing cell line ($5\times10^3$ cells each per sample) were each mixed with 100 µL of the culture supernatant in which scFv phages were secreted, and the mixture was incubated for 30 minutes on ice. A FACS buffer (1% BSA/PBS solution) was added thereto, and the mixture was centrifuged and washed. Then, 1 µg/mL anti-mouse antibody-Alexa 488 (manufactured by Thermo Fisher Scientific Inc.) was added thereto as a secondary antibody, and the mixture was incubated for 30 minutes on ice. Then, the fluorescent staining of the cells was measured using a flow cytometer (FACSCanto, manufactured by BD Biosciences).

[Construction of Recombinant IgG Expression Vector]

In order to convert scFv to IgG, an expression vector of Mammalian PowerExpress system (manufactured by Toyobo Co., Ltd.) was used. A nucleotide sequence encoding a fusion protein of the H chain variable region of scFv and a mouse IgG2a H chain-derived constant region was inserted to MSC of a pEH1.1 vector (pEH1.1-H). Also, a nucleotide sequence encoding a fusion protein of the L chain variable region of scFv and a mouse IgG2a L chain-derived constant region was inserted to MSC of a pELX2.2 vector (pEH2.2-L). Then, a polynucleotide fragment from EF1α promoter to the L chain gene was excised from pEH2.2-L with restriction enzymes (BglII and SalI) and ligated with pEH1.1-H treated with restriction enzymes (BglII and SalI) to construct a vector for coexpressing the antibody H chain and L chain.

[Expression of Recombinant IgG]

32.6 µg of the antibody H chain and L chain coexpression vector prepared by the method described above in [Construction of recombinant IgG expression vector] was diluted with 1.6 mL of opti-MEM (manufactured by Gibco/Thermo Fisher Scientific Inc.) and mixed with 65 µL of Transficient Transfection Reagent (manufactured by Medical & Biological Laboratories Co., Ltd.) diluted with 1.6 mL of opti-MEM, and the mixture was incubated at room temperature for 10 minutes. Then, the mixture was mixed with CHO-K1 cells ($1\times10^7$ cells) suspended in 10 mL of a DMEM culture solution, followed by culture. 4 hours later, a serum-free medium (Free Style expression CHO media [manufactured by Gibco/Thermo Fisher Scientific Inc.]) was added thereto, and the mixture was further cultured for 4 to 6 days to recover a culture supernatant containing a recombinant antibody.

[Affinity Purification of Antibody]

An empty column (manufactured by Bio-Rad Laboratories, Inc.) was packed with Protein G Sepharose 4 Fast Flow (manufactured by GE Healthcare Japan Corp.) or Bipo Resin Protein L (manufactured by Protein Express) at 1 mL bed volume. Then, the column resin was washed with PBS in an amount of 10 times the bed volume. The culture supernatant filtered through a 0.22 micron filter was added to the column so that the antibody was entrapped to protein G or protein L within the column. Then, the column was washed with PBS in an amount of 10 times the bed volume to wash off nonspecifically adsorbed contaminants. The antibody was eluted using a 100 mM glycine-HCl (pH 2.7) solution, and pH of the eluate was neutralized with 1 M Tris-HCl (pH 8.5). Absorbance at 280 nm was measured with an absorbance meter nanoDrop (manufactured by Thermo Fisher Scientific Inc.), and the antibody concentration was calculated. Expression vectors were also designed and prepared by the same method as above as to the GC33 antibody and the GC199 antibody used as competitive antibodies.

1-2 Results

[Antiserum Evaluation of Immunized Mouse]

Blood was collected from SKG/Jcl mice immunized four times with recombinant GPC3, and the production of an antibody against GPC3 in serum was confirmed. As a result, an antibody having binding activity against GPC3 was detected by experiments of ELIS on recombinant GPC3 and FCM on GPC3-expressing cells. Two mice having a particularly high antibody titer (individual Nos. 1413 #2 and 1413 #3) among the mice were used as sources for the preparation of an antibody library.

[Construction of Phage Library]

The number of members in a scFv library estimated by calculation from transformation efficiency was $5.8\times10^7$ for mouse 1413 #2 and $4.3\times10^8$ for mouse 1413 #3. The immunoglobulin library prepared in this Example was a library prepared from the mice found to produce antibodies in response to the target antigen by immunization with the antigen GPC3. Therefore, a feature of this library is the high possibility of containing the target antibody gene even if the library size is small. Another advantageous feature thereof is that the library contains an antibody that forms a correct conformation in vivo, as compared with a random synthetic antibody library.

[Classification of Clone by Sequence Analysis of Monoclonal scFv]

The DNA sequence analysis of picked up monoclonal scFv was conducted to perform clone classification excluding overlap. As a result, candidate clones were identified as 7 types from D series of the mouse 1413 #2 library, 5 types from E series thereof, 3 types from D series of the mouse 1413 #3 library, and 9 types from E series thereof. The nucleotide sequences of heavy chain and light chain variable regions of these candidate clones were analyzed to exclude overlapping identical clones. As a result, a total of 18 types of scFv clones, i.e., 9 types of scFv clones derived from the mouse 1413 #2 library, and 9 types of scFv clones derived from the mouse 1413 #3 library, were identified.

[Epitope Mapping Analysis of Anti-GPC3 scFv Clone]

Figure 2:
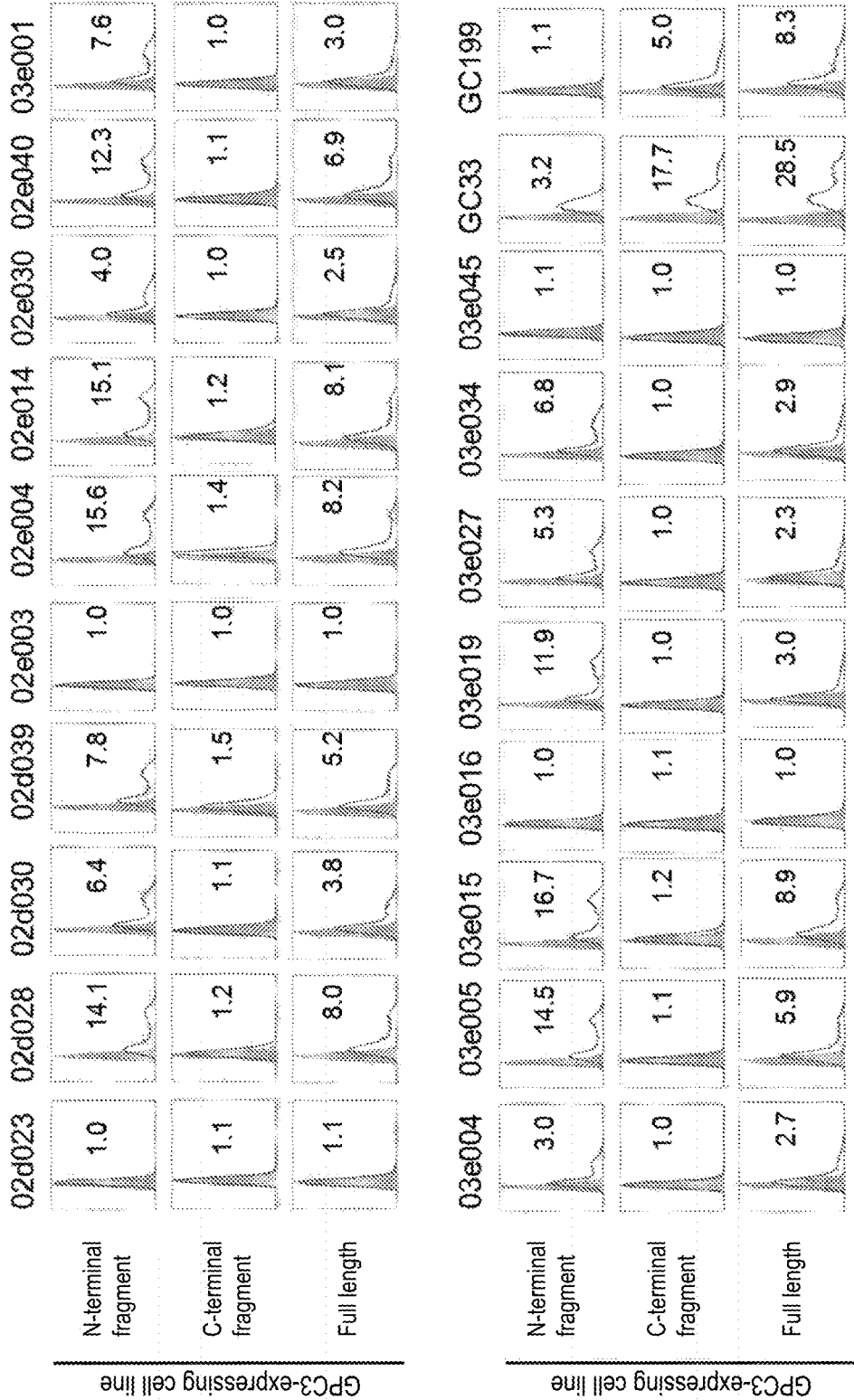
FIG. 2 is a diagram showing results of performing flow cytometry (FCM) using 18 types of anti-GPC3 scFv clones (TF1413-02d023, 02d028, 02d030, 02d039, 02e003, 02e004, 02e014, 02e030, 02e040, 03e001, 03e004, 03e005, 03e015, 03e016, 03e019, 03e027, 03e034, and 03e045) and existing anti-GPC3 antibodies (GC33 and GC199), and 3 types of cell lines (GPC3 N-terminal fragment-expressing cell line, GPC3 C-terminal fragment-expressing cell line, and GPC3 [full-length]-expressing cell line). The numeric values in the diagram are indicated by relative values when the fluorescence intensity of a cell line expressing no GPC3 (SK-Hep-1 cell line) was defined as 1 in FCM.

18 types of scFv clones identified according to the method described above in the section [Classification of clone by sequence analysis of monoclonal scFv] were used to analyze binding to each GPC3 by FCM using 3 types of cell lines (GPC3 N-terminal fragment-expressing cell line, GPC3 C-terminal fragment-expressing cell line, and GPC3-expressing cell line). As a result, among the 18 types of scFv clones, 14 types (TF1413-02d028, 02d030, 02d039, 02e004, 02e014, 02e030, 02e040, 03e001, 03e004, 03e005, 03e015, 03e019, 03e027, and 03e034) bound to full-length GPC3 and the GPC3 N-terminal fragment (polypeptide consisting of the amino acid sequence represented by SEQ ID NO: 155), but did not bind to the GPC3 C-terminal fragment (polypeptide consisting of the amino acid sequence represented by SEQ ID NO: 156) (see FIG. 2). On the other hand, the existing anti-GPC3 antibodies GC33 (manufactured by Chugai Pharmaceutical Co., Ltd.) and GC199 (manufactured by Chugai Pharmaceutical Co., Ltd.) bound to full-length GPC3 and the GPC3 C-terminal fragment, but did not bind to the GPC3 N-terminal fragment.

From these results, the 14 types of novel scFv clones described above recognizing a GPC3 N-terminal epitope different from a GPC3 C-terminal epitope for the existing anti-GPC3 antibodies (GC33 and GC199) were identified.

Among the 14 types of scFv clones thus identified, top 11 scFv clones (TF1413-02d028, 02d039, 02e004, 02e014, 02e030, 02e040, 03e001, 03e004, 03e005, 03e015, and 03e034) having particularly high binding strength were selected. Table 1 shows the correspondence of SEQ ID NOs to the H chain and L chain V regions of these 11 types of scFv clones. Table 2 shows the correspondence of SEQ ID NOs to the H chain CDR1 to CDR3 of these 11 types of scFv clones. Table 3 shows the correspondence of SEQ ID NOs to the L chain CDR1 to CDR3 of these 11 types of scFv clones.

TABLE 1

| scFv clone name and V region | | SEQ ID NO |
|---|---|---|
| TF1413-02d028 | H chain V region | 7 |
| TF1413-02d039 | H chain V region | 17 |
| TF1413-02e004 | H chain V region | 27 |
| TF1413-02e014 | H chain V region | 37 |
| TF1413-02e030 | H chain V region | 47 |
| TF1413-02e040 | H chain V region | 57 |
| TF1413-03e001 | H chain V region | 67 |
| TF1413-03e004 | H chain V region | 77 |
| TF1413-03e005 | H chain V region | 87 |
| TF1413-03e015 | H chain V region | 97 |
| TF1413-03e034 | H chain V region | 107 |
| TF1413-02d028 | L chain V region | 8 |
| TF1413-02d039 | L chain V region | 18 |
| TF1413-02e004 | L chain V region | 28 |
| TF1413-02e014 | L chain V region | 38 |
| TF1413-02e030 | L chain V region | 48 |
| TF1413-02e040 | L chain V region | 58 |
| TF1413-03e001 | L chain V region | 68 |
| TF1413-03e004 | L chain V region | 78 |
| TF1413-03e005 | L chain V region | 88 |
| TF1413-03e015 | L chain V region | 98 |
| TF1413-03e034 | L chain V region | 108 |

TABLE 2

| Clone name and CDR | | SEQ ID NO |
|---|---|---|
| TF1413-02d028 | H chain CDR1 | 1 |
| | H chain CDR2 | 2 |
| | H chain CDR3 | 3 |
| TF1413-02d039 | H chain CDR1 | 11 |
| | H chain CDR2 | 12 |
| | H chain CDR3 | 13 |
| TF1413-02e004 | H chain CDR1 | 21 |
| | H chain CDR2 | 22 |
| | H chain CDR3 | 23 |
| TF1413-02e014 | H chain CDR1 | 31 |
| | H chain CDR2 | 32 |
| | H chain CDR3 | 33 |
| TF1413-02e030 | H chain CDR1 | 41 |
| | H chain CDR2 | 42 |
| | H chain CDR3 | 43 |
| TF1413-02e040 | H chain CDR1 | 51 |
| | H chain CDR2 | 52 |
| | H chain CDR3 | 53 |
| TF1413-03e001 | H chain CDR1 | 61 |
| | H chain CDR2 | 62 |
| | H chain CDR3 | 63 |
| TF1413-03e004 | H chain CDR1 | 71 |
| | H chain CDR2 | 72 |
| | H chain CDR3 | 73 |
| TF1413-03e005 | H chain CDR1 | 81 |
| | H chain CDR2 | 82 |
| | H chain CDR3 | 83 |
| TF1413-03e015 | H chain CDR1 | 91 |
| | H chain CDR2 | 92 |
| | H chain CDR3 | 93 |
| TF1413-03e034 | H chain CDR1 | 101 |
| | H chain CDR2 | 102 |
| | H chain CDR3 | 103 |

TABLE 3

| Clone name and CDR | | SEQ ID NO |
|---|---|---|
| TF1413-02d028 | L chain CDR1 | 4 |
| | L chain CDR2 | 5 |
| | L chain CDR3 | 6 |
| TF1413-02d039 | L chain CDR1 | 14 |
| | L chain CDR2 | 15 |
| | L chain CDR3 | 16 |
| TF1413-02e004 | L chain CDR1 | 24 |
| | L chain CDR2 | 25 |
| | L chain CDR3 | 26 |
| TF1413-02e014 | L chain CDR1 | 34 |
| | L chain CDR2 | 35 |
| | L chain CDR3 | 36 |
| TF1413-02e030 | L chain CDR1 | 44 |
| | L chain CDR2 | 45 |
| | L chain CDR3 | 46 |
| TF1413-02e040 | L chain CDR1 | 54 |
| | L chain CDR2 | 55 |
| | L chain CDR3 | 56 |
| TF1413-03e001 | L chain CDR1 | 64 |
| | L chain CDR2 | 65 |
| | L chain CDR3 | 66 |
| TF1413-03e004 | L chain CDR1 | 74 |
| | L chain CDR2 | 75 |
| | L chain CDR3 | 76 |
| TF1413-03e005 | L chain CDR1 | 84 |
| | L chain CDR2 | 85 |
| | L chain CDR3 | 86 |
| TF1413-03e015 | L chain CDR1 | 94 |
| | L chain CDR2 | 95 |
| | L chain CDR3 | 96 |
| TF1413-03e034 | L chain CDR1 | 104 |
| | L chain CDR2 | 105 |
| | L chain CDR3 | 106 |

[Conversion of Anti-GPC3 scFv Antibody to IgG and its Ability to Bind]

Figure 3:
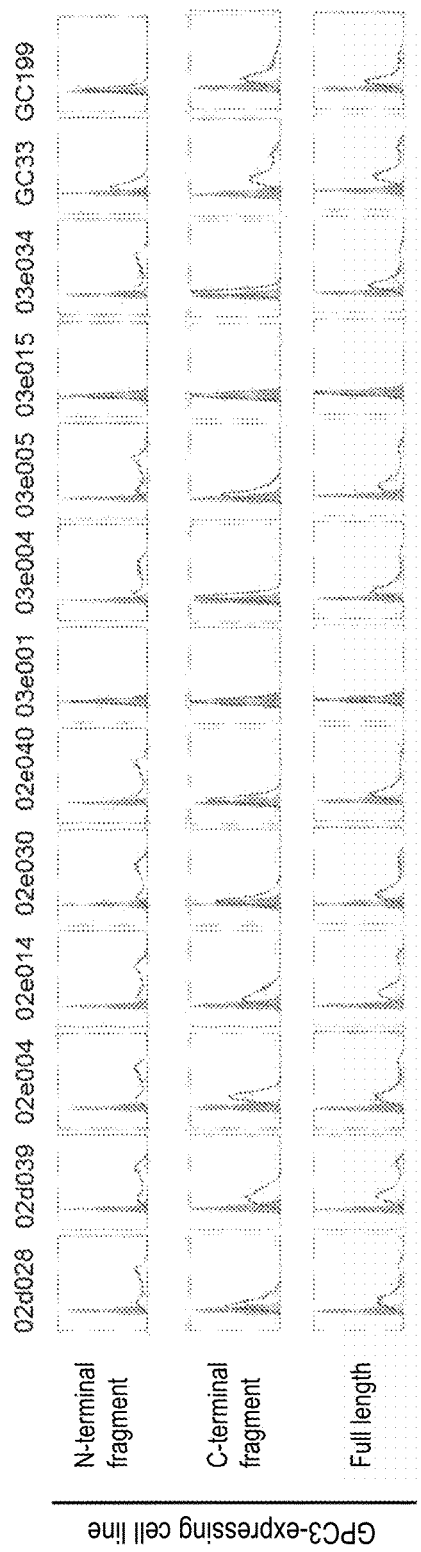
FIG. 3 is a diagram showing results of performing FCM using IgG antibodies prepared from 11 types of scFv clones (TF1413-02d028, 02d039, 02e004, 02e014, 02e030, 02e040, 03e001, 03e004, 03e005, 03e015, and 03e034) and existing anti-GPC3 antibodies (GC33 and GC199), and 3 types of cell lines (GPC3 N-terminal fragment-expressing cell line, GPC3 C-terminal fragment-expressing cell line, and GPC3 [full-length]-expressing cell line).

The H chain and L chain variable regions of the 11 types of scFv clones selected as described above were bound to mouse IgG constant regions, and full-length recombinant antibodies were expressed using a vector for recombinant IgG expression and affinity-purified. The ability of these IgG antibodies to bind to the GPC3 N-terminal fragment was analyzed using the GPC3 N-terminal fragment-expressing cell line. As a result, 9 types of IgG clones (TF1413-02d028, 02d039, 02e004, 02e014, 02e030, 02e040, 03e004, 03e005, and 03e034) maintained binding activity against the GPC3 N-terminal fragment, whereas the remaining two types of IgG clones (TF1413-03e001 and 03e015) lacked binding activity against the GPC3 N-terminal fragment (see FIG. 3). The 9 types of IgG clones described above did not bind to the GPC3 C-terminal fragment (see FIG. 3).

These results indicate that among the 11 types of scFv clones, 9 types (TF1413-02d028, 02d039, 02e004, 02e014, 02e030, 02e040, 03e004, 03e005, and 03e034) are convertible to IgG type. Table 4 shows the correspondence of SEQ ID NOs to the H chains and the L chains of the 11 types of IgG clones.

TABLE 4

| IgG clone name and region | | SEQ ID NO |
|---|---|---|
| TF1413-02d028 | H chain | 9 |
| TF1413-02d039 | H chain | 19 |
| TF1413-02e004 | H chain | 29 |
| TF1413-02e014 | H chain | 39 |
| TF1413-02e030 | H chain | 49 |
| TF1413-02e040 | H chain | 59 |
| TF1413-03e001 | H chain | 69 |
| TF1413-03e004 | H chain | 79 |
| TF1413-03e005 | H chain | 89 |
| TF1413-03e015 | H chain | 99 |
| TF1413-03e034 | H chain | 109 |
| TF1413-02d028 | L chain | 10 |

TABLE 4-continued

| IgG clone name and region | | SEQ ID NO |
|---|---|---|
| TF1413-02d039 | L chain | 20 |
| TF1413-02e004 | L chain | 30 |
| TF1413-02e014 | L chain | 40 |
| TF1413-02e030 | L chain | 50 |
| TF1413-02e040 | L chain | 60 |
| TF1413-03e001 | L chain | 70 |
| TF1413-03e004 | L chain | 80 |
| TF1413-03e005 | L chain | 90 |
| TF1413-03e015 | L chain | 100 |
| TF1413-03e034 | L chain | 110 |

Example 2

2. Binding Activity of Novel Anti-GPC3 Antibody Against GPC3 Treated with EDTA (Ethylenediaminetetraacetic Acid), Trypsin or Collagenase

[Preparation of Cell Treated with EDTA or Trypsin]

A SK-Hep-1 cell line forced to express GPC3 was cultured in two T-75 flasks. The culture supernatant of each flask was aspirated, and the flask was washed with 3 mL of PBS. Then, 3 mL of 0.02% EDTA/PBS solution (hereinafter, simply referred to as "EDTA") or 0.05% trypsin solution (hereinafter, simply referred to as "trypsin") was added to each flask. Each flask was incubated at 37° C. for 5 minutes (EDTA) or 2 minutes and 30 seconds (trypsin) to dissociate the cells from the flask. Then, 7 mL of a DMEM culture solution was added to each flask. After pipetting, the cell suspension was recovered into each 50 mL conical tube. Each flask was further washed with 10 mL of a DMEM culture solution. Then, the recovered washes were also recovered into the 50 mL conical tube containing each cell suspension, followed by centrifugation (1,500 rpm, 4° C., 4 min). After aspiration of the supernatant from each conical tube, 10 mL of a DMEM culture solution was added to the pellet, and the number of cells dissociated with EDTA or trypsin was counted.

The cells treated with EDTA or trypsin were adjusted to $2 \times 10^3$ cells/tube and subjected to FACS (EC800) analysis. The FACS analysis employed 3 types of antibodies (fluorescently APC-labeled anti-mouse IgG antibody [5 μg/tube; manufactured by BioLegend, Inc.], GC33 antibody [1.0 μg/tube; manufactured by Medical & Biological Laboratories Co., Ltd. Life Science], and scFv clone [TF1413-02d028] antibody described above [1.0 μg/tube]).

[Preparation of Cell Treated with Collagenase]

Figure 4:
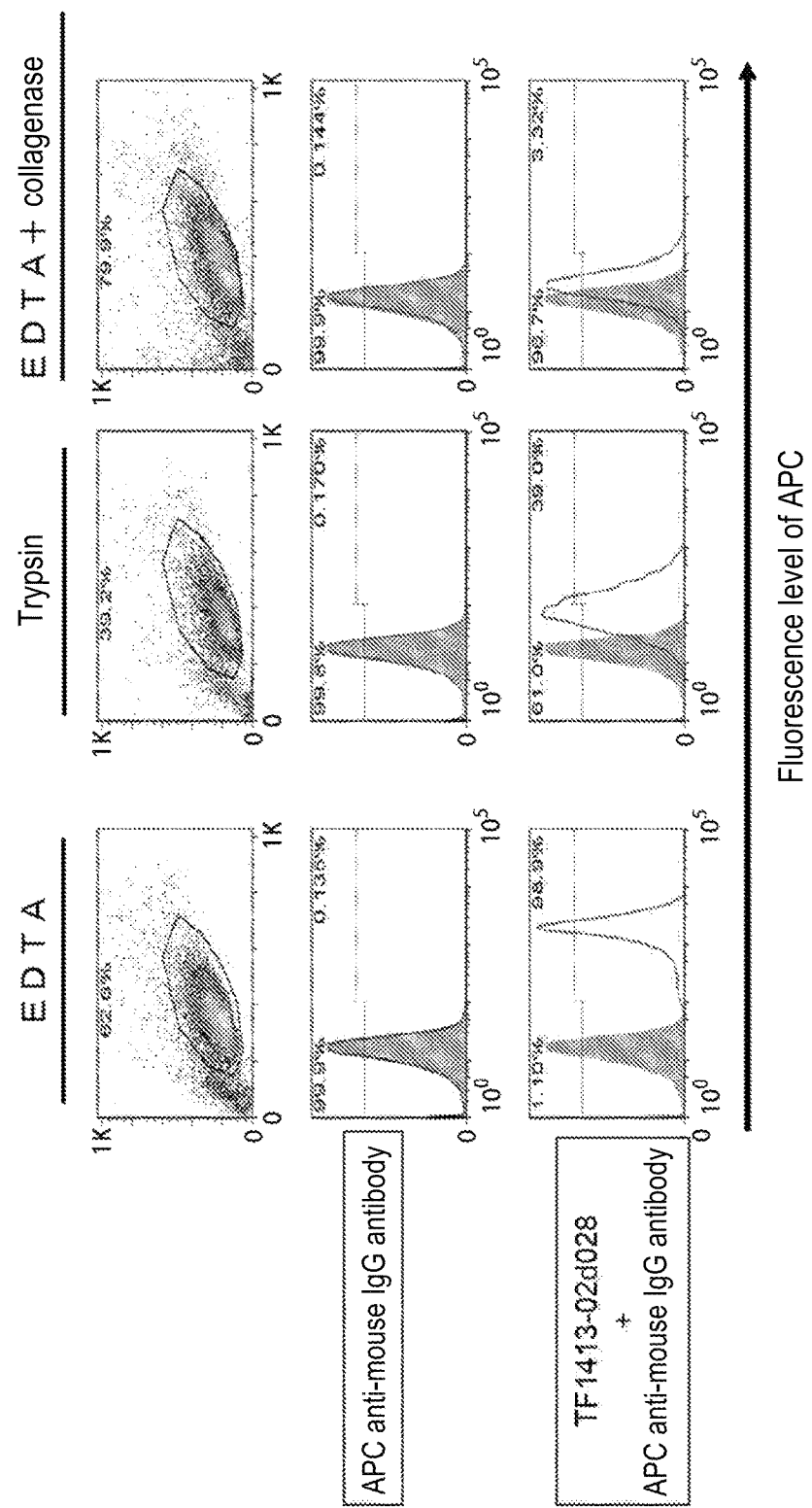
FIG. 4 is a diagram showing results of performing FACS (fluorescence activated cell sorting) using a GPC3-expressing cell line treated with 3 types of methods (EDTA, trypsin, and "EDTA+collagenase"), 3 types of antibody combinations (anti-mouse IgG antibody labeled with APC [hereinafter, also referred to as "APC ant-mouse IgG antibody"], and a combination of the APC anti-mouse IgG antibody and a scFv clone [TF1413-02d028] antibody).

$1 \times 10^6$ cells dissociated with EDTA as described above were placed in a 50 mL conical tube and centrifuged (1,500 rpm, 4° C., 4 min), and the supernatant was aspirated to prepare a cell mass (pellet). 5 mL of a collagenase P solution was added to the pellet, and the mixture was incubated at 37° C. for 30 minutes to prepare a cell suspension. Then, the cell suspension was passed through a 100 μm cell strainer while washed with 30 mL of a DMEM culture solution. The cell suspension was passed again through a 100 μm cell strainer and centrifuged (300 g, 4° C., 10 min), and the supernatant was aspirated. The pellet was washed by the addition of 20 mL of PBS and then centrifuged (300 g, 4° C., 5 min), and the supernatant was aspirated. The cells were suspended by the addition of 5 mL of a DMEM culture solution. Then, the number of cells was counted, and $2 \times 10^3$ cells/tube were analyzed by FACS (EC800). The FACS analysis employed 3 types of antibodies (fluorescently APC-labeled anti-mouse IgG antibody [5 μg/tube; manufactured by BioLegend, Inc.], GC33 antibody [1.0 μg/tube; manufactured by Medical & Biological Laboratories Co., Ltd. Life Science], and scFv clone [TF1413-02d028] antibody described above [1.0 μg/tube]), as in the cells treated with EDTA or trypsin. The results are shown in FIG. 4. In FIG. 4, the right peak on the abscissa represents that the GC33 antibody or the scFv clone [TF1413-02d028] antibody bound to the GPC3 protein.

[Results]

As shown in FIG. 4, the binding activity of the antibody of the present invention (TF1413-02d028) against the GPC3 protein treated with trypsin or collagenase was markedly decreased. These results indicate that the antibody of the present invention specifically recognizes the conformation of the GPC3 protein, suggesting that the antibody of the present invention has high specificity in vivo.

Example 3

3. Development of GPC3 CAR-T Cell Using Novel Anti-GPC3 Antibody

[Summary]

GPC3 is a cell surface molecule, the expression of which is not observed in human adult tissues except for placenta, but is observed in tissues of various cancers such as hepatocellular carcinoma, melanoma, ovarian clear cell adenocarcinoma, and lung squamous cell carcinoma. Thus, GPC3 is capable of serving as a target molecule in CAR-T cell therapy exploiting a chimeric antigen receptor (CAR). Accordingly, GPC3 CAR-T cells were prepared using 11 types of scFv clones prepared in Example 1 and analyzed for cancer cytotoxic activity and the ability to produce interferon γ (IFN-γ).

[Preparation of GPC3 CAR Vector]

scFv having a $V_H$-linker-$V_L$ sequence was designed as to 11 types of scFv clones (TF1413-02d028, 02d039, 02e004, 02e014, 02e030, 02e040, 03e001, 03e004, 03e005, 03e015, and 03e034) prepared in Example 1, on the basis of their respective amino acid sequences of $V_H$ and $V_L$ (see Table 5). The linker used consisted of 15 amino acid residues with 3 repeats of a polypeptide "GGGGS". A human immunoglobulin H chain-derived signal sequence consisting of the amino acid sequence represented by SEQ ID NO: 188 was added to the N terminus of $V_H$.

TABLE 5

SEQ ID NO: 165: TF1413-02d028 -derivedscFv

QVQLKESGPELEKPGASVKISCKASGYSFTGYNMNWVKQSNGKSLEWI

GNIDPYYGGTSYNQKFKGKATLTVDKSSSTAYMQLKSLTSEDSAVYYC

ARGDYRAYYFDYWGQGTTLTVS<u>GGGGSGGGGSGGGGS</u>DIQMTQSPKFM

ARGDYRAYYFDYWGQGTTLTVSGGGGSGGGGSGGGGSDIQMTQSPKFM

STSVGDRVSITCKASQNVRTAVAWYQQKPGQSPKALIYLASNRHTGVP

DRFTGSGSGTDFTLTISNVQSEDLADYFCLQHWNYPLTFGAGTKLELK

R

SEQ ID NO: 166: TF1413-02d039 -derived scFv

EVKLVESGGGLVKPGGSLKLSCAASGFAFSSYDMSWVRQTPEKRLEWV

AYISSGGGSTYYPDTVKGRFTISRDNAKNTLYLQMSSLKSEDTAMYYC

ARRGLRRAMDYWGQGTSVTVS<u>GGGGSGGGGSGGGGS</u>DVVMTQTPLSLPV

SLGDQASISCRSSQSLVHSNGNTYLHWYLQKPGQSPKLLIYKVSNRFS

GVPDRFSGSGSGTDFTLKISRVEAEDLGVYFCSQSTHVPLTFGAGTKL

ELKR

TABLE 5-continued

SEQ ID NO: 167: TF1413-02e004 -derived scFv
QVQLQQSGAELVKPGAPVKLSCKASGYTFTSYWMNWVKQRPGRGLEWI
GRIDPSDSETHYNQKFKDEATLTVDKSSSTAYIQLSSLTSEDSAVYYC
ARGYYAMDYWGQGTSVTVS GGGGSGGGGSGGGGS DIVLTQSPKFMSTS
VGDRVSITCKASQDVSTAVAWYQQKPGQSPKLLIYSASYRYTGVPDRF
TGSGSGTDFTFTISSVQAEDLAVYYCQQHYSTPTFGGGTKLEIKR SEQ ID NO: 168: TF1413-02e014 -derived scFv
QVQLKQSGAELVRSGASVKLSCTASGFNIKDYYMHWVKQRPEQGLEWI
GWIDPENGDTEYAPKFQGKATMTADTSSNTAYLQLSSLTSEDTAVYYC
NAGYYDYDGYAMDYWGQGTSVTVS GGGGSGGGGSGGGGS DIVLTQSPK
FMSTSVGDRVSITCKASQDVGTAVAWYQQKPGQSPKLLIYWASTRHTG
VPDRFTGSGSGTDFTLTISNVQSEDLADYFCQQYSSYPLTFGGGTKLE
IKR SEQ ID NO: 169: TF1413-02e030 -derived scFv
EVQLQQSGAELVRPGALVKLSCKASGFNIKDYYMHWVKQRPEQGLEWI
GWIDPENGNTIYDPKFQGKASITADTSSNTAYLQLSSLTSEDTAVYYC
AISTMITTLDYWGQGTTLTVS GGGGSGGGGSGGGGS DIQMTQSPSSLA
MSVGQKVTMSCKSSQSLLNSSNQKNYLAWYQQKPGQSPKLLVYFASTR
ESGVPDRFIGSGSGTDFTLTISSVQAEDLADYFCQQHYSTPLTFGAGT
KLELKR SEQ ID NO: 170: TF1413-02e040 -derived scFv
EVMLVESGPELVKPGASMKISCKASGYSFTGYTMNWVKQSHGKNLEWI
GLINPYNGGTSYNQNFKGKATLTVDKSSSTAYMELLSLTSEDSAVYYC
ARGYYGRFDYWGQGTTLTVS GGGGSGGGGSGGGGS DILLTQSPKFMST
SVGDRVSITCKASQNVRTAVAWYQQKPGQSPKALIYLASNRHTGVPDR
FTGSGSGTDFTLTISNVQSEDLADYFCLQHWNYPLTFGAGTKLELKR SEQ ID NO: 171: TF1413-03e001 -derived scFv
QVQLKQSGPELVKPGASVKISCKASGYSFTGYYMHWVKQSHVKSLEWI
GRINPYNGATSYNQNFKDKASLTVDKSSSTAYMELHSLTSEDSAVYYC
ARNYGYFDYWGQGTTLTVS GGGGSGGGGSGGGGS DIKMTQSPKFMSTS
VGDRVSVTCEASQNVDNNVVWYQQKPGQSPKALIYSASYRYSGVPDRF
TGSGSGTDFTLTISNVQSEDLAEYFCQQYNSYPLTFGAGTKLEIKR SEQ ID NO: 172: TF1413-03e004 -derived scFv
QVQLKQSGAELVKPGAPVKLSCKASGYTFTSYWMNWVKQRPGRGLEWI
GRIDPSDSETHYNQKFKDKATLTVDKSSSTAYIQLSSLTSEDSAVYYC
ARNYGYYGSNYWGQGTTLTVS GGGGSGGGGSGGGGS DIKMTQSPKFMS
TSVGDRVSVTCKASQNVGTNVAWYQQKPGQSPKALIYSASYRYSGVPD
RFTGSGSGTDFTLTISNVQSEDLAEYFCQQYNSYPLTFGAGTKLELKR SEQ ID NO: 173: TF1413-03e005 -derived scFv
QVQLKESGAELVRSGASVKLSCTASGFNIKDYYMHWVKQRPEQGLEWI
DPENGDTEYAPKFQGKATMTADTSSNTAYLQLSSLTSEDTAVYYCNAF
YYDYDGYAMDYWGQGTSVTVS GGGGSGGGGSGGGGS DVVMTQTPSSLS ASLGERVSLTCRASQEISGYLSWLQQKPDGTIKRLIYAASTLDSGVPK
RFSGSRSGSDYSLTISSLESEDFADYYCLQYASYPLTFGAGTKLELKR SEQ ID NO: 174: TF1413-03e015 -derived scFv
EVQLQQSGPELVKPGASMKISCKASGYSFTGYTMNWVKQSHGKNLEWI
GLINPYNGGTSYNQKFKGKATLTVDKSSSTAYMELLSLTSEDSAVYYC
ARGDYYPPYAMDYWGQGTSVTVS GGGGSGGGGSGGGGS DIVMSQSPKF
MSTSGDRVSVTCKASQNVGTNVAWYQQKPGQSPKPLIYSASYRYSGVP
DRFTGSGSGTDFTLTISNVQSEDLAEYFCQQYNRYPLTFGVGTKLEIK
R SEQ ID NO: 175: TF1413-03e034 -derived scFv
EVQLQQSGPELEKPGASVKISCKASGYSFTGYNMNWVKQSNGKSLEWI
GNIDPYYGGTSYNQKFKGKATLTVDKSSSTAYMQLKSLTSEDSAVYYC
ARGNYGYYAMDYWGQGTSVTVS GGGGSGGGGSGGGGS DIVMSQSPKFM
STSVGDRVSITCKASQNVRTAVAWYQQKPGQSPKALIYLASNRHTGVP
DRFTGSGSGTDFTLTISNVQSEDLADYFCLQHWNYPLTFGAGTKLELK
R In the tables, the linker is boxed in a double line, $V_H$ is underlined with a single line, and $V_L$ is underlined with a double line.

A nucleotide sequence encoding each anti-GPC3 scFv of Table 5 was synthesized by optimization for human codons and inserted to a CAR expression vector. The CAR gene used had a gene encoding a fusion peptide (peptide consisting of the amino acid sequence represented by SEQ ID NO: 185) consisting of a human CD8-derived transmembrane region and a human CD28/4-1BB/CD3 zeta-derived immunocompetent cell activation signal transduction region, a 2A self-cleaving sequence, human IL-7 gene, a 2A self-cleaving sequence, human CCL19 gene, a 2A self-cleaving sequence, and HSV-TK gene, downstream of the scFv gene, and the whole was incorporated into a MSGV1 retrovirus vector (see International Publication No. WO 2016/056228).

[Preparation of GPC3 CAR-T Cell]

The GPC3 CAR vectors derived from the 11 types of scFv clones described above were each transiently introduced to GP2 packaging cells to prepare retrovirus vectors. T cells were infected with these vectors for gene transfer to induce GPC3 CAR-T cells. The ratio of GPC3 CAR-expressing cells to the gene-transferred T cells varied from 5.3 to 39.2%. Accordingly, the following function assay was carried out using GPC3 CAR-T cells derived from 5 types of scFv clones (TF1413-02d028, TF1413-02d039, TF1413-02e014, TF1413-02e030, and TF1413-03e005) that exhibited 25% or more of the ratio.

[Damaging Activity of GPC3 CAR-T Cell Against GPC3-Expressing Cell Line]

Figure 5:
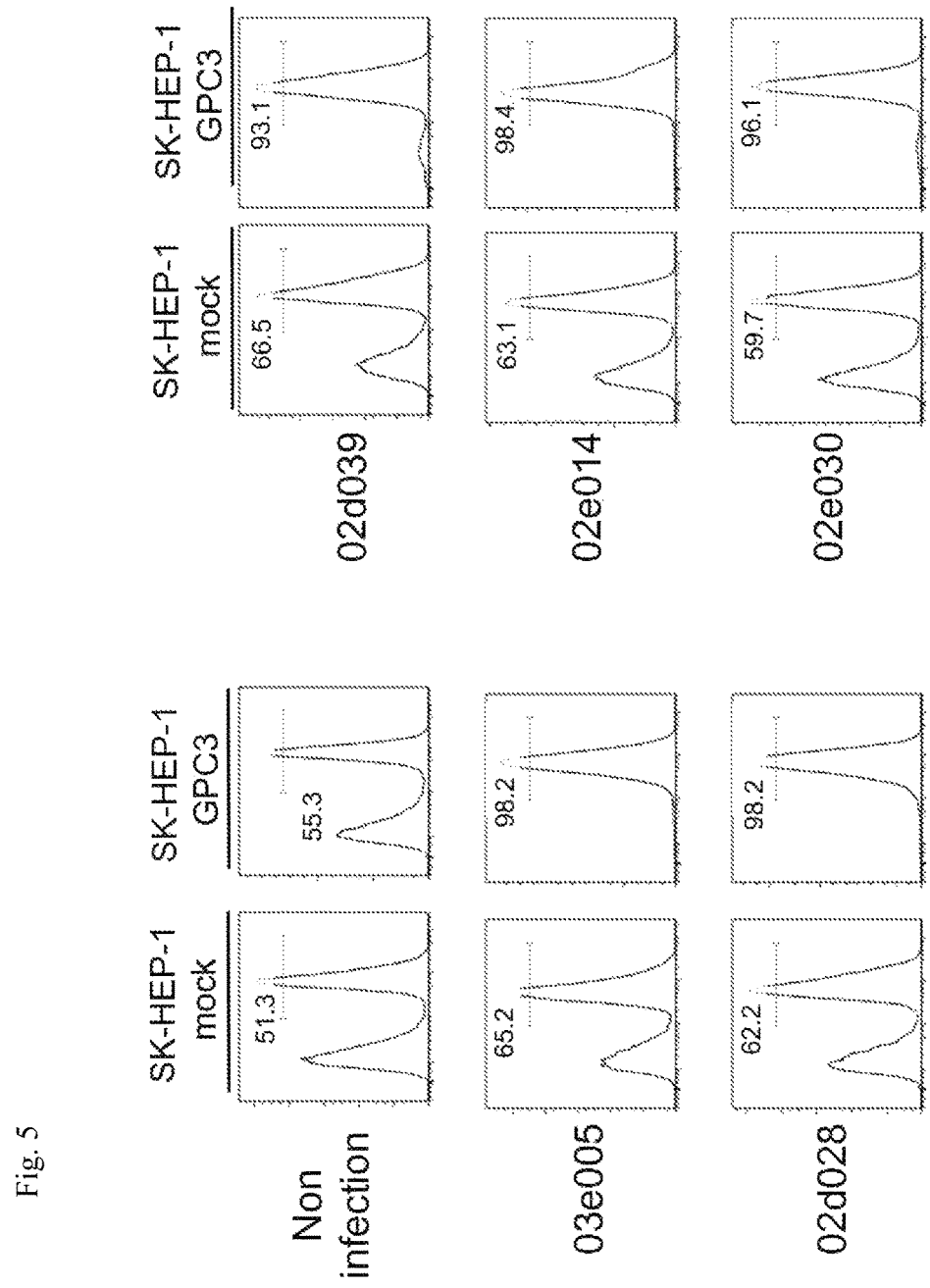
FIG. 5 is a diagram showing results of analyzing GPC3 CAR-T cells (T cells expressing CAR of scFv recognizing GPC3) derived from 5 types of scFv clones (TF1413-02d028, TF1413-02d039, TF1413-02e014, TF1413-02e030, and TF1413-03e005) for cytotoxic activity against a Sk-HEP-1 GPC3 cell line. In each graph, the right peak depicts CD45-positive cells (GPC3 CAR-T cells), and the left peak depicts CD45-negative cells (residual cancer cells [Sk-HEP-1 GPC3 cells]). The ordinate of each graph depicts the number of cells. The numeric value in each graph depicts the ratio (%) of the number of CD45-positive cells to the total number of cells (CD45-positive cells and CD45-negative cells). T cells expressing no GPC3 CAR ("Non infection" in the diagram) were used as a control.
Figure 6A:
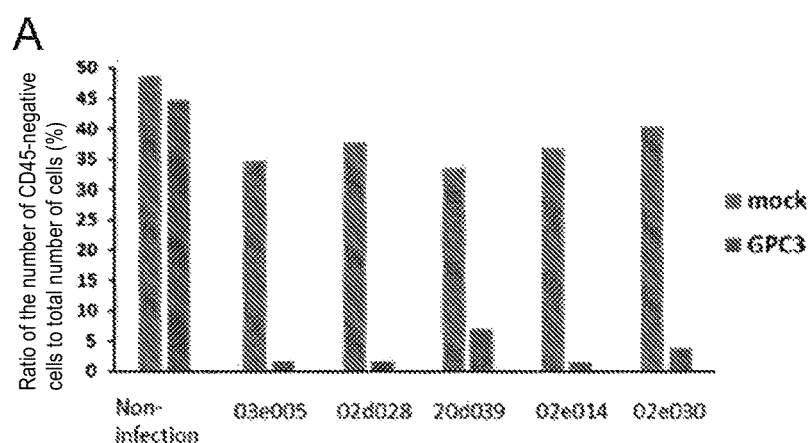
FIGS. 6A and 6B are graphs showing the ratio of CD45-negative cells in FIG. 5 (FIG. 6A) and the number of CD45-negative cells (FIG. 6B). In a pair of bar graphs, the left bar graph depicts "mock" (Sk-HEP-1 mock cell line), and the right bar graph depicts "GPC3" (Sk-HEP-1 GPC3 cell line).
Figure 6B:
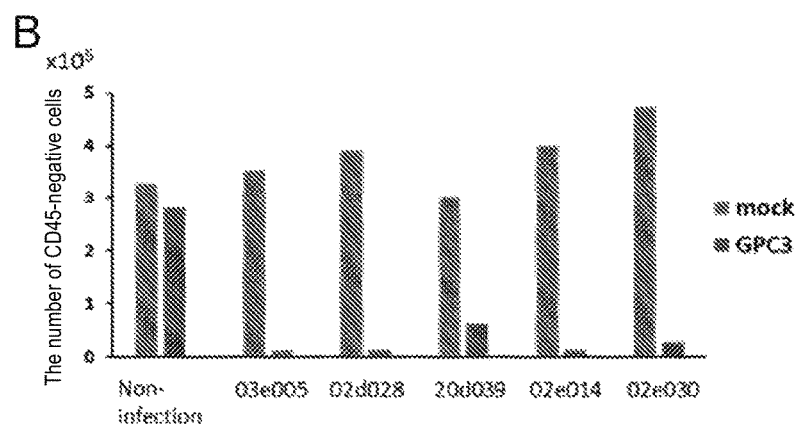

In order to study the damaging activity of the GPC3 CAR-T cells against cancer cells, coculture assay was carried out using the GPC3 CAR-T cells and a GPC3-expressing cell line, i.e., a hepatocellular carcinoma-derived cell line Sk-HEP-1 caused to express GPC3 (Sk-HEP-1 GPC3 cell line), or a cell line expressing no GPC3 (Sk-HEP-1 mock cell line). The GPC3 CAR-T cells were mixed with the target cancer cells (Sk-HEP-1 GPC3 cell line or Sk-HEP-1 mock cell line) at a ratio of 1:1 ($1 \times 10^3$ cells/well) and cultured in a 24-well plate. 48 hours later, the cells were recovered, stained with an anti-CD45 antibody, and analyzed by FCM with CD45-positive cells as GPC3 CAR-T cells and CD45-negative cells as residual cancer cells [Sk- HEP-1 GPC3 cells]. As a result, all the GPC3 CAR-T cells derived from the 5 types of scFv clones described above almost completely damaged the Sk-HEP-1 GPC3 cells, but did not exhibit damaging activity against the Sk-HEP-1 mock cells (see FIGS. 5 and 6). In the case of using cells uninfected with the virus vector (non-gene-transferred cells ["Non infection" in FIGS. 5 and 6]) as a negative control for the GPC3 CAR-T cells, these cells exhibited damaging activity neither against the Sk-HEP-1 GPC3 cells nor against the Sk-HEP-1 mock cells.

From these results, the GPC3CAR-T cells derived from the selected 5 types of anti-GPC3 scFv clones (TF1413-02d028, TF1413-02d039, TF1413-02e014, TF1413-02e030, and TF1413-03e005) were shown to specifically exert cytotoxic activity against cancer cells expressing GPC3.

[Ability of GPC3 CAR-T Cell to Produce IFN-γ by Recognizing GPC3-Expressing Cell]

Figure 7:
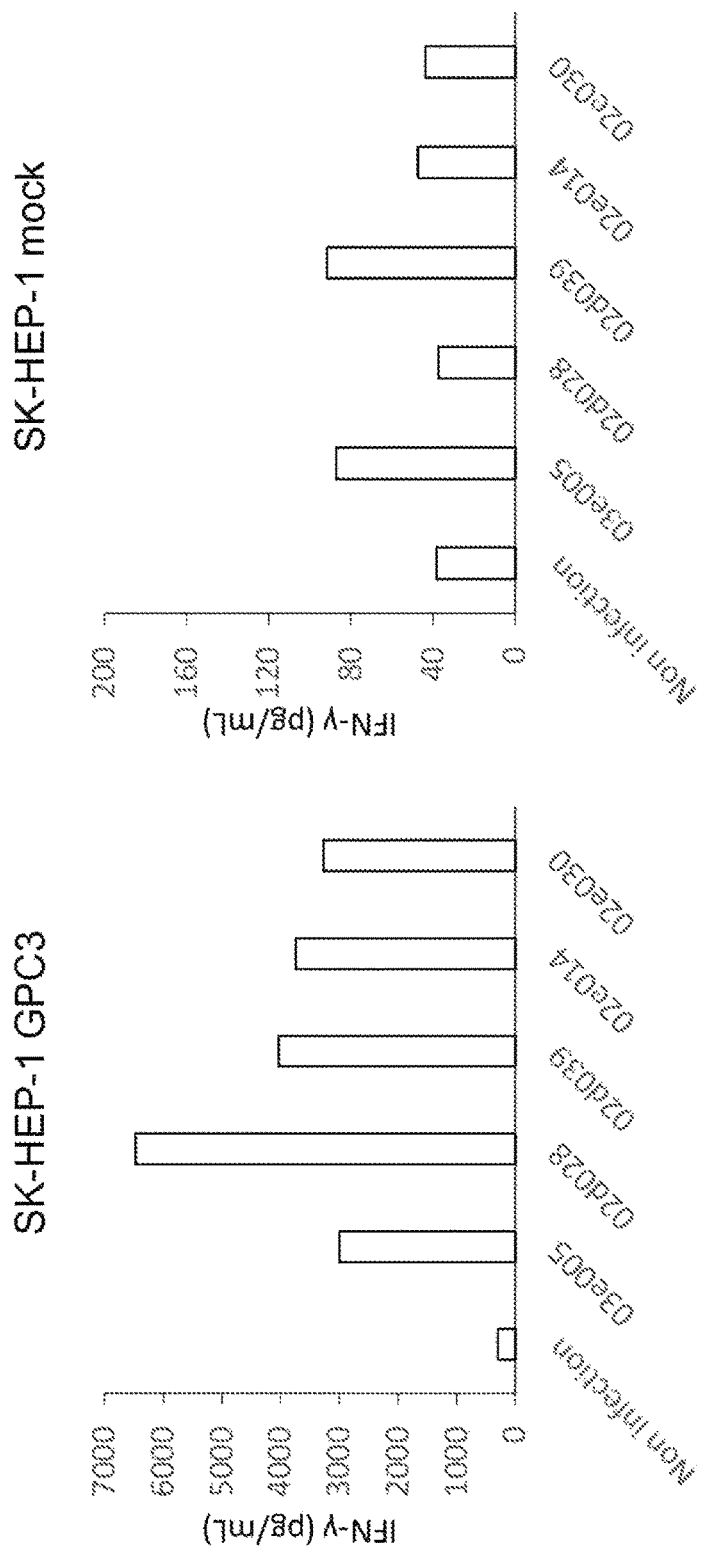
FIG. 7 is a diagram showing results of analyzing GPC3 CAR-T cells derived from 5 types of scFv clones (TF1413-02d028, TF1413-02d039, TF1413-02e014, TF1413-02e030, and TF1413-03e005) for the ability to produce IFN-γ against a Sk-HEP-1 GPC3 cell line. T cells expressing no GPC3 CAR ("Non infection" in the diagram) were used as a control.

In addition to the damaging activity against GPC3-expressing (positive) cancer cells, the ability of the GPC3 CAR-T cells to produce IFN-γ was analyzed. The GPC3 CAR-T cells were mixed with the target cancer cells (Sk-HEP-1 GPC3 cell line or Sk-HEP-1 mock cell line) at a ratio of 1:1 ($1 \times 10^3$ cells/well) and cultured for 48 hours in a 24-well plate, and the concentration of IFN-γ produced into the culture supernatant was measured by ELISA. As a result, all the GPC3 CAR-T cells derived from the 5 types of scFv clones described above exhibited the ability to produce IFN-γ in a manner dependent on the expression of GPC3. Particularly, the GPC3 CAR-T cells derived from clone TF1413-02d028 exhibited the highest ability to produce IFN-γ (see FIG. 7).

Example 4

4. Preparation of Humanized Antibody scFv humanized antibodies were designed on the basis of two types of scFv clones (TF1413-02d028 and 02d039) prepared in Example 1 (see Table 6). The linker used consisted of 15 amino acid residues with 3 repeats of a polypeptide "GGGGS". A human immunoglobulin H chain-derived signal sequence consisting of the amino acid sequence represented by SEQ ID NO: 188 was added to the N terminus of $V_H$.

TABLE 6

SEQ ID NO: 178: #5 VH1-15-VL1 (TF1413-02d028-derived scFv humanized antibody 1)
QVQLVQSGAEVKKPGASVKVSCKASGYSFTGYNMNWVRQAPGQGLEWI
GNIDPYYGGTSYNQKFKGRATLTVDTSTSTAYMELRSLRSDDTAVYYC
ARGDYRAYYFDYWGQGTTVTVSSGGGGSGGGGSGGGGSDIQMTQSPSS
LSASVGDRVTITCKASQNVRTAVAWYQQKPGKAPKALIYLASNRHTGV
PSRFSGSGSGTDFTLTISSLQPEDFATYYCLQHWNYPLTFGGGTKVEI
K SEQ ID NO: 179: #5 VH2-15-VL1 (TF1413-02d028-derived scFv humanized antibody 2)
QVQLVQSGAEVKKPGASVKVSCKASGYSFTGYNMNWVRQAPGQGLEWI
GNIDPYYGGTSYNQKFKGRVTLTVDTSTSTAYMELRSLRSDDTAVYYC
ARGDYRAYYFDYWGQGTTVTVSSGGGGSGGGGSGGGGSDIQMTQSPSS
LSASVGDRVTITCKASQNVRTAVAWYQQKPGKAPKALIYLASNRHTGV
PSRFSGSGSGTDFTLTISSLQPEDFATYYCLQHWNYPLTFGGGTKVEI
K TABLE 6-continued SEQ ID NO: 180: #5 VH3-15-VL1 (TF1413-02d028-derived scFv humanized antibody 3)
QVQLVQSGAEVKKPGASVKVSCKASGYTFTGYNMNWVRQAPGQGLEWI
GNIDPYYGGTSYNQKFKGRVTLTVDTSTSTAYMELRSLRSDDTAVYYC
ARGDYRAYYFDYWGQGTTVTVSSGGGGSGGGGSGGGGSDIQMTQSPSS
LSASVGDRVTITCKASQNVRTAVAWYQQKPGKAPKALIYLASNRHTGV
PSRFSGSGSGTDFTLTISSLQPEDFATYYCLQHWNYPLTFGGGTKVEI
K SEQ ID NO: 181: #6 VH1-15-VL1 (TF1413-02d039-derived scFv humanized antibody 1)
EVQLVESGGGLVQPGGSLRLSCAASGFAFSSYDMSWVRQAPGKGLEWV
AYISSGGGSTYYPDTVKGRFTISRDNAKNSLYLQMNSLRAEDTAVYYC
ARRGLRRAMDYWGQGTMVTVSSGGGGSGGGGSGGGGSDIVMTQSPLSL
PVTPGEPASISCRSSQSLVHSNGNTYLHWYLQKPGQSPQLLIYKVSNR
FSGVPDRFSGSGSGTDFTLKISRVEAEDVGVYYCSQSTHVPLTFGGGT
KVEIK SEQ ID NO: 182: #6 VH1-15-VL2 (TF1413-02d039-derived scFv humanized antibody 2)
EVQLVESGGGLVQPGGSLRLSCAASGFAFSSYDMSWVRQAPGKGLEWV
AYISSGGGSTYYPDTVKGRFTISRDNAKNSLYLQMNSLRAEDTAVYYC
ARRGLRRAMDYWGQGTMVTVSSGGGGSGGGGSGGGGSDIVMTQSPLSL
PVTPGEPASISCRSSQSLVHSSGNTYLHWYLQKPGQSPQLLIYKVSNR
FSGVPDRFSGSGSGTDFTLKISRVEAEDVGVYYCSQSTHVPLTFGGGT
KVEIK SEQ ID NO: 183: #6 VH2-15-VL1 (TF1413-02d039-derived scFv humanized antibody 3)
EVQLVESGGGLVQPGGSLRLSCAASGFAFSSYDMSWVRQAPGKRLEWV
AYISSGGGSTYYPDTVKGRFTISRDNAKNSLYLQMNSLRAEDTAVYYC
ARRGLRRAMDYWGQGTMVTVSSGGGGSGGGGSGGGGSDIVMTQSPLSL
PVTPGEPASISCRSSQSLVHSNGNTYLHWYLQKPGQSPQLLIYKVSNR
FSGVPDRFSGSGSGTDFTLKISRVEAEDVGVYYCSQSTHVPLTFGGGT
KVEIK SEQ ID NO: 184: #6 VH2-15-VL2 (TF1413-02d039-derived scFv humanized antibody 4)
EVQLVESGGGLVQPGGSLRLSCAASGFAFSSYDMSWVRQAPGKRLEWV
AYISSGGGSTYYPDTVKGRFTISRDNAKNSLYLQMNSLRAEDTAVYYC
ARRGLRRAMDYWGQGTMVTVSSGGGGSGGGGSGGGGSDIVMTQSPLSL
PVTPGEPASISCRSSQSLVHSSGNTYLHWYLQKPGQSPQLLIYKVSNR
FSGVPDRFSGSGSGTDFTLKISRVEAEDVGVYYCSQSTHVPLTFGGGT
KVEIK In the tables, the linker is boxed in a double line, $V_H$ is underlined with a single line, and $V_L$ is underlined with a double line.

INDUSTRIAL APPLICABILITY

The present invention contributes to the field of cancer immunotherapy.

The invention claimed is:

1. A single chain antibody specifically binding to a human GPC3 (glypican-3)-derived polypeptide consisting of the amino acid sequence of SEQ ID NO: 155, wherein the single chain antibody
   (1-1) comprises a heavy chain complementarity determining region (CDR) 1 consisting of the amino acid sequence of SEQ ID NO: 1, a heavy chain CDR2 consisting of the amino acid sequence of SEQ ID NO: 2, and a heavy chain CDR3 consisting of the amino acid sequence of SEQ ID NO: 3, and
   a light chain CDR1 consisting of the amino acid sequence of SEQ ID NO: 4, a light chain CDR2 consisting of the amino acid sequence of SEQ ID NO: 5, and a light chain CDR3 consisting of the amino acid sequence of SEQ ID NO: 6.

2. The single chain antibody according to claim 1, wherein the single chain antibody
   (1-2) comprises a heavy chain variable region consisting of an amino acid sequence having at least 80% or higher sequence identity to the amino acid sequence of SEQ ID NO: 7, and a light chain variable region consisting of an amino acid sequence having at least 80% or higher sequence identity to the amino acid sequence of SEQ ID NO: 8.

3. The single chain antibody according to claim 1, wherein the single chain antibody
   (1-3) comprises an amino acid sequence having at least 80% or higher sequence identity to the amino acid sequence of SEQ ID NO: 165.

4. The single chain antibody according to claim 1, wherein the single chain antibody
   (1-3'-1) comprises an amino acid sequence having at least 80% or higher sequence identity to the amino acid sequence of SEQ ID NO: 178; or
   (1-3'-2) comprises an amino acid sequence having at least 80% or higher sequence identity to the amino acid sequence of SEQ ID NO: 179; or
   (1-3'-3) comprises an amino acid sequence having at least 80% or higher sequence identity to the amino acid sequence of SEQ ID NO: 180.

5. A chimeric antigen receptor (CAR) comprising the single chain antibody according to claim 1, a transmembrane region fused with a carboxyl terminus of the single chain antibody, and an immunocompetent cell activation signal transduction region fused with a carboxyl terminus of the transmembrane region.

6. The CAR according to claim 5, comprising the amino acid sequence of any of SEQ ID NOs: 185 to 187.

7. An immunocompetent cell expressing the CAR according to claim 5.

8. The immunocompetent cell according to claim 7, further expressing interleukin 7 (IL-7) and chemokine ligand 19 (CCL19).

* * * * *

```
                         SEQUENCE LISTING

<160> NUMBER OF SEQ ID NOS: 188

<210> SEQ ID NO 1
<211> LENGTH: 5
<212> TYPE: PRT
<213> ORGANISM: Artificial
<220> FEATURE:
<223> OTHER INFORMATION: TF1413-02d028 H Chain CDR 1
<220> FEATURE:
<221> NAME/KEY: MISC_FEATURE
<223> OTHER INFORMATION: Inventor: TAMADA, Koji; SAKODA, Yukimi;
      NAKATSURA, Tetsuya; SAITO, Keigo

<400> SEQUENCE: 1

Gly Tyr Asn Met Asn
1               5

<210> SEQ ID NO 2
<211> LENGTH: 17
<212> TYPE: PRT
<213> ORGANISM: Artificial
<220> FEATURE:
<223> OTHER INFORMATION: TF1413-02d028 H Chain CDR 2

<400> SEQUENCE: 2

Asn Ile Asp Pro Tyr Tyr Gly Gly Thr Ser Tyr Asn Gln Lys Phe Lys
1               5                   10                  15

Gly

<210> SEQ ID NO 3
<211> LENGTH: 10
<212> TYPE: PRT
<213> ORGANISM: Artificial
<220> FEATURE:
<223> OTHER INFORMATION: TF1413-02d028 H Chain CDR 3

<400> SEQUENCE: 3

Gly Asp Tyr Arg Ala Tyr Tyr Phe Asp Tyr
1               5                   10

<210> SEQ ID NO 4
<211> LENGTH: 11
<212> TYPE: PRT
<213> ORGANISM: Artificial
<220> FEATURE:
<223> OTHER INFORMATION: TF1413-02d028 L Chain CDR 1

<400> SEQUENCE: 4

Lys Ala Ser Gln Asn Val Arg Thr Ala Val Ala
1               5                   10

<210> SEQ ID NO 5
<211> LENGTH: 7
<212> TYPE: PRT
<213> ORGANISM: Artificial
<220> FEATURE:
<223> OTHER INFORMATION: TF1413-02d028 L Chain CDR 2

<400> SEQUENCE: 5

Leu Ala Ser Asn Arg His Thr
1               5
```

```
<210> SEQ ID NO 6
<211> LENGTH: 9
<212> TYPE: PRT
<213> ORGANISM: Artificial
<220> FEATURE:
<223> OTHER INFORMATION: TF1413-02d028 L Chain CDR 3

<400> SEQUENCE: 6

Leu Gln His Trp Asn Tyr Pro Leu Thr
1               5

<210> SEQ ID NO 7
<211> LENGTH: 118
<212> TYPE: PRT
<213> ORGANISM: Artificial
<220> FEATURE:
<223> OTHER INFORMATION: TF1413-02d028 H Chain V Region

<400> SEQUENCE: 7

Gln Val Gln Leu Lys Glu Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Asn Met Asn Trp Val Lys Gln Ser Asn Gly Lys Ser Leu Glu Trp Ile
            35                  40                  45

Gly Asn Ile Asp Pro Tyr Tyr Gly Gly Thr Ser Tyr Asn Gln Lys Phe
50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asp Tyr Arg Ala Tyr Tyr Phe Asp Tyr Trp Gly Gln Gly
            100                 105                 110

Thr Thr Leu Thr Val Ser
        115

<210> SEQ ID NO 8
<211> LENGTH: 108
<212> TYPE: PRT
<213> ORGANISM: Artificial
<220> FEATURE:
<223> OTHER INFORMATION: TF1413-02d028 L Chain V Region

<400> SEQUENCE: 8

Asp Ile Gln Met Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys Arg
            100                 105
```

<210> SEQ ID NO 9
<211> LENGTH: 449
<212> TYPE: PRT
<213> ORGANISM: Artificial
<220> FEATURE:
<223> OTHER INFORMATION: TF1413-02d028 H Chain

<400> SEQUENCE: 9

```
Gln Val Gln Leu Lys Glu Ser Gly Pro Glu Leu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asp Tyr Arg Ala Tyr Tyr Phe Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
```

```
            370                 375                 380
Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
                435                 440                 445

Lys

<210> SEQ ID NO 10
<211> LENGTH: 214
<212> TYPE: PRT
<213> ORGANISM: Artificial
<220> FEATURE:
<223> OTHER INFORMATION: TF1413-02d028 L Chain

<400> SEQUENCE: 10

Asp Ile Gln Met Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 11
<211> LENGTH: 5
<212> TYPE: PRT
<213> ORGANISM: Artificial
<220> FEATURE:
<223> OTHER INFORMATION: TF1413-02d039 H Chain CDR 1

<400> SEQUENCE: 11

Ser Tyr Asp Met Ser
```

```
<210> SEQ ID NO 12
<211> LENGTH: 17
<212> TYPE: PRT
<213> ORGANISM: Artificial
<220> FEATURE:
<223> OTHER INFORMATION: TF1413-02d039 H Chain CDR 2

<400> SEQUENCE: 12

Tyr Ile Ser Ser Gly Gly Gly Ser Thr Tyr Tyr Pro Asp Thr Val Lys
1               5                   10                  15
Gly

<210> SEQ ID NO 13
<211> LENGTH: 9
<212> TYPE: PRT
<213> ORGANISM: Artificial
<220> FEATURE:
<223> OTHER INFORMATION: TF1413-02d039 H Chain CDR 3

<400> SEQUENCE: 13

Arg Gly Leu Arg Arg Ala Met Asp Tyr
1               5

<210> SEQ ID NO 14
<211> LENGTH: 16
<212> TYPE: PRT
<213> ORGANISM: Artificial
<220> FEATURE:
<223> OTHER INFORMATION: TF1413-02d039 L Chain CDR 1

<400> SEQUENCE: 14

Arg Ser Ser Gln Ser Leu Val His Ser Asn Gly Asn Thr Tyr Leu His
1               5                   10                  15

<210> SEQ ID NO 15
<211> LENGTH: 7
<212> TYPE: PRT
<213> ORGANISM: Artificial
<220> FEATURE:
<223> OTHER INFORMATION: TF1413-02d039 L Chain CDR 2

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial
<220> FEATURE:
<223> OTHER INFORMATION: TF1413-02d039 L Chain CDR 3

<400> SEQUENCE: 16

Ser Gln Ser Thr His Val Pro Leu Thr
1               5

<210> SEQ ID NO 17
<211> LENGTH: 117
<212> TYPE: PRT
<213> ORGANISM: Artificial
<220> FEATURE:
<223> OTHER INFORMATION: TF1413-02d039 H Chain V Region

<400> SEQUENCE: 17
```

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
                20                  25                  30

Asp Met Ser Trp Val Arg Gln Thr Pro Glu Lys Arg Leu Glu Trp Val
            35                  40                  45

Ala Tyr Ile Ser Ser Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                      70                  75                  80

Leu Gln Met Ser Ser Leu Lys Ser Glu Asp Thr Ala Met Tyr Tyr Cys
                85                  90                  95

Ala Arg Arg Gly Leu Arg Arg Ala Met Asp Tyr Trp Gly Gln Gly Thr
        100                 105                 110

Ser Val Thr Val Ser
        115
```

<210> SEQ ID NO 18
<211> LENGTH: 113
<212> TYPE: PRT
<213> ORGANISM: Artificial
<220> FEATURE:
<223> OTHER INFORMATION: TF1413-02d039 L Chain V Region

<400> SEQUENCE: 18

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                      70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

Arg
```

<210> SEQ ID NO 19
<211> LENGTH: 448
<212> TYPE: PRT
<213> ORGANISM: Artificial
<220> FEATURE:
<223> OTHER INFORMATION: TF1413-02d039 H Chain

<400> SEQUENCE: 19

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
                20                  25                  30

Asp Met Ser Trp Val Arg Gln Thr Pro Glu Lys Arg Leu Glu Trp Val
            35                  40                  45

Ala Tyr Ile Ser Ser Gly Gly Ser Thr Tyr Tyr Pro Asp Thr Val
    50                  55                  60
```

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
             85                  90                  95

Ala Arg Arg Gly Leu Arg Arg Ala Met Asp Tyr Trp Gly Gln Gly Thr
         100                 105                 110

Ser Val Thr Val Ser Ser Ala Lys Thr Thr Ala Pro Ser Val Tyr Pro
     115                 120                 125

Leu Ala Pro Val Cys Gly Asp Thr Thr Gly Ser Ser Val Thr Leu Gly
 130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
             165                 170                 175

Ser Asp Leu Tyr Thr Leu Ser Ser Ser Val Thr Val Thr Ser Ser Thr
         180                 185                 190

Trp Pro Ser Gln Ser Ile Thr Cys Asn Val Ala His Pro Ala Ser Ser
     195                 200                 205

Thr Lys Val Asp Lys Lys Ile Glu Pro Arg Gly Pro Thr Ile Lys Pro
 210                 215                 220

Cys Pro Pro Cys Lys Cys Pro Ala Pro Asn Leu Leu Gly Gly Pro Ser
225                 230                 235                 240

Val Phe Ile Phe Pro Lys Ile Lys Asp Val Leu Met Ile Ser Leu
             245                 250                 255

Ser Pro Ile Val Thr Cys Val Val Val Asp Val Ser Glu Asp Asp Pro
         260                 265                 270

Asp Val Gln Ile Ser Trp Phe Val Asn Asn Val Glu Val His Thr Ala
     275                 280                 285

Gln Thr Gln Thr His Arg Glu Asp Tyr Asn Ser Thr Leu Arg Val Val
 290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
             325                 330                 335

Ile Ser Lys Pro Lys Gly Ser Val Arg Ala Pro Gln Val Tyr Val Leu
         340                 345                 350

Pro Pro Pro Glu Glu Glu Met Thr Lys Lys Gln Val Thr Leu Thr Cys
     355                 360                 365

Met Val Thr Asp Phe Met Pro Glu Asp Ile Tyr Val Glu Trp Thr Asn
 370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
             405                 410                 415

Asn Trp Val Glu Arg Asn Ser Tyr Ser Cys Ser Val Val His Glu Gly
         420                 425                 430

Leu His Asn His His Thr Thr Lys Ser Phe Ser Arg Thr Pro Gly Lys
     435                 440                 445

<210> SEQ ID NO 20
<211> LENGTH: 219
<212> TYPE: PRT
<213> ORGANISM: Artificial
<220> FEATURE:
<223> OTHER INFORMATION: TF1413-02d039 L Chain

<400> SEQUENCE: 20

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 21
<211> LENGTH: 5
<212> TYPE: PRT
<213> ORGANISM: Artificial
<220> FEATURE:
<223> OTHER INFORMATION: TF1413-02e004 H Chain CDR 1

<400> SEQUENCE: 21

Ser Tyr Trp Met Asn
1               5

<210> SEQ ID NO 22
<211> LENGTH: 17
<212> TYPE: PRT
<213> ORGANISM: Artificial
<220> FEATURE:
<223> OTHER INFORMATION: TF1413-02e004 H Chain CDR 2

<400> SEQUENCE: 22

Arg Ile Asp Pro Ser Asp Ser Glu Thr His Tyr Asn Gln Lys Phe Lys
1               5                   10                  15

Asp

<210> SEQ ID NO 23
<211> LENGTH: 7
<212> TYPE: PRT
<213> ORGANISM: Artificial
<220> FEATURE:

-continued

<223> OTHER INFORMATION: TF1413-02e004 H Chain CDR 3

<400> SEQUENCE: 23

Gly Tyr Tyr Ala Met Asp Tyr
1               5

<210> SEQ ID NO 24
<211> LENGTH: 11
<212> TYPE: PRT
<213> ORGANISM: Artificial
<220> FEATURE:
<223> OTHER INFORMATION: TF1413-02e004 L Chain CDR 1

<400> SEQUENCE: 24

Lys Ala Ser Gln Asp Val Ser Thr Ala Val Ala
1               5                   10

<210> SEQ ID NO 25
<211> LENGTH: 7
<212> TYPE: PRT
<213> ORGANISM: Artificial
<220> FEATURE:
<223> OTHER INFORMATION: TF1413-02e004 L Chain CDR 2

<400> SEQUENCE: 25

Ser Ala Ser Tyr Arg Tyr Thr
1               5

<210> SEQ ID NO 26
<211> LENGTH: 8
<212> TYPE: PRT
<213> ORGANISM: Artificial
<220> FEATURE:
<223> OTHER INFORMATION: TF1413-02e004 L Chain CDR 3

<400> SEQUENCE: 26

Gln Gln His Tyr Ser Thr Pro Thr
1               5

<210> SEQ ID NO 27
<211> LENGTH: 115
<212> TYPE: PRT
<213> ORGANISM: Artificial
<220> FEATURE:
<223> OTHER INFORMATION: TF1413-02e004 H Chain V Region

<400> SEQUENCE: 27

Gln Val Gln Leu Gln Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
                20                  25                  30

Trp Met Asn Trp Val Lys Gln Arg Pro Gly Arg Gly Leu Glu Trp Ile
            35                  40                  45

Gly Arg Ile Asp Pro Ser Asp Ser Glu Thr His Tyr Asn Gln Lys Phe
        50                  55                  60

Lys Asp Glu Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Tyr Tyr Ala Met Asp Tyr Trp Gly Gln Gly Thr Ser Val
                100                 105                 110

Thr Val Ser
        115

<210> SEQ ID NO 28
<211> LENGTH: 107
<212> TYPE: PRT
<213> ORGANISM: Artificial
<220> FEATURE:
<223> OTHER INFORMATION: TF1413-02e004 L Chain V Region

<400> SEQUENCE: 28

Asp Ile Val Leu Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Thr
                85                  90                  95

Phe Gly Gly Gly Thr Lys Leu Glu Ile Lys Arg
            100                 105

<210> SEQ ID NO 29
<211> LENGTH: 446
<212> TYPE: PRT
<213> ORGANISM: Artificial
<220> FEATURE:
<223> OTHER INFORMATION: TF1413-02e004 H Chain

<400> SEQUENCE: 29

Gln Val Gln Leu Gln Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Glu Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Tyr Tyr Ala Met Asp Tyr Trp Gly Gln Gly Thr Ser Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys

```
                195                 200                 205
Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
            245                 250                 255

Ile Val Thr Cys Val Val Val Asp Val Ser Glu Asp Pro Asp Val
        260                 265                 270

Gln Ile Ser Trp Phe Val Asn Asn Val Glu Val His Thr Ala Gln Thr
            275                 280                 285

Gln Thr His Arg Glu Asp Tyr Asn Ser Thr Leu Arg Val Val Ser Ala
290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
            325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
                355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
            435                 440                 445

<210> SEQ ID NO 30
<211> LENGTH: 213
<212> TYPE: PRT
<213> ORGANISM: Artificial
<220> FEATURE:
<223> OTHER INFORMATION: TF1413-02e004 L Chain

<400> SEQUENCE: 30

Asp Ile Val Leu Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
```

```
            115                 120                 125
Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 31
<211> LENGTH: 5
<212> TYPE: PRT
<213> ORGANISM: Artificial
<220> FEATURE:
<223> OTHER INFORMATION: TF1413-02e014 H Chain CDR 1

<400> SEQUENCE: 31

Asp Tyr Tyr Met His
1               5

<210> SEQ ID NO 32
<211> LENGTH: 17
<212> TYPE: PRT
<213> ORGANISM: Artificial
<220> FEATURE:
<223> OTHER INFORMATION: TF1413-02e014 H Chain CDR 2

<400> SEQUENCE: 32

Trp Ile Asp Pro Glu Asn Gly Asp Thr Glu Tyr Ala Pro Lys Phe Gln
1               5                   10                  15

Gly

<210> SEQ ID NO 33
<211> LENGTH: 11
<212> TYPE: PRT
<213> ORGANISM: Artificial
<220> FEATURE:
<223> OTHER INFORMATION: TF1413-02e014 H Chain CDR 3

<400> SEQUENCE: 33

Tyr Tyr Asp Tyr Asp Gly Tyr Ala Met Asp Tyr
1               5                   10

<210> SEQ ID NO 34
<211> LENGTH: 11
<212> TYPE: PRT
<213> ORGANISM: Artificial
<220> FEATURE:
<223> OTHER INFORMATION: TF1413-02e014 L Chain CDR 1

<400> SEQUENCE: 34

Lys Ala Ser Gln Asp Val Gly Thr Ala Val Ala
1               5                   10

<210> SEQ ID NO 35
<211> LENGTH: 7
<212> TYPE: PRT
<213> ORGANISM: Artificial
```

```
<220> FEATURE:
<223> OTHER INFORMATION: TF1413-02e014 L Chain CDR 2

<400> SEQUENCE: 35

Trp Ala Ser Thr Arg His Thr
1               5

<210> SEQ ID NO 36
<211> LENGTH: 9
<212> TYPE: PRT
<213> ORGANISM: Artificial
<220> FEATURE:
<223> OTHER INFORMATION: TF1413-02e014 L Chain CDR 3

<400> SEQUENCE: 36

Gln Gln Tyr Ser Ser Tyr Pro Leu Thr
1               5

<210> SEQ ID NO 37
<211> LENGTH: 120
<212> TYPE: PRT
<213> ORGANISM: Artificial
<220> FEATURE:
<223> OTHER INFORMATION: TF1413-02e014 H Chain V Region

<400> SEQUENCE: 37

Gln Val Gln Leu Lys Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gly Tyr Tyr Asp Tyr Asp Gly Tyr Ala Met Asp Tyr Trp Gly
            100                 105                 110

Gln Gly Thr Ser Val Thr Val Ser
        115                 120

<210> SEQ ID NO 38
<211> LENGTH: 108
<212> TYPE: PRT
<213> ORGANISM: Artificial
<220> FEATURE:
<223> OTHER INFORMATION: TF1413-02e014 L Chain V Region

<400> SEQUENCE: 38

Asp Ile Val Leu Thr Gln Ser Pro Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80
```

Glu Asp Leu Ala Asp Tyr Phe Cys Gln Gln Tyr Ser Ser Tyr Pro Leu
                85                  90                  95

Thr Phe Gly Gly Gly Thr Lys Leu Glu Ile Lys Arg
            100                 105

<210> SEQ ID NO 39
<211> LENGTH: 451
<212> TYPE: PRT
<213> ORGANISM: Artificial
<220> FEATURE:
<223> OTHER INFORMATION: TF1413-02e014 H Chain

<400> SEQUENCE: 39

Gln Val Gln Leu Lys Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gly Tyr Tyr Asp Tyr Asp Gly Tyr Ala Met Asp Tyr Trp Gly
            100                 105                 110

Gln Gly Thr Ser Val Thr Val Ser Ser Ala Lys Lys Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

```
Glu Arg Thr Ile Ser Lys Pro Lys Gly Ser Val Arg Ala Pro Gln Val
            340                 345                 350

Tyr Val Leu Pro Pro Glu Glu Met Thr Lys Lys Gln Val Thr
            355                 360                 365

Leu Thr Cys Met Val Thr Asp Phe Met Pro Glu Asp Ile Tyr Val Glu
370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
            435                 440                 445

Pro Gly Lys
    450

<210> SEQ ID NO 40
<211> LENGTH: 214
<212> TYPE: PRT
<213> ORGANISM: Artificial
<220> FEATURE:
<223> OTHER INFORMATION: TF1413-02e014 L Chain

<400> SEQUENCE: 40

Asp Ile Val Leu Thr Gln Ser Pro Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 41
```

```
<211> LENGTH: 5
<212> TYPE: PRT
<213> ORGANISM: Artificial
<220> FEATURE:
<223> OTHER INFORMATION: TF1413-02e030 H Chain CDR 1

<400> SEQUENCE: 41

Asp Tyr Tyr Met His
1               5

<210> SEQ ID NO 42
<211> LENGTH: 17
<212> TYPE: PRT
<213> ORGANISM: Artificial
<220> FEATURE:
<223> OTHER INFORMATION: TF1413-02e030 H Chain CDR 2

<400> SEQUENCE: 42

Trp Ile Asp Pro Glu Asn Gly Asn Thr Ile Tyr Asp Pro Lys Phe Gln
1               5                   10                  15

Gly

<210> SEQ ID NO 43
<211> LENGTH: 8
<212> TYPE: PRT
<213> ORGANISM: Artificial
<220> FEATURE:
<223> OTHER INFORMATION: TF1413-02e030 H Chain CDR 3

<400> SEQUENCE: 43

Thr Met Ile Thr Thr Leu Asp Tyr
1               5

<210> SEQ ID NO 44
<211> LENGTH: 17
<212> TYPE: PRT
<213> ORGANISM: Artificial
<220> FEATURE:
<223> OTHER INFORMATION: TF1413-02e030 L Chain CDR 1

<400> SEQUENCE: 44

Lys Ser Ser Gln Ser Leu Leu Asn Ser Ser Asn Gln Lys Asn Tyr Leu
1               5                   10                  15

Ala

<210> SEQ ID NO 45
<211> LENGTH: 7
<212> TYPE: PRT
<213> ORGANISM: Artificial
<220> FEATURE:
<223> OTHER INFORMATION: TF1413-02e030 L Chain CDR 2

<400> SEQUENCE: 45

Phe Ala Ser Thr Arg Glu Ser
1               5

<210> SEQ ID NO 46
<211> LENGTH: 9
<212> TYPE: PRT
<213> ORGANISM: Artificial
<220> FEATURE:
<223> OTHER INFORMATION: TF1413-02e030 L Chain CDR 3

<400> SEQUENCE: 46

Gln Gln His Tyr Ser Thr Pro Leu Thr
1               5
```

<210> SEQ ID NO 47
<211> LENGTH: 117
<212> TYPE: PRT
<213> ORGANISM: Artificial
<220> FEATURE:
<223> OTHER INFORMATION: TF1413-02e030 H Chain V Region

<400> SEQUENCE: 47

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asn Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ile Ser Thr Met Ile Thr Thr Leu Asp Tyr Trp Gly Gln Gly Thr
            100                 105                 110

Thr Leu Thr Val Ser
        115

<210> SEQ ID NO 48
<211> LENGTH: 114
<212> TYPE: PRT
<213> ORGANISM: Artificial
<220> FEATURE:
<223> OTHER INFORMATION: TF1413-02e030 L Chain V Region

<400> SEQUENCE: 48

Asp Ile Gln Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Arg

<210> SEQ ID NO 49
<211> LENGTH: 448
<212> TYPE: PRT
<213> ORGANISM: Artificial
<220> FEATURE:
<223> OTHER INFORMATION: TF1413-02e030 H Chain

<400> SEQUENCE: 49

Glu Val Gln Leu Gln Gln Ser Gly Ala Glu Leu Val Arg Pro Gly Ala

-continued

```
1               5                   10                  15
Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
            35                  40                  45

Gly Trp Ile Asp Pro Glu Asn Gly Asn Thr Ile Tyr Asp Pro Lys Phe
        50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ile Ser Thr Met Ile Thr Thr Leu Asp Tyr Trp Gly Gln Gly Thr
            100                 105                 110

Thr Leu Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
        130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
            195                 200                 205

Thr Lys Val Asp Lys Lys Ile Glu Pro Arg Gly Pro Thr Ile Lys Pro
        210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
        290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
        370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430
```

```
Leu His Asn His His Thr Thr Lys Ser Phe Ser Arg Thr Pro Gly Lys
        435                 440                 445
```

<210> SEQ ID NO 50
<211> LENGTH: 220
<212> TYPE: PRT
<213> ORGANISM: Artificial
<220> FEATURE:
<223> OTHER INFORMATION: TF1413-02e030 L Chain

<400> SEQUENCE: 50

```
Asp Ile Gln Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220
```

<210> SEQ ID NO 51
<211> LENGTH: 5
<212> TYPE: PRT
<213> ORGANISM: Artificial
<220> FEATURE:
<223> OTHER INFORMATION: TF1413-02e040 H Chain CDR 1

<400> SEQUENCE: 51

```
Gly Tyr Thr Met Asn
1               5
```

<210> SEQ ID NO 52
<211> LENGTH: 17
<212> TYPE: PRT
<213> ORGANISM: Artificial
<220> FEATURE:
<223> OTHER INFORMATION: TF1413-02e040 H Chain CDR 2

<400> SEQUENCE: 52

Leu Ile Asn Pro Tyr Asn Gly Gly Thr Ser Tyr Asn Gln Asn Phe Lys
1               5                   10                  15

Gly

<210> SEQ ID NO 53
<211> LENGTH: 8
<212> TYPE: PRT
<213> ORGANISM: Artificial
<220> FEATURE:
<223> OTHER INFORMATION: TF1413-02e040 H Chain CDR 3

<400> SEQUENCE: 53

Gly Tyr Tyr Gly Arg Phe Asp Tyr
1               5

<210> SEQ ID NO 54
<211> LENGTH: 11
<212> TYPE: PRT
<213> ORGANISM: Artificial
<220> FEATURE:
<223> OTHER INFORMATION: TF1413-02e040 L Chain CDR 1

<400> SEQUENCE: 54

Lys Ala Ser Gln Asn Val Arg Thr Ala Val Ala
1               5                   10

<210> SEQ ID NO 55
<211> LENGTH: 7
<212> TYPE: PRT
<213> ORGANISM: Artificial
<220> FEATURE:
<223> OTHER INFORMATION: TF1413-02e040 L Chain CDR 2

<400> SEQUENCE: 55

Leu Ala Ser Asn Arg His Thr
1               5

<210> SEQ ID NO 56
<211> LENGTH: 9
<212> TYPE: PRT
<213> ORGANISM: Artificial
<220> FEATURE:
<223> OTHER INFORMATION: TF1413-02e040 L Chain CDR 3

<400> SEQUENCE: 56

Leu Gln His Trp Asn Tyr Pro Leu Thr
1               5

<210> SEQ ID NO 57
<211> LENGTH: 116
<212> TYPE: PRT
<213> ORGANISM: Artificial
<220> FEATURE:
<223> OTHER INFORMATION: TF1413-02e040 H Chain V Region

<400> SEQUENCE: 57

Glu Val Met Leu Val Glu Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Asn Phe
    50                  55                  60

```
Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Gly Tyr Tyr Gly Arg Phe Asp Tyr Trp Gly Gln Gly Thr Thr
            100                 105                 110

Leu Thr Val Ser
        115

<210> SEQ ID NO 58
<211> LENGTH: 108
<212> TYPE: PRT
<213> ORGANISM: Artificial
<220> FEATURE:
<223> OTHER INFORMATION: TF1413-02e040 L Chain V Region

<400> SEQUENCE: 58

Asp Ile Leu Leu Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys Arg
            100                 105

<210> SEQ ID NO 59
<211> LENGTH: 447
<212> TYPE: PRT
<213> ORGANISM: Artificial
<220> FEATURE:
<223> OTHER INFORMATION: TF1413-02e040 H Chain

<400> SEQUENCE: 59

Glu Val Met Leu Val Glu Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Asn Phe
    50                  55                  60

Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Gly Tyr Tyr Gly Arg Phe Asp Tyr Trp Gly Gln Gly Thr Thr
            100                 105                 110

Leu Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140
```

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val His Glu Gly Leu
            420                 425                 430

His Asn His His Thr Thr Lys Ser Phe Ser Arg Thr Pro Gly Lys
        435                 440                 445

<210> SEQ ID NO 60
<211> LENGTH: 214
<212> TYPE: PRT
<213> ORGANISM: Artificial
<220> FEATURE:
<223> OTHER INFORMATION: TF1413-02e040 L Chain

<400> SEQUENCE: 60

Asp Ile Leu Leu Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
        50                  55                  60

```
Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln His Trp Asn Tyr Pro Leu
             85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 61
<211> LENGTH: 5
<212> TYPE: PRT
<213> ORGANISM: Artificial
<220> FEATURE:
<223> OTHER INFORMATION: TF1413-03e001 H Chain CDR 1

<400> SEQUENCE: 61

Gly Tyr Tyr Met His
1               5

<210> SEQ ID NO 62
<211> LENGTH: 17
<212> TYPE: PRT
<213> ORGANISM: Artificial
<220> FEATURE:
<223> OTHER INFORMATION: TF1413-03e001 H Chain CDR 2

<400> SEQUENCE: 62

Arg Ile Asn Pro Tyr Asn Gly Ala Thr Ser Tyr Asn Gln Asn Phe Lys
1               5                   10                  15

Asp

<210> SEQ ID NO 63
<211> LENGTH: 7
<212> TYPE: PRT
<213> ORGANISM: Artificial
<220> FEATURE:
<223> OTHER INFORMATION: TF1413-03e001 H Chain CDR 3

<400> SEQUENCE: 63

Asn Tyr Gly Tyr Phe Asp Tyr
1               5

<210> SEQ ID NO 64
<211> LENGTH: 11
<212> TYPE: PRT
<213> ORGANISM: Artificial
<220> FEATURE:
<223> OTHER INFORMATION: TF1413-03e001 L Chain CDR 1
```

```
<400> SEQUENCE: 64

Glu Ala Ser Gln Asn Val Asp Asn Asn Val Val
1               5                   10

<210> SEQ ID NO 65
<211> LENGTH: 7
<212> TYPE: PRT
<213> ORGANISM: Artificial
<220> FEATURE:
<223> OTHER INFORMATION: TF1413-03e001 L Chain CDR 2

<400> SEQUENCE: 65

Ser Ala Ser Tyr Arg Tyr Ser
1               5

<210> SEQ ID NO 66
<211> LENGTH: 9
<212> TYPE: PRT
<213> ORGANISM: Artificial
<220> FEATURE:
<223> OTHER INFORMATION: TF1413-03e001 L Chain CDR 3

<400> SEQUENCE: 66

Gln Gln Tyr Asn Ser Tyr Pro Leu Thr
1               5

<210> SEQ ID NO 67
<211> LENGTH: 115
<212> TYPE: PRT
<213> ORGANISM: Artificial
<220> FEATURE:
<223> OTHER INFORMATION: TF1413-03e001 H Chain V Region

<400> SEQUENCE: 67

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Val Lys Ser Leu Glu Trp Ile
            35                  40                  45

Gly Arg Ile Asn Pro Tyr Asn Gly Ala Thr Ser Tyr Asn Gln Asn Phe
        50                  55                  60

Lys Asp Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Asn Tyr Gly Tyr Phe Asp Tyr Trp Gly Gln Gly Thr Thr Leu
                100                 105                 110

Thr Val Ser
        115

<210> SEQ ID NO 68
<211> LENGTH: 108
<212> TYPE: PRT
<213> ORGANISM: Artificial
<220> FEATURE:
<223> OTHER INFORMATION: TF1413-03e001 L Chain V Region

<400> SEQUENCE: 68

Asp Ile Lys Met Thr Gln Ser Pro Lys Phe Met Ser Thr Ser Val Gly
1               5                   10                  15
```

```
Asp Arg Val Ser Val Thr Cys Glu Ala Ser Gln Asn Val Asp Asn Asn
            20                  25                  30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Arg
            100                 105

<210> SEQ ID NO 69
<211> LENGTH: 446
<212> TYPE: PRT
<213> ORGANISM: Artificial
<220> FEATURE:
<223> OTHER INFORMATION: TF1413-03e001 H Chain

<400> SEQUENCE: 69

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Val Lys Ser Leu Glu Trp Ile
        35                  40                  45

Gly Arg Ile Asn Pro Tyr Asn Gly Ala Thr Ser Tyr Asn Gln Asn Phe
    50                  55                  60

Lys Asp Lys Ala Ser Leu Thr Val Asp Lys Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Asn Tyr Gly Tyr Phe Asp Tyr Trp Gly Gln Gly Thr Thr Leu
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270
```

Gln Ile Ser Trp Phe Val Asn Asn Val Glu Val His Thr Ala Gln Thr
                275                 280                 285

Gln Thr His Arg Glu Asp Tyr Asn Ser Thr Leu Arg Val Val Ser Ala
            290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
            355                 360                 365

Thr Asp Phe Met Pro Glu Asp Ile Tyr Val Glu Trp Thr Asn Asn Gly
        370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 70
<211> LENGTH: 214
<212> TYPE: PRT
<213> ORGANISM: Artificial
<220> FEATURE:
<223> OTHER INFORMATION: TF1413-03e001 L Chain

<400> SEQUENCE: 70

Asp Ile Lys Met Thr Gln Ser Pro Lys Phe Met Ser Thr Ser Val Gly
1               5                   10                  15

Asp Arg Val Ser Val Thr Cys Glu Ala Ser Gln Asn Val Asp Asn Asn
            20                  25                  30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

```
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 71
<211> LENGTH: 5
<212> TYPE: PRT
<213> ORGANISM: Artificial
<220> FEATURE:
<223> OTHER INFORMATION: TF1413-03e004 H Chain CDR 1

<400> SEQUENCE: 71

Ser Tyr Trp Met Asn
1               5

<210> SEQ ID NO 72
<211> LENGTH: 17
<212> TYPE: PRT
<213> ORGANISM: Artificial
<220> FEATURE:
<223> OTHER INFORMATION: TF1413-03e004 H Chain CDR 2

<400> SEQUENCE: 72

Arg Ile Asp Pro Ser Asp Ser Glu Thr His Tyr Asn Gln Lys Phe Lys
1               5                   10                  15
Asp

<210> SEQ ID NO 73
<211> LENGTH: 7
<212> TYPE: PRT
<213> ORGANISM: Artificial
<220> FEATURE:
<223> OTHER INFORMATION: TF1413-03e004 H Chain CDR 3

<400> SEQUENCE: 73

Gly Tyr Tyr Gly Ser Asn Tyr
1               5

<210> SEQ ID NO 74
<211> LENGTH: 11
<212> TYPE: PRT
<213> ORGANISM: Artificial
<220> FEATURE:
<223> OTHER INFORMATION: TF1413-03e004 L Chain CDR 1

<400> SEQUENCE: 74

Lys Ala Ser Gln Asn Val Gly Thr Asn Val Ala
1               5                   10

<210> SEQ ID NO 75
<211> LENGTH: 7
<212> TYPE: PRT
<213> ORGANISM: Artificial
<220> FEATURE:
<223> OTHER INFORMATION: TF1413-03e004 L Chain CDR 2

<400> SEQUENCE: 75

Ser Ala Ser Tyr Arg Tyr Ser
1               5

<210> SEQ ID NO 76
<211> LENGTH: 9
<212> TYPE: PRT
<213> ORGANISM: Artificial
<220> FEATURE:
```

-continued

<223> OTHER INFORMATION: TF1413-03e004 L Chain CDR 3

<400> SEQUENCE: 76

Gln Gln Tyr Asn Ser Tyr Pro Leu Thr
1               5

<210> SEQ ID NO 77
<211> LENGTH: 115
<212> TYPE: PRT
<213> ORGANISM: Artificial
<220> FEATURE:
<223> OTHER INFORMATION: TF1413-03e004 H Chain V Region

<400> SEQUENCE: 77

Gln Val Gln Leu Lys Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
                20                  25                  30

Trp Met Asn Trp Val Lys Gln Arg Pro Gly Arg Gly Leu Glu Trp Ile
            35                  40                  45

Gly Arg Ile Asp Pro Ser Asp Ser Glu Thr His Tyr Asn Gln Lys Phe
        50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Tyr Tyr Gly Ser Asn Tyr Trp Gly Gln Gly Thr Thr Leu
            100                 105                 110

Thr Val Ser
        115

<210> SEQ ID NO 78
<211> LENGTH: 108
<212> TYPE: PRT
<213> ORGANISM: Artificial
<220> FEATURE:
<223> OTHER INFORMATION: TF1413-03e004 L Chain V Region

<400> SEQUENCE: 78

Asp Ile Lys Met Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys Arg
            100                 105

<210> SEQ ID NO 79
<211> LENGTH: 403
<212> TYPE: PRT
<213> ORGANISM: Artificial
<220> FEATURE:
<223> OTHER INFORMATION: TF1413-03e004 H Chain

<400> SEQUENCE: 79

Gln Val Gln Leu Lys Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Tyr Tyr Gly Ser Asn Tyr Trp Gly Gln Gly Thr Thr Leu
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr

```
<210> SEQ ID NO 80
<211> LENGTH: 214
<212> TYPE: PRT
<213> ORGANISM: Artificial
<220> FEATURE:
<223> OTHER INFORMATION: TF1413-03e004 L Chain

<400> SEQUENCE: 80

Asp Ile Lys Met Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 81
<211> LENGTH: 5
<212> TYPE: PRT
<213> ORGANISM: Artificial
<220> FEATURE:
<223> OTHER INFORMATION: TF1413-03e005 H Chain CDR 1

<400> SEQUENCE: 81

Asp Tyr Tyr Met His
1               5

<210> SEQ ID NO 82
<211> LENGTH: 17
<212> TYPE: PRT
<213> ORGANISM: Artificial
<220> FEATURE:
<223> OTHER INFORMATION: TF1413-03e005 H Chain CDR 2

<400> SEQUENCE: 82

Trp Ile Asp Pro Glu Asn Gly Asp Thr Glu Tyr Ala Pro Lys Phe Gln
1               5                   10                  15
```

Gly

<210> SEQ ID NO 83
<211> LENGTH: 11
<212> TYPE: PRT
<213> ORGANISM: Artificial
<220> FEATURE:
<223> OTHER INFORMATION: TF1413-03e005 H Chain CDR 3

<400> SEQUENCE: 83

Tyr Tyr Asp Tyr Asp Gly Tyr Ala Met Asp Tyr
1               5                   10

<210> SEQ ID NO 84
<211> LENGTH: 11
<212> TYPE: PRT
<213> ORGANISM: Artificial
<220> FEATURE:
<223> OTHER INFORMATION: TF1413-03e005 L Chain CDR 1

<400> SEQUENCE: 84

Arg Ala Ser Gln Glu Ile Ser Gly Tyr Leu Ser
1               5                   10

<210> SEQ ID NO 85
<211> LENGTH: 7
<212> TYPE: PRT
<213> ORGANISM: Artificial
<220> FEATURE:
<223> OTHER INFORMATION: TF1413-03e005 L Chain CDR 2

<400> SEQUENCE: 85

Ala Ala Ser Thr Leu Asp Ser
1               5

<210> SEQ ID NO 86
<211> LENGTH: 9
<212> TYPE: PRT
<213> ORGANISM: Artificial
<220> FEATURE:
<223> OTHER INFORMATION: TF1413-03e005 L Chain CDR 3

<400> SEQUENCE: 86

Leu Gln Tyr Ala Ser Tyr Pro Leu Thr
1               5

<210> SEQ ID NO 87
<211> LENGTH: 120
<212> TYPE: PRT
<213> ORGANISM: Artificial
<220> FEATURE:
<223> OTHER INFORMATION: TF1413-03e005 H Chain V Region

<400> SEQUENCE: 87

Gln Val Gln Leu Lys Glu Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

```
Leu Gln Leu Ser Ser Leu Thr Ser Glu Asp Thr Ala Val Tyr Tyr Cys
                85                  90                  95

Asn Ala Phe Tyr Tyr Asp Tyr Asp Gly Tyr Ala Met Asp Tyr Trp Gly
            100                 105                 110

Gln Gly Thr Ser Val Thr Val Ser
        115                 120

<210> SEQ ID NO 88
<211> LENGTH: 108
<212> TYPE: PRT
<213> ORGANISM: Artificial
<220> FEATURE:
<223> OTHER INFORMATION: TF1413-03e005 L Chain V Region

<400> SEQUENCE: 88

Asp Val Val Met Thr Gln Thr Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys Arg
            100                 105

<210> SEQ ID NO 89
<211> LENGTH: 451
<212> TYPE: PRT
<213> ORGANISM: Artificial
<220> FEATURE:
<223> OTHER INFORMATION: TF1413-03e005 H Chain

<400> SEQUENCE: 89

Gln Val Gln Leu Lys Glu Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Phe Tyr Tyr Asp Tyr Asp Gly Tyr Ala Met Asp Tyr Trp Gly
            100                 105                 110

Gln Gly Thr Ser Val Thr Val Ser Arg Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160
```

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly Lys
    450

<210> SEQ ID NO 90
<211> LENGTH: 214
<212> TYPE: PRT
<213> ORGANISM: Artificial
<220> FEATURE:
<223> OTHER INFORMATION: TF1413-03e005 L Chain

<400> SEQUENCE: 90

Asp Val Val Met Thr Gln Thr Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

-continued

```
Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Leu
             85                  90                  95

Thr Phe Gly Ala Gly Thr Lys Leu Glu Leu Lys Arg Ala Asp Ala Ala
        100                 105                 110

Pro Thr Val Ser Ile Phe Pro Pro Ser Ser Glu Gln Leu Thr Ser Gly
    115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 91
<211> LENGTH: 5
<212> TYPE: PRT
<213> ORGANISM: Artificial
<220> FEATURE:
<223> OTHER INFORMATION: TF1413-03e015 H Chain CDR 1

<400> SEQUENCE: 91

```
Gly Tyr Thr Met Asn
1               5
```

<210> SEQ ID NO 92
<211> LENGTH: 17
<212> TYPE: PRT
<213> ORGANISM: Artificial
<220> FEATURE:
<223> OTHER INFORMATION: TF1413-03e015 H Chain CDR 2

<400> SEQUENCE: 92

```
Leu Ile Asn Pro Tyr Asn Gly Gly Thr Ser Tyr Asn Gln Lys Phe Lys
1               5                   10                  15

Gly
```

<210> SEQ ID NO 93
<211> LENGTH: 11
<212> TYPE: PRT
<213> ORGANISM: Artificial
<220> FEATURE:
<223> OTHER INFORMATION: TF1413-03e015 H Chain CDR 3

<400> SEQUENCE: 93

```
Gly Asp Tyr Tyr Pro Tyr Ala Met Asp Tyr
1               5                   10
```

<210> SEQ ID NO 94
<211> LENGTH: 11
<212> TYPE: PRT
<213> ORGANISM: Artificial
<220> FEATURE:
<223> OTHER INFORMATION: TF1413-03e015 L Chain CDR 1

```
<400> SEQUENCE: 94

Lys Ala Ser Gln Asn Val Gly Thr Asn Val Ala
1               5                   10

<210> SEQ ID NO 95
<211> LENGTH: 7
<212> TYPE: PRT
<213> ORGANISM: Artificial
<220> FEATURE:
<223> OTHER INFORMATION: TF1413-03e015 L Chain CDR 2

<400> SEQUENCE: 95

Ser Ala Ser Tyr Arg Tyr Ser
1               5

<210> SEQ ID NO 96
<211> LENGTH: 9
<212> TYPE: PRT
<213> ORGANISM: Artificial
<220> FEATURE:
<223> OTHER INFORMATION: TF1413-03e015 L Chain CDR 3

<400> SEQUENCE: 96

Gln Gln Tyr Asn Arg Tyr Pro Leu Thr
1               5

<210> SEQ ID NO 97
<211> LENGTH: 119
<212> TYPE: PRT
<213> ORGANISM: Artificial
<220> FEATURE:
<223> OTHER INFORMATION: TF1413-03e015 H Chain V Region

<400> SEQUENCE: 97

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Asp Tyr Tyr Pro Pro Tyr Ala Met Asp Tyr Trp Gly Gln
            100                 105                 110

Gly Thr Ser Val Thr Val Ser
        115

<210> SEQ ID NO 98
<211> LENGTH: 108
<212> TYPE: PRT
<213> ORGANISM: Artificial
<220> FEATURE:
<223> OTHER INFORMATION: TF1413-03e015 L Chain V Region

<400> SEQUENCE: 98

Asp Ile Val Met Ser Gln Ser Pro Lys Phe Met Ser Thr Ser Val Gly
1               5                   10                  15
```

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Arg Tyr Pro Leu
                85                  90                  95

Thr Phe Gly Val Gly Thr Lys Leu Glu Ile Lys Arg
            100                 105

<210> SEQ ID NO 99
<211> LENGTH: 450
<212> TYPE: PRT
<213> ORGANISM: Artificial
<220> FEATURE:
<223> OTHER INFORMATION: TF1413-03e015 H Chain

<400> SEQUENCE: 99

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
 50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Asp Tyr Tyr Pro Pro Tyr Ala Met Asp Tyr Trp Gly Gln
                100                 105                 110

Gly Thr Ser Val Thr Val Ser Ser Ala Lys Thr Thr Ala Pro Ser Val
            115                 120                 125

Tyr Pro Leu Ala Pro Val Cys Gly Asp Thr Thr Gly Ser Ser Val Thr
        130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

```
Asp Pro Asp Val Gln Ile Ser Trp Phe Val Asn Asn Val Glu Val His
            275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
            370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
            435                 440                 445

Gly Lys
    450

<210> SEQ ID NO 100
<211> LENGTH: 214
<212> TYPE: PRT
<213> ORGANISM: Artificial
<220> FEATURE:
<223> OTHER INFORMATION: TF1413-03e015 L Chain

<400> SEQUENCE: 100

Asp Ile Val Met Ser Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Arg Tyr Pro Leu
                85                  90                  95

Thr Phe Gly Val Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175
```

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 101
<211> LENGTH: 5
<212> TYPE: PRT
<213> ORGANISM: Artificial
<220> FEATURE:
<223> OTHER INFORMATION: TF1413-03e034 H Chain CDR 1

<400> SEQUENCE: 101

Gly Tyr Asn Met Asn
1               5

<210> SEQ ID NO 102
<211> LENGTH: 17
<212> TYPE: PRT
<213> ORGANISM: Artificial
<220> FEATURE:
<223> OTHER INFORMATION: TF1413-03e034 H Chain CDR 2

<400> SEQUENCE: 102

Asn Ile Asp Pro Tyr Tyr Gly Gly Thr Ser Tyr Asn Gln Lys Phe Lys
1               5                   10                  15

Gly

<210> SEQ ID NO 103
<211> LENGTH: 10
<212> TYPE: PRT
<213> ORGANISM: Artificial
<220> FEATURE:
<223> OTHER INFORMATION: TF1413-03e034 H Chain CDR 3

<400> SEQUENCE: 103

Gly Asn Tyr Gly Tyr Tyr Ala Met Asp Tyr
1               5                   10

<210> SEQ ID NO 104
<211> LENGTH: 11
<212> TYPE: PRT
<213> ORGANISM: Artificial
<220> FEATURE:
<223> OTHER INFORMATION: TF1413-03e034 L Chain CDR 1

<400> SEQUENCE: 104

Lys Ala Ser Gln Asn Val Arg Thr Ala Val Ala
1               5                   10

<210> SEQ ID NO 105
<211> LENGTH: 7
<212> TYPE: PRT
<213> ORGANISM: Artificial
<220> FEATURE:
<223> OTHER INFORMATION: TF1413-03e034 L Chain CDR 2

<400> SEQUENCE: 105

Leu Ala Ser Asn Arg His Thr
1               5

<210> SEQ ID NO 106
<211> LENGTH: 9

```
<212> TYPE: PRT
<213> ORGANISM: Artificial
<220> FEATURE:
<223> OTHER INFORMATION: TF1413-03e034 L Chain CDR 3

<400> SEQUENCE: 106

Leu Gln His Trp Asn Tyr Pro Leu Thr
1               5

<210> SEQ ID NO 107
<211> LENGTH: 118
<212> TYPE: PRT
<213> ORGANISM: Artificial
<220> FEATURE:
<223> OTHER INFORMATION: TF1413-03e034 H Chain V Region

<400> SEQUENCE: 107

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asn Tyr Gly Tyr Tyr Ala Met Asp Tyr Trp Gly Gln Gly
            100                 105                 110

Thr Ser Val Thr Val Ser
        115

<210> SEQ ID NO 108
<211> LENGTH: 108
<212> TYPE: PRT
<213> ORGANISM: Artificial
<220> FEATURE:
<223> OTHER INFORMATION: TF1413-03e034 L Chain V Region

<400> SEQUENCE: 108

Asp Ile Val Met Ser Gln Ser Pro Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys Arg
            100                 105

<210> SEQ ID NO 109
<211> LENGTH: 449
<212> TYPE: PRT
```

<213> ORGANISM: Artificial
<220> FEATURE:
<223> OTHER INFORMATION: TF1413-03e034 H Chain

<400> SEQUENCE: 109

```
Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asn Tyr Gly Tyr Tyr Ala Met Asp Tyr Trp Gly Gln Gly
            100                 105                 110

Thr Ser Val Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
            210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
```

```
385                 390                 395                 400
Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
                435                 440                 445

Lys

<210> SEQ ID NO 110
<211> LENGTH: 214
<212> TYPE: PRT
<213> ORGANISM: Artificial
<220> FEATURE:
<223> OTHER INFORMATION: TF1413-03e034 L Chain

<400> SEQUENCE: 110

Asp Ile Val Met Ser Gln Ser Pro Lys Phe Met Ser Thr Ser Val Gly
1               5                   10                  15

Asp Arg Val Ser Ile Thr Cys Lys Ala Ser Gln Asn Val Arg Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Asn Glu Cys
        210

<210> SEQ ID NO 111
<211> LENGTH: 354
<212> TYPE: DNA
<213> ORGANISM: Artificial
<220> FEATURE:
<223> OTHER INFORMATION: TF1413-02d028 H Chain V Region Gene

<400> SEQUENCE: 111
caggtgcagc tgaaggagtc aggacctgag ctggagaagc ctggtgcttc agtgaagata      60
tcctgcaagg cttctggtta ctcattcact ggctacaaca tgaactgggt gaagcagagc     120
```

```
aatggaaaga gccttgagtg gattggaaat attgatcctt actatggtgg tactagctac      180
aaccagaagt tcaagggcaa ggccacattg actgtagaca atcctccag cacagcctac       240 atgcagctca agagcctgac atctgaggac tctgcagtct attactgtgc aagaggagac      300
tatagggcgt actactttga ctactggggc caaggcacca ctctcacagt ctcg            354
```

<210> SEQ ID NO 112
<211> LENGTH: 324
<212> TYPE: DNA
<213> ORGANISM: Artificial
<220> FEATURE:
<223> OTHER INFORMATION: TF1413-02d028 L Chain V Region Gene

<400> SEQUENCE: 112

```
gacattcaga tgacccagtc tccaaaattc atgtccacat cagtaggaga cagggtcagc      60
atcacctgca aggccagtca gaatgttcgt actgctgtag cctggtatca acagaaacca     120
gggcagtctc ctaaagcact gatttacttg gcatccaacc ggcacactgg agtccctgat     180
cgcttcacag gcagtggatc tgggacagat ttcactctca ccattagcaa tgtgcaatct    240
gaagacctgg cagattattt ctgtctgcaa cattggaatt atcctctcac gttcggtgct    300
gggaccaagc tggagctgaa acgg                                             324
```

<210> SEQ ID NO 113
<211> LENGTH: 1347
<212> TYPE: DNA
<213> ORGANISM: Artificial
<220> FEATURE:
<223> OTHER INFORMATION: TF1413-02d028 H Chain Gene

<400> SEQUENCE: 113

```
caggtgcagc tgaaggagtc aggacctgag ctggagaagc ctggtgcttc agtgaagata      60
tcctgcaagg cttctggtta ctcattcact ggctacaaca tgaactgggt gaagcagagc     120
aatggaaaga gccttgagtg gattggaaat attgatcctt actatggtgg tactagctac     180
aaccagaagt tcaagggcaa ggccacattg actgtagaca atcctccag cacagcctac     240 atgcagctca agagcctgac atctgaggac tctgcagtct attactgtgc aagaggagac     300
tatagggcgt actactttga ctactggggc caaggcacca ctctcacagt ctcgagcgcc     360
aaaacaacag ccccatcggt ctatccactg gcccctgtgt gtggagatac aactggctcc     420
tcggtgactc taggatgcct ggtcaagggt tatttccctg agccagtgac cttgacctgg     480
aactctggat ccctgtccag tggtgtgcac accttcccag ctgtcctgca gtctgacctc     540
tacaccctca gcagctcagt gactgtaacc tcgagcacct ggcccagcca gtccatcacc     600
tgcaatgtgg cccaccggc aagcagcacc aaggtggaca gaaaattga gccccgggga      660 cccacaatca gccctgtcc tccatgcaaa tgcccagcac ctaacctctt gggtggacca     720
tccgtcttca tcttccctcc aaagatcaag gatgtactca tgatctcccct gagccccata    780 gtcacatgtg tggtggtgga tgtgagcgag gatgacccag atgtccagat cagctggttt     840
gtgaacaacg tggaagtaca cacagctcag acacaaaccc atagagagga ttacaacagt     900
actctccggg tggtcagtgc cctccccatc cagcaccagg actggatgag tggcaaggag     960
ttcaaatgca aggtcaacaa caaagacctc ccagcgccca tcgagagaac catctcaaaa    1020
cccaaagggt cagtaagagc tccacaggta tatgtcttgc ctccaccaga agaagagatg    1080
actaagaaac aggtcactct gacctgcatg gtcacagact tcatgcctga agacatttac    1140
gtggagtgga ccaacaacgg gaaaacagag ctaaactaca agaacactga accagtcctg    1200
```

```
gactctgatg gttcttactt catgtacagc aagctgagag tggaaaagaa gaactgggtg    1260
gaaagaaata gctactcctg ttcagtggtc cacgagggtc tgcacaatca ccacacgact    1320
aagagcttct cccggactcc gggtaaa                                        1347
```

<210> SEQ ID NO 114
<211> LENGTH: 642
<212> TYPE: DNA
<213> ORGANISM: Artificial
<220> FEATURE:
<223> OTHER INFORMATION: TF1413-02d028 H Chain Gene

<400> SEQUENCE: 114

```
gacattcaga tgacccagtc tccaaaattc atgtccacat cagtaggaga cagggtcagc     60
atcacctgca aggccagtca gaatgttcgt actgctgtag cctggtatca acagaaacca    120
gggcagtctc ctaaagcact gatttacttg catccaacc ggcacactgg agtccctgat    180
cgcttcacag gcagtggatc tgggacagat ttcactctca ccattagcaa tgtgcaatct    240
gaagacctgg cagattattt ctgtctgcaa cattggaatt atcctctcac gttcggtgct    300
gggaccaagc tggagctgaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642
```

<210> SEQ ID NO 115
<211> LENGTH: 351
<212> TYPE: DNA
<213> ORGANISM: Artificial
<220> FEATURE:
<223> OTHER INFORMATION: TF1413-02d039 H Chain V Region Gene

<400> SEQUENCE: 115

```
gaagtgaagc tggtggagtc tgggggaggc ttagtgaagc ctggagggtc cctgaaactc     60
tcctgtgcag cctctggatt cgctttcagt agctatgaca tgtcttgggt tcgccagact    120
ccggagaaga ggctggagtg ggtcgcatac attagtagtg gtggtggtag cacctactat    180
ccagacactg tgaagggccg attcaccatc tccagagaca atgccaagaa caccctgtac    240
ctgcaaatga gcagtctgaa gtctgaggac acagccatgt attactgtgc aagaagagga    300
ttacgacgag ctatggacta ctggggtcaa ggaacctcag tcaccgtctc g              351
```

<210> SEQ ID NO 116
<211> LENGTH: 339
<212> TYPE: DNA
<213> ORGANISM: Artificial
<220> FEATURE:
<223> OTHER INFORMATION: TF1413-02d039 L Chain V Region Gene

<400> SEQUENCE: 116

```
gatgttgtga tgacccaaac tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
```

```
agcagagtgg aggctgagga tctgggagtt tatttctgct ctcaaagtac acatgttccg    300
ctcacgttcg gtgctgggac caagctggag ctgaaacgg                           339

<210> SEQ ID NO 117
<211> LENGTH: 1344
<212> TYPE: DNA
<213> ORGANISM: Artificial
<220> FEATURE:
<223> OTHER INFORMATION: TF1413-02d039 H Chain Gene

<400> SEQUENCE: 117
gaagtgaagc tggtggagtc tgggggaggc ttagtgaagc ctggagggtc cctgaaactc    60
tcctgtgcag cctctggatt cgctttcagt agctatgaca tgtcttgggt tcgccagact    120
ccggagaaga ggctgagtg ggtcgcatac attagtagtg gtggtggtag cacctactat    180
ccagacactg tgaagggccg attcaccatc tccagagaca atgccaagaa caccctgtac    240
ctgcaaatga gcagtctgaa gtctgaggac acagccatgt attactgtgc aagaagagga    300
ttacgacgag ctatggacta ctggggtcaa ggaacctcag tcaccgtctc gagcgccaaa    360
acaacagccc catcggtcta tccactggcc cctgtgtgtg agatacaac tggctcctcg    420 gtgactctag gatgctggt caaggggtat ttccctgagc cagtgacctt gacctggaac    480
tctggatccc tgtccagtgg tgtgcacacc ttcccagctg tcctgcagtc tgacctctac    540
accctcagca gctcagtgac tgtaacctcg agcacctggc ccagccagtc catcacctgc    600
aatgtggccc acccggcaag cagcaccaag gtggacaaga aaattgagcc ccggggaccc    660
acaatcaagc cctgtcctcc atgcaaatgc ccagcaccta acctcttggg tggaccatcc    720
gtcttcatct tccctccaaa gatcaaggat gtactcatga tctccctgag ccccatagtc    780
acatgtgtgt ggtggatgt gagcgaggat gacccagatg tccagatcag ctggtttgtg    840
aacaacgtgg aagtacacac agctcagaca caaacccata gagaggatta caacagtact    900
ctccgggtgg tcagtgccct ccccatccag caccaggact ggatgagtgg caaggagttc    960
aaatgcaagg tcaacaacaa agacctccca gcgcccatcg agagaaccat ctcaaaaccc    1020
aaagggtcag taagagctcc acaggtatat gtcttgcctc caccagaaga agagatgact    1080
aagaaacagg tcactctgac ctgcatggtc acagacttca tgcctgaaga catttacgtg    1140
gagtggacca acaacgggaa aacagagcta aactacaaga acactgaacc agtcctggac    1200
tctgatggtt cttacttcat gtacagcaag ctgagagtgg aaaagaagaa ctgggtggaa    1260
agaaatagct actcctgttc agtggtccac gagggtctgc acaatcacca cacgactaag    1320
agcttctccc ggactccggg taaa                                          1344

<210> SEQ ID NO 118
<211> LENGTH: 657
<212> TYPE: DNA
<213> ORGANISM: Artificial
<220> FEATURE:
<223> OTHER INFORMATION: TF1413-02d039 L Chain Gene

<400> SEQUENCE: 118
gatgttgtga tgacccaaac tccactctcc ctgcctgtca gtcttggaga tcaagcctcc    60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
```

```
ctcacgttcg gtgctgggac caagctggag ctgaaacggg ctgatgctgc accaactgta    360
tccatcttcc caccatccag tgagcagtta acatctggag gtgcctcagt cgtgtgcttc    420
ttgaacaact tctaccccaa agacatcaat gtcaagtgga agattgatgg cagtgaacga    480
caaaatggcg tcctgaacag ttggactgat caggacagca aagacagcac ctacagcatg    540
agcagcaccc tcacgttgac caaggacgag tatgaacgac ataacagcta tacctgtgag    600
gccactcaca agacatcaac ttcacccatt gtcaagagct caacaggaa tgagtgt       657
```

<210> SEQ ID NO 119
<211> LENGTH: 345
<212> TYPE: DNA
<213> ORGANISM: Artificial
<220> FEATURE:
<223> OTHER INFORMATION: TF1413-02e004 H Chain V Region Gene
<400> SEQUENCE: 119

```
caggtccagc tgcagcagtc tggggctgag cttgtgaagc ctggggctcc agtgaagctg    60
tcctgcaagg cttctggcta caccttcacc agctactgga tgaactgggt gaagcagagg   120
cctggacgag gccctgagtg gattggaagg attgatcctt cgatagtga aactcactac    180 aatcaaaagt tcaaggacga ggccacactg actgtagaca atcctccag cacagcctac   240 atccaactca gcagcctgac atctgaggac tctgcggtct attactgtgc aagagggtac    300
tatgctatgg actactgggg tcaaggaacc tcagtcaccg tctcg                    345
```

<210> SEQ ID NO 120
<211> LENGTH: 321
<212> TYPE: DNA
<213> ORGANISM: Artificial
<220> FEATURE:
<223> OTHER INFORMATION: TF1413-02e004 L Chain V Region Gene
<400> SEQUENCE: 120

```
gacattgtgc tgacccaatc tcccaaattc atgtccacat cagtaggaga cagggtcagc    60
atcacctgca aggccagtca ggatgtgagt actgctgtag cctggtatca acagaaacca   120
ggacaatctc ctaaaactact gatttactca gcatcctacc ggtacactgg agtccctgat    180
cgcttcactg gcagtggatc tgggacggat ttcactttca ccatcagcag tgtgcaggct   240
gaagacctgg cagtttatta ctgtcagcaa cattatagta ctccgacgtt cggtggaggc    300
accaagctgg aaatcaaacg g                                              321
```

<210> SEQ ID NO 121
<211> LENGTH: 1338
<212> TYPE: DNA
<213> ORGANISM: Artificial
<220> FEATURE:
<223> OTHER INFORMATION: TF1413-02e004 H Chain Gene
<400> SEQUENCE: 121

```
caggtccagc tgcagcagtc tggggctgag cttgtgaagc ctggggctcc agtgaagctg    60
tcctgcaagg cttctggcta caccttcacc agctactgga tgaactgggt gaagcagagg   120
cctggacgag gccctgagtg gattggaagg attgatcctt cgatagtga aactcactac    180 aatcaaaagt tcaaggacga ggccacactg actgtagaca atcctccag cacagcctac    240 atccaactca gcagcctgac atctgaggac tctgcggtct attactgtgc aagagggtac    300
tatgctatgg actactgggg tcaaggaacc tcagtcaccg tctcgagcgc caaaacaaca    360
```

```
gccccatcgg tctatccact ggccctgtg tgtggagata caactggctc ctcggtgact    420
ctaggatgcc tggtcaaggg ttatttccct gagccagtga ccttgacctg gaactctgga    480
tccctgtcca gtggtgtgca caccttccca gctgtcctgc agtctgacct ctacaccctc    540
agcagctcag tgactgtaac ctcgagcacc tggcccagcc agtccatcac ctgcaatgtg    600
gcccacccgg caagcagcac caaggtggac aagaaaattg agccccgggg acccacaatc    660
aagccctgtc ctccatgcaa atgcccagca cctaacctct ggggtggacc atccgtcttc    720
atcttccctc caaagatcaa ggatgtactc atgatctccc tgagccccat agtcacatgt    780
gtggtggtgg atgtgagcga ggatgaccca gatgtccaga tcagctggtt tgtgaacaac    840
gtggaagtac acacagctca gacacaaacc catagagagg attacaacag tactctccgg    900
gtggtcagtg ccctccccat ccagcaccag gactggatga gtggcaagga gttcaaatgc    960
aaggtcaaca acaaagacct cccagcgccc atcgagagaa ccatctcaaa acccaagggg    1020
tcagtaagag ctccacaggt atatgtcttg cctccaccag aagaagagat gactaagaaa    1080
caggtcactc tgacctgcat ggtcacagac ttcatgcctg aagacattta cgtggagtgg    1140
accaacaacg ggaaaacaga gctaaactac aagaacactg aaccagtcct ggactctgat    1200
ggttcttact tcatgtacag caagctgaga gtggaaaaga gaactgggt ggaaagaaat    1260 agctactcct gttcagtggt ccacgagggt ctgcacaatc accacgac taagagcttc    1320 tcccggactc cgggtaaa                                                 1338

<210> SEQ ID NO 122
<211> LENGTH: 639
<212> TYPE: DNA
<213> ORGANISM: Artificial
<220> FEATURE:
<223> OTHER INFORMATION: TF1413-02e004 L Chain Gene

<400> SEQUENCE: 122
gacattgtgc tgacccaatc tcccaaattc atgtccacat cagtaggaga cagggtcagc    60
atcacctgca aggccagtca ggatgtgagt actgctgtag cctggtatca acagaaacca    120
ggacaatctc ctaaaactac tgatttactca gcatcctacc ggtacactgg agtccctgat    180
cgcttcactg gcagtggatc tgggacggat ttcactttca ccatcagcag tgtgcaggct    240
gaagacctgg cagtttatta ctgtcagcaa cattatagta ctccgacgtt cggtggaggc    300
accaagctgg aaatcaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg aagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600 acttcacccca ttgtcaagag cttcaacagg aatgagtgt                         639

<210> SEQ ID NO 123
<211> LENGTH: 360
<212> TYPE: DNA
<213> ORGANISM: Artificial
<220> FEATURE:
<223> OTHER INFORMATION: TF1413-02e014 H Chain V Region Gene

<400> SEQUENCE: 123
caggtgcagc tgaagcagtc aggggcagag cttgtgaggt caggggcctc agtcaagttg    60
tcctgcacag cttctggctt caacattaaa gactactata tgcactgggt gaagcagagg    120
```

```
cctgaacagg gcctggagtg gattggatgg attgatcctg agaatggtga tactgaatat    180
gccccgaagt tccagggcaa ggccactatg actgcagaca catcctccaa cacagcctac    240
ctgcagctca gcagcctgac atctgaggac actgccgtct attactgtaa tgcaggctac    300
tatgattacg acggctatgc tatggactac tggggtcaag gaacctcagt caccgtctcg    360
```

<210> SEQ ID NO 124
<211> LENGTH: 324
<212> TYPE: DNA
<213> ORGANISM: Artificial
<220> FEATURE:
<223> OTHER INFORMATION: TF1413-02e014 L Chain V Region Gene

<400> SEQUENCE: 124

```
gacattgtgc tgacacagtc tcccaaattc atgtccacat cagtaggaga cagggtcagc     60
atcacctgca aggccagtca ggatgtgggt actgctgtag cctggtatca acagaaacca    120
gggcaatctc ctaaactact gatttactgg gcatccaccc ggcacactgg agtcccgat     180 cgcttcacag gcagtggatc tgggacagat ttcactctca ccattagcaa tgtgcagtct    240
gaagacttgg cagattattt ctgtcagcaa tatagcagct atcctctgac gttcggtgga    300
ggcaccaagc tggaaatcaa acgg                                           324
```

<210> SEQ ID NO 125
<211> LENGTH: 1353
<212> TYPE: DNA
<213> ORGANISM: Artificial
<220> FEATURE:
<223> OTHER INFORMATION: TF1413-02e014 H Chain Gene

<400> SEQUENCE: 125

```
caggtgcagc tgaagcagtc aggggcagag cttgtgaggt caggggcctc agtcaagttg     60
tcctgcacag cttctggctt caacattaaa gactactata tgcactgggt gaagcagagg    120
cctgaacagg gcctggagtg gattggatgg attgatcctg agaatggtga tactgaatat    180
gccccgaagt tccagggcaa ggccactatg actgcagaca catcctccaa cacagcctac    240
ctgcagctca gcagcctgac atctgaggac actgccgtct attactgtaa tgcaggctac    300
tatgattacg acggctatgc tatggactac tggggtcaag gaacctcagt caccgtctcg    360
agcgccaaaa aaacagcccc atcggtctat ccactggccc ctgtgtgtgg agatacaact    420
ggctcctcgg tgactctagg atgcctggtc aagggttatt tccctgagcc agtgaccttg    480
acctggaact ctggatccct gtccagtggt gtgcacacct tcccagctgt cctgcagtct    540
gacctctaca ccctcagcag ctcagtgact gtaacctcga gcacctggcc cagccagtcc    600
atcacctgca atgtggccca cccggcaagc agtaccaagg tggacaagaa aattgagccc    660
cggggaccca caatcaagcc ctgtcctcca tgcaaatgcc cagcacctaa cctcttgggt    720
ggaccatccg tcttcatctt ccctccaaag atcaaggatg tactcatgat ctccctgagc    780
cccatagtca catgtgtggt ggtggatgtg agcgaggatg acccagatgt ccagatcagc    840
tggtttgtga acaacgtgga agtacacaca gctcagacac aaacccatag agaggattac    900
aacagtactc tccgggtggt cagtgccctc cccatccagc accaggactg gatgagtggc    960
aaggagttca atgcaaggt caacaacaaa gacctcccag cgcccatcga gagaaccatc   1020
tcaaaaccca aagggtcagt aagagctcca caggtatatg tcttgcctcc accagaagaa   1080
gagatgacta agaaacaggt cactctgacc tgcatggtca cagacttcat gcctgaagac   1140
```

-continued

| | |
|---|---|
| atttacgtgg agtggaccaa caacgggaaa acagagctaa actacaagaa cactgaacca | 1200 |
| gtcctggact ctgatggttc ttacttcatg tacagcaagc tgagagtgga aaagaagaac | 1260 |
| tgggtggaaa gaaatagcta ctcctgttca gtggtccacg agggtctgca caatcaccac | 1320 |
| acgactaaga gcttctcccg gactccgggt aaa | 1353 |

<210> SEQ ID NO 126
<211> LENGTH: 642
<212> TYPE: DNA
<213> ORGANISM: Artificial
<220> FEATURE:
<223> OTHER INFORMATION: TF1413-02e014 L Chain Gene

<400> SEQUENCE: 126

| | |
|---|---|
| gacattgtgc tgacacagtc tcccaaattc atgtccacat cagtaggaga cagggtcagc | 60 |
| atcacctgca aggccagtca ggatgtgggt actgctgtag cctggtatca acagaaacca | 120 |
| gggcaatctc ctaaactact gatttactgg gcatccaccc ggcacactgg agtcccgat | 180 |
| cgcttcacag gcagtggatc tgggacagat ttcactctca ccattagcaa tgtgcagtct | 240 |
| gaagacttgg cagattattt ctgtcagcaa tatagcagct atcctctgac gttcggtgga | 300 |
| ggcaccaagc tggaaatcaa acgggctgat gctgcaccaa ctgtatccat cttcccacca | 360 |
| tccagtgagc agttaacatc tggaggtgcc tcagtcgtgt gcttcttgaa caacttctac | 420 |
| cccaaagaca tcaatgtcaa gtggaagatt gatggcagtg aacgacaaaa tggcgtcctg | 480 |
| aacagttgga ctgatcagga cagcaaagac agcacctaca gcatgagcag cacccctcacg | 540 |
| ttgaccaagg acgagtatga acgacataac agctatacct gtgaggccac tcacaagaca | 600 |
| tcaacttcac ccattgtcaa gagcttcaac aggaatgagt gt | 642 |

<210> SEQ ID NO 127
<211> LENGTH: 351
<212> TYPE: DNA
<213> ORGANISM: Artificial
<220> FEATURE:
<223> OTHER INFORMATION: TF1413-02e030 H Chain V Region Gene

<400> SEQUENCE: 127

| | |
|---|---|
| gaggttcagc ttcagcagtc tggggctgag cttgtgaggc caggggcctt agtcaagttg | 60 |
| tcctgcaaag cttctggctt caacattaaa gactactata tgcactgggt gaagcagagg | 120 |
| cctgaacagg gcctggagtg gattggatgg attgatcctg agaatggtaa cactatatat | 180 |
| gacccgaagt tccagggcaa ggccagtata acagcagaca catcctccaa cacagcctac | 240 |
| ctgcagctca gcagcctgac atctgaggac actgccgtct attactgtgc tatatctact | 300 |
| atgattacga cccttgacta ctggggccaa ggcaccactc tcacagtctc g | 351 |

<210> SEQ ID NO 128
<211> LENGTH: 342
<212> TYPE: DNA
<213> ORGANISM: Artificial
<220> FEATURE:
<223> OTHER INFORMATION: TF1413-02e030 L Chain V Region Gene

<400> SEQUENCE: 128

| | |
|---|---|
| gacatccaga tgacccagtc tccatcctcc ctggctatgt cagtagggca gaaggtcact | 60 |
| atgagctgca gtccagtca gagccttta aatagtagca atcaaaagaa ctatttggcc | 120 |
| tggtaccagc agaaaccagg acagtctcct aaacttctgg tatactttgc atccactagg | 180 |
| gaatctgggg tccctgatcg cttcataggc agtggatctg ggacagattt cactcttacc | 240 |

```
atcagcagtg tgcaggctga agacctggca gattacttct gtcagcaaca ttatagcact    300
ccgctcacgt tcggtgctgg gaccaagctg gagctgaaac gg                        342
```

<210> SEQ ID NO 129
<211> LENGTH: 1344
<212> TYPE: DNA
<213> ORGANISM: Artificial
<220> FEATURE:
<223> OTHER INFORMATION: TF1413-02e030 H Chain Gene

<400> SEQUENCE: 129

```
gaggttcagc ttcagcagtc tggggctgag cttgtgaggc caggggcctt agtcaagttg     60
tcctgcaaag cttctggctt caacattaaa gactactata tgcactgggt gaagcagagg    120
cctgaacagg gcctggagtg gattggatgg attgatcctg agaatggtaa cactatatat    180
gacccgaagt tccagggcaa ggccagtata acagcagaca tcctccaa cacagcctac     240 ctgcagctca gcagcctgac atctgaggac actgccgtct attactgtgc tatatctact    300
atgattacga cccttgacta ctggggccaa ggcaccactc tcacagtctc gagcgccaaa    360
acaacagccc catcggtcta tccactggcc cctgtgtgtg agatacaac tggctcctcg     420 gtgactctag gatgcctggt caagggttat ttccctgagc cagtgacctt gacctggaac    480
tctggatccc tgtccagtgg tgtgcacacc ttcccagctg tcctgcagtc tgacctctac    540
accctcagca gctcagtgac tgtaacctcg agcacctggc ccagccagtc catcacctgc    600
aatgtggccc accggcaag cagcaccaag gtggacaaga aaattgagcc cggggaccc     660 acaatcaagc cctgtcctcc atgcaaatgc ccagcaccta acctcttggg tggaccatcc    720
gtcttcatct tccctccaaa gatcaaggat gtactcatga tctccctgag ccccatagtc    780
acatgtgtgg tggtggatgt gagcgaggat gacccagatg tccagatcag ctggtttgtg    840
aacaacgtgg aagtacacac agctcagaca caaacccata gagaggatta caacagtact    900
ctccgggtgg tcagtgccct ccccatccag caccaggact ggatgagtgg caaggagttc    960
aaatgcaagg tcaacaacaa agacctccca gcgcccatcg agaaccat ctcaaaaccc     1020 aaagggtcag taagagctcc acaggtatat gtcttgcctc caccagaaga agagatgact    1080
aagaaacagg tcactctgac ctgcatggtc acagacttca tgcctgaaga catttacgtg    1140
gagtggacca caacgggaa acagagcta actacaaga cactgaacc agtcctggac      1200 tctgatggtt cttacttcat gtacagcaag ctgagagtgg aaaagaagaa ctgggtggaa    1260
agaaatagct actcctgttc agtggtccac gagggtctgc acaatcacca cacgactaag    1320
agcttctccc ggactccggg taaa                                           1344
```

<210> SEQ ID NO 130
<211> LENGTH: 660
<212> TYPE: DNA
<213> ORGANISM: Artificial
<220> FEATURE:
<223> OTHER INFORMATION: TF1413-02e030 L Chain Gene

<400> SEQUENCE: 130

```
gacatccaga tgacccagtc tccatcctcc ctggctatgt cagtagggca gaaggtcact     60
atgagctgca gtccagtca gagccttta aatagtagca tcaaaagaa ctatttggcc      120 tggtaccagc agaaaccagg acagtctcct aaacttctgg tatactttgc atccactagg    180
gaatctgggg tccctgatcg cttcatagc agtggatctg ggacagattt cactcttacc    240
```

```
atcagcagtg tgcaggctga agacctggca gattacttct gtcagcaaca ttatagcact      300
ccgctcacgt tcggtgctgg gaccaagctg gagctgaaac gggctgatgc tgcaccaact      360
gtatccatct tcccaccatc cagtgagcag ttaacatctg gaggtgcctc agtcgtgtgc      420
ttcttgaaca acttctaccc caaagacatc aatgtcaagt ggaagattga tggcagtgaa      480
cgacaaaatg gcgtcctgaa cagttggact gatcaggaca gcaaagacag cacctacagc      540
atgagcagca ccctcacgtt gaccaaggac gagtatgaac gacataacag ctatacctgt      600
gaggccactc acaagacatc aacttcaccc attgtcaaga gcttcaacag gaatgagtgt      660
```

<210> SEQ ID NO 131
<211> LENGTH: 348
<212> TYPE: DNA
<213> ORGANISM: Artificial
<220> FEATURE:
<223> OTHER INFORMATION: TF1413-02e040 H Chain V Region Gene

<400> SEQUENCE: 131

```
gaagtgatgc tggtggagtc tggacctgag ctggtgaagc ctggagcttc aatgaagata       60
tcctgcaagg cttctggtta ctcattcact ggctacacca tgaactgggt gaagcagagc      120
catggaaaga accttgagtg gattggactt attaatcctt acaatggtgg tactagctac      180
aaccagaatt ttaagggcaa ggccacatta actgtagaca gtcatccag cacagcctac      240 atggagctcc tcagtctgac atctgaggac tctgcagtct attactgtgc aagagggtac      300
tacggtcgct ttgactactg gggccaaggc accactctca cagtctcg               348
```

<210> SEQ ID NO 132
<211> LENGTH: 324
<212> TYPE: DNA
<213> ORGANISM: Artificial
<220> FEATURE:
<223> OTHER INFORMATION: TF1413-02e040 L Chain V Region Gene

<400> SEQUENCE: 132

```
gacatcttgc tgactcagtc tccaaaattc atgtccacat cagtaggaga cagggtcagc       60
atcacctgca aggccagtca gaatgttcgt actgctgtag cctggtatca acagaaacca      120
gggcagtctc ctaaagcact gatttacttg gcatccaacc ggcacactgg agtccctgat      180
cgcttcacag gcagtggatc tgggacagat ttcactctca ccattagcaa tgtgcaatct      240
gaagacctgg cagattattt ctgtctgcaa cattggaatt atcctctcac gttcggtgct      300
gggaccaagc tggagctgaa acgg                                              324
```

<210> SEQ ID NO 133
<211> LENGTH: 1341
<212> TYPE: DNA
<213> ORGANISM: Artificial
<220> FEATURE:
<223> OTHER INFORMATION: TF1413-02e040 H Chain Gene

<400> SEQUENCE: 133

```
gaagtgatgc tggtggagtc tggacctgag ctggtgaagc ctggagcttc aatgaagata       60
tcctgcaagg cttctggtta ctcattcact ggctacacca tgaactgggt gaagcagagc      120
catggaaaga accttgagtg gattggactt attaatcctt acaatggtgg tactagctac      180
aaccagaatt ttaagggcaa ggccacatta actgtagaca gtcatccag cacagcctac      240 atggagctcc tcagtctgac atctgaggac tctgcagtct attactgtgc aagagggtac      300
tacggtcgct ttgactactg gggccaaggc accactctca cagtctcgag cgccaaaaca      360
```

```
acagccccat cggtctatcc actggcccct gtgtgtggag atacaactgg ctcctcggtg      420
actctaggat gcctggtcaa gggttatttc cctgagccag tgaccttgac ctggaactct      480
ggatccctgt ccagtggtgt gcacaccttc ccagctgtcc tgcagtctga cctctacacc      540
ctcagcagct cagtgactgt aacctcgagc acctggccca gccagtccat cacctgcaat      600
gtggcccacc cggcaagcag caccaaggtg gacaagaaaa ttgagccccg gggacccaca      660
atcaagccct gtcctccatg caaatgccca gcacctaacc tcttgggtgg accatccgtc      720
ttcatcttcc ctccaaagat caaggatgta ctcatgatct ccctgagccc catagtcaca      780
tgtgtggtgg tggatgtgag cgaggatgac ccagatgtcc agatcagctg gtttgtgaac      840
aacgtggaag tacacacagc tcagacacaa acccatagag aggattacaa cagtactctc      900
cgggtggtca gtgccctccc catccagcac caggactgga tgagtggcaa ggagttcaaa      960
tgcaaggtca acaacaaaga cctcccagcg cccatcgaga gaaccatctc aaaacccaaa     1020
gggtcagtaa gagctccaca ggtatatgtc ttgcctccac cagaagaaga gatgactaag     1080
aaacaggtca ctctgacctg catggtcaca gacttcatgc ctgaagacat ttacgtggag     1140
tggaccaaca acgggaaaac agagctaaac tacaagaaca ctgaaccagt cctggactct     1200
gatggttctt acttcatgta cagcaagctg agagtggaaa agaagaactg ggtggaaaga     1260
aatagctact cctgttcagt ggtccacgag ggtctgcaca atcaccacac gactaagagc     1320
ttctcccgga ctccgggtaa a                                               1341

<210> SEQ ID NO 134
<211> LENGTH: 642
<212> TYPE: DNA
<213> ORGANISM: Artificial
<220> FEATURE:
<223> OTHER INFORMATION: TF1413-02e040 L Chain Gene

<400> SEQUENCE: 134
gacatcttgc tgactcagtc tccaaaattc atgtccacat cagtaggaga cagggtcagc       60
atcacctgca aggccagtca gaatgttcgt actgctgtag cctggtatca acagaaacca      120
gggcagtctc ctaaagcact gatttacttg gcatccaacc ggcacactgg agtccctgat      180
cgcttcacag gcagtggatc tgggacagat ttcactctca ccattagcaa tgtgcaatct      240
gaagacctgg cagattattt ctgtctgcaa cattggaatt atcctctcac gttcggtgct      300
gggaccaagc tggagctgaa acgggctgat gctgcaccaa ctgtatccat cttcccacca      360
tccagtgagc agttaacatc tggaggtgcc tcagtcgtgt gcttcttgaa caacttctac      420
cccaaagaca tcaatgtcaa gtggaagatt gatggcagtg aacgacaaaa tggcgtcctg      480
aacagttgga ctgatcagga cagcaaagac agcacctaca gcatgagcag cacccttacg      540
ttgaccaagg acgagtatga acgacataac agctatacct gtgaggccac tcacaagaca      600
tcaacttcac ccattgtcaa gagcttcaac aggaatgagt gt                         642

<210> SEQ ID NO 135
<211> LENGTH: 345
<212> TYPE: DNA
<213> ORGANISM: Artificial
<220> FEATURE:
<223> OTHER INFORMATION: TF1413-03e001 H Chain V Region Gene

<400> SEQUENCE: 135
caggtgcagc tgaagcagtc aggacctgag ctggtgaagc ctggggcttc agtgaagata       60
```

| | |
|---|---|
| tcctgcaagg cttctggtta ctcattcact ggctactaca tgcactgggt gaagcaaagc | 120 |
| catgtaaaga gccttgagtg gattggacgt attaatcctt acaatggtgc tactagctac | 180 |
| aaccagaatt tcaaggacaa ggccagcttg actgtagata agtcctccag cacagcctac | 240 |
| atggagctcc acagcctgac atctgaggac tctgcagtct attactgtgc aagaaactac | 300 |
| ggctactttg actactgggg ccaaggcacc actctcacag tctcg | 345 |

<210> SEQ ID NO 136
<211> LENGTH: 324
<212> TYPE: DNA
<213> ORGANISM: Artificial
<220> FEATURE:
<223> OTHER INFORMATION: TF1413-03e001 L Chain V Region Gene

<400> SEQUENCE: 136

| | |
|---|---|
| gacatcaaga tgacccagtc tccaaaattc atgtccacat cagtaggaga cagggtcagc | 60 |
| gtcacctgcg aggccagtca gaatgtggat aataatgtag tctggtatca acagaaacca | 120 |
| gggcaatctc ctaaagcact gatttactcg gcatcctacc ggtacagtgg agtccctgat | 180 |
| cgcttcacag gcagtggatc tgggacagat ttcactctca ccatcagcaa tgtgcagtct | 240 |
| gaagacttgg cagagtattt ctgtcagcaa tataacagct atcctctcac gttcggtgct | 300 |
| gggaccaagt tggaaataaa acgg | 324 |

<210> SEQ ID NO 137
<211> LENGTH: 1338
<212> TYPE: DNA
<213> ORGANISM: Artificial
<220> FEATURE:
<223> OTHER INFORMATION: TF1413-03e001 H Chain Gene

<400> SEQUENCE: 137

| | |
|---|---|
| caggtgcagc tgaagcagtc aggacctgag ctggtgaagc ctggggcttc agtgaagata | 60 |
| tcctgcaagg cttctggtta ctcattcact ggctactaca tgcactgggt gaagcaaagc | 120 |
| catgtaaaga gccttgagtg gattggacgt attaatcctt acaatggtgc tactagctac | 180 |
| aaccagaatt tcaaggacaa ggccagcttg actgtagata agtcctccag cacagcctac | 240 |
| atggagctcc acagcctgac atctgaggac tctgcagtct attactgtgc aagaaactac | 300 |
| ggctactttg actactgggg ccaaggcacc actctcacag tctcgagcgc caaaacaaca | 360 |
| gccccatcgg tctatccact ggcccctgtg tgtggagata caactggctc ctcggtgact | 420 |
| ctaggatgcc tggtcaaggg ttatttccct gagccagtga ccttgacctg aactctggat | 480 |
| ccctgtccag tggtgtgca ccttcccag ctgtcctgc agtctgacct ctacaccctc | 540 |
| agcagctcag tgactgtaac ctcgagcacc tggcccagcc agtccatcac ctgcaatgtg | 600 |
| gcccacccgg caagcagcac caaggtggac aagaaaattg agcccggggg acccacaatc | 660 |
| aagccctgtc ctccatgcaa atgcccagca cctaacctct gggtggacc atccgtcttc | 720 |
| atcttccctc caaagatcaa ggatgtactc atgatctccc tgagccccat agtcacatgt | 780 |
| gtggtggtgg atgtgagcga ggatgaccca gatgtccaga tcagctggtt tgtgaacaac | 840 |
| gtggaagtac acacagctca gacacaaacc catagagagg attacaacag tactctccgg | 900 |
| gtggtcagtg ccctccccat ccagcaccag gactggatga gtgcaagga gttcaaatgc | 960 |
| aaggtcaaca acaaagacct cccagcgccc atcgagagaa ccatctcaaa acccaagggg | 1020 |
| tcagtaagag ctccacaggt atatgtcttg cctccaccag aagaagagat gactaagaaa | 1080 |
| caggtcactc tgacctgcat ggtcacagac ttcatgcctg aagacattta cgtggagtgg | 1140 |

```
accaacaacg ggaaaacaga gctaaactac aagaacactg aaccagtcct ggactctgat    1200
ggttcttact tcatgtacag caagctgaga gtggaaaaga agaactgggt ggaaagaaat    1260
agctactcct gttcagtggt ccacgagggt ctgcacaatc accacacgac taagagcttc    1320
tcccggactc cgggtaaa                                                  1338

<210> SEQ ID NO 138
<211> LENGTH: 642
<212> TYPE: DNA
<213> ORGANISM: Artificial
<220> FEATURE:
<223> OTHER INFORMATION: TF1413-03e001 L Chain Gene

<400> SEQUENCE: 138
gacatcaaga tgacccagtc tccaaaattc atgtccacat cagtaggaga cagggtcagc     60
gtcacctgcg aggccagtca gaatgtggat aataatgtag tctggtatca acagaaacca    120
gggcaatctc ctaaagcact gatttactcg gcatcctacc ggtacagtgg agtccctgat    180
cgcttcacag gcagtggatc tgggacagat ttcactctca ccatcagcaa tgtgcagtct    240
gaagacttgg cagagtattt ctgtcagcaa tataacagct atcctctcac gttcggtgct    300
gggaccaagt tggaaataaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

<210> SEQ ID NO 139
<211> LENGTH: 345
<212> TYPE: DNA
<213> ORGANISM: Artificial
<220> FEATURE:
<223> OTHER INFORMATION: TF1413-03e004 H Chain V Region Gene

<400> SEQUENCE: 139
caggtgcagc tgaagcagtc aggggctgag cttgtgaagc ctggggctcc agtgaagctg     60
tcctgcaagg cttctggcta caccttcacc agctactgga tgaactgggt gaagcagagg    120
cctggacgag gcctcgagtg gattggaagg attgatcctt ccgatagtga aactcactac    180
aatcaaaagt tcaaggacaa ggccacactg actgtagaca atcctccag cacagcctac    240 atccaactca gcagcctgac atctgaggac tctgcggtct attactgtgc aagagggtac    300
tacggtagta actactgggg ccaaggcacc actctcacag tctcg                    345

<210> SEQ ID NO 140
<211> LENGTH: 324
<212> TYPE: DNA
<213> ORGANISM: Artificial
<220> FEATURE:
<223> OTHER INFORMATION: TF1413-03e004 L Chain V Region Gene

<400> SEQUENCE: 140
gacatcaaga tgacccagtc tccaaaattc atgtccacat cagtaggaga cagggtcagc     60
gtcacctgca aggccagtca gaatgtgggt actaatgtag cctggtatca acagaaacca    120
gggcaatctc ctaaagcact gatttactcg gcatcctacc ggtacagtgg agtccctgat    180
```

| | |
|---|---|
| cgcttcacag gcagtggatc tgggacagat ttcactctca ccatcagcaa tgtgcagtct | 240 |
| gaagacttgg cagagtattt ctgtcagcaa tataacagct atcctctcac gttcggtgct | 300 |
| gggaccaagc tggagctgaa acgg | 324 |

<210> SEQ ID NO 141
<211> LENGTH: 1338
<212> TYPE: DNA
<213> ORGANISM: Artificial
<220> FEATURE:
<223> OTHER INFORMATION: TF1413-03e004 H Chain Gene

<400> SEQUENCE: 141

| | |
|---|---|
| caggtgcagc tgaagcagtc aggggctgag cttgtgaagc ctggggctcc agtgaagctg | 60 |
| tcctgcaagg cttctggcta caccttcacc agctactgga tgaactgggt gaagcagagg | 120 |
| cctggacgag gccctcgagtg gattggaagg attgatcctt ccgatagtga aactcactac | 180 |
| aatcaaaagt tcaaggacaa ggccacactg actgtagaca atcctccag cacagcctac | 240 |
| atccaactca gcagcctgac atctgaggac tctgcggtct attactgtgc aagagggtac | 300 |
| tacggtagta actactgggg ccaaggcacc actctcacag tctcgagcgc caaaacaaca | 360 |
| gccccatcgg tctatccact ggcccctgtg tgtggagata caactggctc ctcggtgact | 420 |
| ctaggatgcc tggtcaaggg ttatttccct gagccagtga ccttgacctg gaactctgga | 480 |
| tccctgtcca gtggtgtgca caccttccca gctgtcctgc agtctgacct ctacaccctc | 540 |
| agcagctcag tgactgtaac ctcgagcacc tggcccagcc agtccatcac ctgcaatgtg | 600 |
| gcccacccgg caagcagcac caaggtggac aagaaaattg agccccgggg acccacaatc | 660 |
| aagccctgtc ctccatgcaa atgcccagca cctaacctct gggtggacc atccgtcttc | 720 |
| atcttccctc caaagatcaa ggatgtactc atgatctccc tgagccccat agtcacatgt | 780 |
| gtggtggtgg atgtgagcga ggatgaccca gatgtccaga tcagctggtt tgtgaacaac | 840 |
| gtggaagtac acacagctca gacacaaacc catagagagg attacaacag tactctccgg | 900 |
| gtggtcagtg ccctccccat ccagcaccag gactggatga gtggcaagga gttcaaatgc | 960 |
| aaggtcaaca caaagacct cccagcgccc atcgagagaa ccatctcaaa acccaaaggg | 1020 |
| tcagtaagag ctccacaggt atatgtcttg cctccaccag aagaagagat gactaagaaa | 1080 |
| caggtcactc tgacctgcat ggtcacagac ttcatgcctg aagacattta cgtggagtgg | 1140 |
| accaacaacg ggaaaacaga gctaaactac aagaacactg aaccagtcct ggactctgat | 1200 |
| ggttcttact tcatgtacag caagctgaga gtggaaaaga gaactgggt ggaaagaaat | 1260 |
| agctactcct gttcagtggt ccacgagggt ctgcacaatc accacgac taagagcttc | 1320 |
| tcccggactc cgggtaaa | 1338 |

<210> SEQ ID NO 142
<211> LENGTH: 642
<212> TYPE: DNA
<213> ORGANISM: Artificial
<220> FEATURE:
<223> OTHER INFORMATION: TF1413-03e004 L Chain Gene

<400> SEQUENCE: 142

| | |
|---|---|
| gacatcaaga tgacccagtc tccaaaattc atgtccacat cagtaggaga cagggtcagc | 60 |
| gtcacctgca aggccagtca gaatgtgggt actaatgtag cctggtatca acagaaacca | 120 |
| gggcaatctc ctaaagcact gatttactcg gcatcctacc ggtacagtgg agtccctgat | 180 |
| cgcttcacag gcagtggatc tgggacagat ttcactctca ccatcagcaa tgtgcagtct | 240 |

```
gaagacttgg cagagtattt ctgtcagcaa tataacagct atcctctcac gttcggtgct    300
gggaccaagc tggagctgaa acgggctgat gctgcaccaa ctgtatccat cttcccacca    360
tccagtgagc agttaacatc tggaggagcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                      642

<210> SEQ ID NO 143
<211> LENGTH: 360
<212> TYPE: DNA
<213> ORGANISM: Artificial
<220> FEATURE:
<223> OTHER INFORMATION: TF1413-03e005 H Chain V Region Gene

<400> SEQUENCE: 143
caggtgcagc tgaaggagtc aggggcagag cttgtgaggt caggggcctc agtcaagttg     60
tcctgcacag cttctggctt caacattaaa gactactata tgcactgggt gaagcagagg    120
cctgaacagg gcctggagtg gattggatgg attgatcctg agaatggtga tactgaatat    180
gccccgaagt tccagggcaa ggccactatg actgcagaca catcctccaa cacagcctac    240
ctgcagctca gcagcctgac atctgaggac actgccgtct attactgtaa tgccttctac    300
tatgattacg acgggtatgc tatggactac tggggtcaag gaacctcagt caccgtctcg    360

<210> SEQ ID NO 144
<211> LENGTH: 324
<212> TYPE: DNA
<213> ORGANISM: Artificial
<220> FEATURE:
<223> OTHER INFORMATION: TF1413-03e005 L Chain V Region Gene

<400> SEQUENCE: 144
gatgttgtga tgacccaaac tccatcctcc ttatctgcct ctctgggaga aagagtcagt     60
ctcacttgtc gggcaagtca ggaaattagt ggttacttaa gctggcttca gcagaaacca    120
gatggaacta ttaaacgcct gatctacgcc gcatccactt tagattctgg tgtcccaaaa    180
aggttcagtg gcagtaggtc tgggtcagat tattctctca ccatcagcag ccttgagtct    240
gaagattttg cagactatta ctgtctacaa tatgctagtt atccgctcac gttcggtgct    300
gggaccaagc tggagctgaa acgg                                           324

<210> SEQ ID NO 145
<211> LENGTH: 1353
<212> TYPE: DNA
<213> ORGANISM: Artificial
<220> FEATURE:
<223> OTHER INFORMATION: TF1413-03e005 H Chain Gene

<400> SEQUENCE: 145
caggtgcagc tgaaggagtc aggggcagag cttgtgaggt caggggcctc agtcaagttg     60
tcctgcacag cttctggctt caacattaaa gactactata tgcactgggt gaagcagagg    120
cctgaacagg gcctggagtg gattggatgg attgatcctg agaatggtga tactgaatat    180
gccccgaagt tccagggcaa ggccactatg actgcagaca catcctccaa cacagcctac    240
ctgcagctca gcagcctgac atctgaggac actgccgtct attactgtaa tgccttctac    300
```

```
tatgattacg acgggtatgc tatggactac tggggtcaag gaacctcagt caccgtctcg      360
agggccaaaa caacagcccc atcggtctat ccactggccc ctgtgtgtgg agatacaact      420
ggctcctcgg tgactctagg atgcctggtc aaggggttatt tccctgagcc agtgaccttg     480
acctggaact ctggatccct gtccagtggt gtgcacacct tcccagctgt cctgcagtct      540
gacctctaca ccctcagcag ctcagtgact gtaacctcga gcacctggcc cagccagtcc      600
atcacctgca atgtggccca cccggcaagc agcaccaagg tggacaagaa aattgagccc      660
cggggaccca caatcaagcc ctgtcctcca tgcaaatgcc cagcacctaa cctcttgggt      720
ggaccatccg tcttcatctt ccctccaaag atcaaggatg tactcatgat ctccctgagc      780
cccatagtca catgtgtggt ggtggatgtg agcgaggatg acccagatgt ccagatcagc      840
tggtttgtga acaacgtgga agtacacaca gctcagacac aaacccatag agaggattac      900
aacagtactc tccgggtggt cagtgccctc cccatccagc accaggactg gatgagtggc      960
aaggagttca atgcaaggt caacaacaaa gacctcccag cgcccatcga gagaaccatc      1020
tcaaaaccca agggtcagt aagagctcca caggtatatg tcttgcctcc accagaagaa      1080
gagatgacta agaaacaggt cactctgacc tgcatggtca cagacttcat gcctgaagac      1140
atttacgtgg agtggaccaa caacgggaaa acagagctaa actacaagaa cactgaacca      1200
gtcctggact ctgatggttc ttacttcatg tacagcaagc tgagagtgga aaagaagaac      1260
tgggtggaaa gaaatagcta ctcctgttca gtggtccacg agggtctgca caatcaccac      1320
acgactaaga gcttctcccg gactccgggt aaa                                   1353

<210> SEQ ID NO 146
<211> LENGTH: 642
<212> TYPE: DNA
<213> ORGANISM: Artificial
<220> FEATURE:
<223> OTHER INFORMATION: TF1413-03e005 L Chain Gene

<400> SEQUENCE: 146
gatgttgtga tgacccaaac tccatcctcc ttatctgcct ctctgggaga aagagtcagt       60
ctcacttgtc gggcaagtca ggaaattagt ggttacttaa gctggcttca gcagaaacca      120
gatggaacta ttaaacgcct gatctacgcc gcatccactt agattctggg tgtcccaaaa      180
aggttcagtg gcagtaggtc tgggtcagat tattctctca ccatcagcag ccttgagtct      240
gaagattttg cagactatta ctgtctacaa tatgctagtt atccgctcac gttcggtgct      300
gggaccaagc tggagctgaa acgggctgat gctgcaccaa ctgtatccat cttcccacca      360
tccagtgagc agttaacatc tggaggtgcc tcagtcgtgt gcttcttgaa caacttctac      420
cccaaagaca tcaatgtcaa gtggaagatt gatggcagtg aacgacaaaa tggcgtcctg      480
aacagttgga ctgatcagga cagcaaagac agcacctaca gcatgagcag cccctcacg      540
ttgaccaagg acgagtatga acgacataac agctatacct gtgaggccac tcacaagaca     600
tcaacttcac ccattgtcaa gagcttcaac aggaatgagt gt                         642

<210> SEQ ID NO 147
<211> LENGTH: 357
<212> TYPE: DNA
<213> ORGANISM: Artificial
<220> FEATURE:
<223> OTHER INFORMATION: TF1413-03e015 H Chain V Region Gene

<400> SEQUENCE: 147
gaggtccagc tgcagcagtc tggacctgag ctggtgaagc ctggagcttc aatgaagata       60
```

```
tcctgcaagg cttctggtta ctcattcact ggctacacca tgaactgggt gaagcagagc    120
catggaaaga accttgagtg gattggactt attaatcctt acaatggtgg tactagctac    180
aaccagaagt tcaagggcaa ggccacatta actgtagaca agtcatccag cacagcctac    240
atggagctcc tcagtctgac atctgaggac tctgcagtct attactgcgc aagaggggat    300 tactacccccc cctatgctat ggactactgg ggtcaaggaa cctcagtcac cgtctcg      357
```

<210> SEQ ID NO 148
<211> LENGTH: 324
<212> TYPE: DNA
<213> ORGANISM: Artificial
<220> FEATURE:
<223> OTHER INFORMATION: TF1413-03e015 L Chain V Region Gene

<400> SEQUENCE: 148

```
gacattgtga tgtcacagtc tccaaaattc atgtccacat cagtaggaga cagggtcagc     60
gtcacctgca aggccagtca gaatgtgggt actaatgtag cctggtatca acagaaaccg    120
gggcaatctc ctaaaccact gatttattcg gcgtcctacc ggtatagtgg agtccctgat    180
cgcttcacag gcagtggatc tgggacagat ttcactctca ccatcagcaa tgtgcagtct    240
gaagacttgg cagagtattt ctgtcagcaa tataacagat atcctctcac gttcggtgtt    300
gggaccaagc tggaaatcaa acgg                                           324
```

<210> SEQ ID NO 149
<211> LENGTH: 1350
<212> TYPE: DNA
<213> ORGANISM: Artificial
<220> FEATURE:
<223> OTHER INFORMATION: TF1413-03e015 H Chain Gene

<400> SEQUENCE: 149

```
gaggtccagc tgcagcagtc tggacctgag ctggtgaagc ctggagcttc aatgaagata     60
tcctgcaagg cttctggtta ctcattcact ggctacacca tgaactgggt gaagcagagc    120
catggaaaga accttgagtg gattggactt attaatcctt acaatggtgg tactagctac    180
aaccagaagt tcaagggcaa ggccacatta actgtagaca agtcatccag cacagcctac    240
atggagctcc tcagtctgac atctgaggac tctgcagtct attactgcgc aagaggggat    300 tactacccccc cctatgctat ggactactgg ggtcaaggaa cctcagtcac cgtctcgagc   360
gccaaaacaa cagcccccatc ggtctatcca ctggcccctg tgtgtggaga tacaactggc    420
tcctcggtga ctctaggatg cctggtcaag ggttatttcc ctgagccagt gaccttgacc    480
tggaactctg gatccctgtc cagtggtgtg cacaccttcc cagctgtcct gcagtctgac    540
ctctacaccc tcagcagctc agtgactgta acctcgagca cctggcccag ccagtccatc    600
acctgcaatg tggcccaccc ggcaagcagc accaaggtgg acaagaaaat tgagcccgg    660 ggacccacaa tcaagccctg tcctccatgc aaatgcccag cacctaacct cttgggtgga    720
ccatccgtct tcatcttccc tccaaagatc aaggatgtac tcatgatctc cctgagcccc    780
atagtcacat gtgtggtggt ggatgtgagc gaggatgacc cagatgtcca gatcagctgg    840
tttgtgaaca acgtggaagt acacacagct cagacacaaa cccatagaga ggattacaac    900
agtactctcc gggtggtcag tgccctcccc atccagcacc aggactggat gagtggcaag    960
gagttcaaat gcaaggtcaa caacaaagac ctcccagcgc ccatcgagag aaccatctca   1020
aaacccaaag ggtcagtaag agctccacag gtatatgtct tgcctccacc agaagaagag   1080
```

```
atgactaaga aacaggtcac tctgacctgc atggtcacag acttcatgcc tgaagacatt    1140
tacgtggagt ggaccaacaa cgggaaaaca gagctaaact acaagaacac tgaaccagtc    1200
ctggactctg atggttctta cttcatgtac agcaagctga gagtggaaaa aagaactgg     1260 gtggaaagaa atagctactc ctgttcagtg gtccacgagg gtctgcacaa tcaccacacg    1320
actaagagct ctcccggac tccgggtaaa                                      1350

<210> SEQ ID NO 150
<211> LENGTH: 642
<212> TYPE: DNA
<213> ORGANISM: Artificial
<220> FEATURE:
<223> OTHER INFORMATION: TF1413-03e015 L Chain Gene

<400> SEQUENCE: 150
gacattgtga tgtcacagtc tccaaaattc atgtccacat cagtaggaga cagggtcagc     60
gtcacctgca aggccagtca gaatgtgggt actaatgtag cctggtatca acagaaaccg    120
gggcaatctc ctaaaccact gatttattcg gcgtcctacc ggtatagtgg agtccctgat    180
cgcttcacag gcagtggatc tgggacagat ttcactctca ccatcagcaa tgtgcagtct    240
gaagacttgg cagagtattt ctgtcagcaa tataacagat atcctctcac gttcggtgtt    300
gggaccaagc tggaaatcaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

<210> SEQ ID NO 151
<211> LENGTH: 354
<212> TYPE: DNA
<213> ORGANISM: Artificial
<220> FEATURE:
<223> OTHER INFORMATION: TF1413-03e034 H Chain V Region Gene

<400> SEQUENCE: 151
gaggtccagc tgcagcagtc tggacctgag ctggagaagc ctggcgcttc agtgaagata     60
tcctgcaagg cttctggtta ctcattcact ggctacaaca tgaactgggt gaagcagagc    120
aatggaaaga gccttgagtg gattggaaat attgatcctt actatggtgg tactagctac    180
aaccagaagt tcaagggcaa ggccacattg actgtagaca atcctccag cacagcctac    240 atgcagctca gagcctgac atctgaggac tctgcagtct attactgtgc aagagggaac    300
tacgggtact atgctatgga ctactgggt caaggaacct cagtcaccgt ctcg           354

<210> SEQ ID NO 152
<211> LENGTH: 324
<212> TYPE: DNA
<213> ORGANISM: Artificial
<220> FEATURE:
<223> OTHER INFORMATION: TF1413-03e034 L Chain V Region Gene

<400> SEQUENCE: 152
gacattgtga tgtcacagtc tccaaaattc atgtccacat cagtaggaga cagggtcagc     60
atcacctgca aggccagtca gaatgttcgt actgctgtag cctggtatca acagaaacca    120
gggcagtctc ctaaagcact gatttacttg gcatccaacc ggcacactgg agtccctgat    180
```

| | |
|---|---|
| cgcttcacag gcagtggatc tgggacagat ttcactctca ccattagcaa tgtgcaatct | 240 |
| gaagacctgg cagattattt ctgtctgcaa cattggaatt atccgctcac gttcggtgct | 300 |
| gggaccaagc tggagctgaa acgg | 324 |

<210> SEQ ID NO 153
<211> LENGTH: 1347
<212> TYPE: DNA
<213> ORGANISM: Artificial
<220> FEATURE:
<223> OTHER INFORMATION: TF1413-03e034 H Chain Gene

<400> SEQUENCE: 153

| | |
|---|---|
| gaggtccagc tgcagcagtc tggacctgag ctggagaagc ctggcgcttc agtgaagata | 60 |
| tcctgcaagg cttctggtta ctcattcact ggctacaaca tgaactgggt gaagcagagc | 120 |
| aatggaaaga gccttgagtg gattggaaat attgatcctt actatggtgg tactagctac | 180 |
| aaccagaagt tcaagggcaa ggccacattg actgtagaca atcctccag cacagcctac | 240 |
| atgcagctca agagcctgac atctgaggac tctgcagtct attactgtgc aagagggaac | 300 |
| tacgggtact atgctatgga ctactgggt caaggaacct cagtcaccgt ctcgagcgcc | 360 |
| aaaacaacag ccccatcggt ctatccactg gcccctgtgt gtggagatac aactggctcc | 420 |
| tcggtgactc taggatgcct ggtcaagggt tatttccctg agccagtgac cttgacctgg | 480 |
| aactctggat ccctgtccag tggtgtgcac accttcccag ctgtcctgca gtctgacctc | 540 |
| tacaccctca gcagctcagt gactgtaacc tcgagcacct ggcccagcca gtccatcacc | 600 |
| tgcaatgtgg cccacccggc aagcagcacc aaggtggaca gaaaattga gccccgggga | 660 |
| cccacaatca gccctgtcc tccatgcaaa tgcccagcac ctaacctctt gggtggacca | 720 |
| tccgtcttca tcttccctcc aaagatcaag gatgtactca tgatctccct gagccccata | 780 |
| gtcacatgtg tggtggtgga tgtgagcgag gatgacccag atgtccagat cagctggttt | 840 |
| gtgaacaacg tggaagtaca cacagctcag acacaaaccc atagagagga ttacaacagt | 900 |
| actctccggg tggtcagtgc cctccccatc cagcaccagg actggatgag tggcaaggag | 960 |
| ttcaaatgca aggtcaacaa caaagacctc ccagcgccca tcgagagaac catctcaaaa | 1020 |
| cccaaagggt cagtaagagc tccacaggta tatgtcttgc ctccaccaga agaagagatg | 1080 |
| actaagaaac aggtcactct gacctgcatg gtcacagact tcatgcctga agacatttac | 1140 |
| gtggagtgga ccaacaacgg gaaaacagag ctaaactaca gaacactga accagtcctg | 1200 |
| gactctgatg gttcttactt catgtacagc aagctgagag tggaaaagaa gaactgggtg | 1260 |
| gaaagaaata gctactcctg ttcagtggtc cacgagggtc tgcacaatca ccacacgact | 1320 |
| aagagcttct cccggactcc gggtaaa | 1347 |

<210> SEQ ID NO 154
<211> LENGTH: 642
<212> TYPE: DNA
<213> ORGANISM: Artificial
<220> FEATURE:
<223> OTHER INFORMATION: TF1413-03e034 L Chain Gene

<400> SEQUENCE: 154

| | |
|---|---|
| gacattgtga tgtcacagtc tccaaaattc atgtccacat cagtaggaga cagggtcagc | 60 |
| atcacctgca aggccagtca gaatgttcgt actgctgtag cctggtatca acagaaacca | 120 |
| gggcagtctc ctaaagcact gatttacttg gcatccaacc ggcacactgg agtccctgat | 180 |

-continued

```
cgcttcacag gcagtggatc tgggacagat tcactctca ccattagcaa tgtgcaatct      240
gaagacctgg cagattattt ctgtctgcaa cattggaatt atccgctcac gttcggtgct      300
gggaccaagc tggagctgaa acgggctgat gctgcaccaa ctgtatccat cttcccacca      360
tccagtgagc agttaacatc tggaggtgcc tcagtcgtgt gcttcttgaa caacttctac      420
cccaaagaca tcaatgtcaa gtggaagatt gatggcagtg aacgacaaaa tggcgtcctg      480
aacagttgga ctgatcagga cagcaaagac agcacctaca gcatgagcag cacccctcacg    540 ttgaccaagg acgagtatga acgacataac agctatacct gtgaggccac tcacaagaca     600
tcaacttcac ccattgtcaa gagcttcaac aggaatgagt gt                        642
```

<210> SEQ ID NO 155
<211> LENGTH: 440
<212> TYPE: PRT
<213> ORGANISM: Homo sapiens
<220> FEATURE:
<221> NAME/KEY: MISC_FEATURE
<223> OTHER INFORMATION: Human GPC3 N Terminal Fragment

<400> SEQUENCE: 155

```
Asp Ala Thr Cys His Gln Val Arg Ser Phe Phe Gln Arg Leu Gln Pro
1               5                   10                  15

Gly Leu Lys Trp Val Pro Glu Thr Pro Val Pro Gly Ser Asp Leu Gln
            20                  25                  30

Val Cys Leu Pro Lys Gly Pro Thr Cys Cys Ser Arg Lys Met Glu Glu
        35                  40                  45

Lys Tyr Gln Leu Thr Ala Arg Leu Asn Met Glu Gln Leu Leu Gln Ser
    50                  55                  60

Ala Ser Met Glu Leu Lys Phe Leu Ile Ile Gln Asn Ala Ala Val Phe
65                  70                  75                  80

Gln Glu Ala Phe Glu Ile Val Val Arg His Ala Lys Asn Tyr Thr Asn
                85                  90                  95

Ala Met Phe Lys Asn Asn Tyr Pro Ser Leu Thr Pro Gln Ala Phe Glu
            100                 105                 110

Phe Val Gly Glu Phe Phe Thr Asp Val Ser Leu Tyr Ile Leu Gly Ser
        115                 120                 125

Asp Ile Asn Val Asp Asp Met Val Asn Glu Leu Phe Asp Ser Leu Phe
    130                 135                 140

Pro Val Ile Tyr Thr Gln Leu Met Asn Pro Gly Leu Pro Asp Ser Ala
145                 150                 155                 160

Leu Asp Ile Asn Glu Cys Leu Arg Gly Ala Arg Arg Asp Leu Lys Val
                165                 170                 175

Phe Gly Asn Phe Pro Lys Leu Ile Met Thr Gln Val Ser Lys Ser Leu
            180                 185                 190

Gln Val Thr Arg Ile Phe Leu Gln Ala Leu Asn Leu Gly Ile Glu Val
        195                 200                 205

Ile Asn Thr Thr Asp His Leu Lys Phe Ser Lys Asp Cys Gly Arg Met
    210                 215                 220

Leu Thr Arg Met Trp Tyr Cys Ser Tyr Cys Gln Gly Leu Met Met Val
225                 230                 235                 240

Lys Pro Cys Gly Gly Tyr Cys Asn Val Val Met Gln Gly Cys Met Ala
                245                 250                 255

Gly Val Val Glu Ile Asp Lys Tyr Trp Arg Glu Tyr Ile Leu Ser Leu
            260                 265                 270

Glu Glu Leu Val Asn Gly Met Tyr Arg Ile Tyr Asp Met Glu Asn Val
```

```
                    275                 280                 285
Leu Leu Gly Leu Phe Ser Thr Ile His Asp Ser Ile Gln Tyr Val Gln
            290                 295                 300
Lys Asn Ala Gly Lys Leu Thr Thr Thr Ile Gly Lys Leu Cys Ala His
305                 310                 315                 320
Ser Gln Gln Arg Gln Tyr Arg Ser Ala Tyr Tyr Pro Glu Asp Leu Phe
                325                 330                 335
Ile Asp Lys Lys Val Leu Lys Val Ala His Val Glu His Glu Glu Thr
            340                 345                 350
Leu Ser Ser Arg Arg Arg Glu Leu Ile Gln Lys Leu Lys Ser Phe Ile
                355                 360                 365
Ser Phe Tyr Ser Ala Leu Pro Gly Tyr Ile Cys Ser His Ser Pro Val
            370                 375                 380
Ala Glu Asn Asp Thr Leu Cys Trp Asn Gly Gln Glu Leu Val Glu Arg
385                 390                 395                 400
Tyr Ser Gln Lys Ala Ala Arg Asn Gly Met Lys Asn Gln Phe Asn Leu
                405                 410                 415
His Glu Leu Lys Met Lys Gly Pro Glu Pro Val Val Ser Gln Ile Ile
            420                 425                 430
Asp Lys Leu Lys His Ile Asn Gln
            435                 440

<210> SEQ ID NO 156
<211> LENGTH: 109
<212> TYPE: PRT
<213> ORGANISM: Homo sapiens
<220> FEATURE:
<221> NAME/KEY: MISC_FEATURE
<223> OTHER INFORMATION: Human GPC3 C Terminal Fragment

<400> SEQUENCE: 156

Leu Leu Arg Thr Met Ser Met Pro Lys Gly Arg Val Leu Asp Lys Asn
1               5                   10                  15
Leu Asp Glu Glu Gly Phe Glu Ser Gly Asp Cys Gly Asp Asp Glu Asp
                20                  25                  30
Glu Cys Ile Gly Gly Ser Gly Asp Gly Met Ile Lys Val Lys Asn Gln
            35                  40                  45
Leu Arg Phe Leu Ala Glu Leu Ala Tyr Asp Leu Asp Val Asp Asp Ala
        50                  55                  60
Pro Gly Asn Ser Gln Gln Ala Thr Pro Lys Asp Asn Glu Ile Ser Thr
65                  70                  75                  80
Phe His Asn Leu Gly Asn Val His Ser Pro Leu Lys Leu Leu Thr Ser
                85                  90                  95
Met Ala Ile Ser Val Val Cys Phe Phe Phe Leu Val His
            100                 105

<210> SEQ ID NO 157
<211> LENGTH: 580
<212> TYPE: PRT
<213> ORGANISM: Homo sapiens
<220> FEATURE:
<221> NAME/KEY: MISC_FEATURE
<223> OTHER INFORMATION: Human GPC3

<400> SEQUENCE: 157

Met Ala Gly Thr Val Arg Thr Ala Cys Leu Val Val Ala Met Leu Leu
1               5                   10                  15
Ser Leu Asp Phe Pro Gly Gln Ala Gln Pro Pro Pro Pro Pro Pro Asp
```

```
                 20                  25                  30
Ala Thr Cys His Gln Val Arg Ser Phe Phe Gln Arg Leu Gln Pro Gly
             35                  40                  45
Leu Lys Trp Val Pro Glu Thr Pro Val Pro Gly Ser Asp Leu Gln Val
 50                  55                  60
Cys Leu Pro Lys Gly Pro Thr Cys Cys Ser Arg Lys Met Glu Glu Lys
 65                  70                  75                  80
Tyr Gln Leu Thr Ala Arg Leu Asn Met Glu Gln Leu Leu Gln Ser Ala
                 85                  90                  95
Ser Met Glu Leu Lys Phe Leu Ile Ile Gln Asn Ala Ala Val Phe Gln
            100                 105                 110
Glu Ala Phe Glu Ile Val Val Arg His Ala Lys Asn Tyr Thr Asn Ala
            115                 120                 125
Met Phe Lys Asn Asn Tyr Pro Ser Leu Thr Pro Gln Ala Phe Glu Phe
            130                 135                 140
Val Gly Glu Phe Phe Thr Asp Val Ser Leu Tyr Ile Leu Gly Ser Asp
145                 150                 155                 160
Ile Asn Val Asp Asp Met Val Asn Glu Leu Phe Asp Ser Leu Phe Pro
                165                 170                 175
Val Ile Tyr Thr Gln Leu Met Asn Pro Gly Leu Pro Asp Ser Ala Leu
            180                 185                 190
Asp Ile Asn Glu Cys Leu Arg Gly Ala Arg Arg Asp Leu Lys Val Phe
            195                 200                 205
Gly Asn Phe Pro Lys Leu Ile Met Thr Gln Val Ser Lys Ser Leu Gln
            210                 215                 220
Val Thr Arg Ile Phe Leu Gln Ala Leu Asn Leu Gly Ile Glu Val Ile
225                 230                 235                 240
Asn Thr Thr Asp His Leu Lys Phe Ser Lys Asp Cys Gly Arg Met Leu
                245                 250                 255
Thr Arg Met Trp Tyr Cys Ser Tyr Cys Gln Gly Leu Met Met Val Lys
            260                 265                 270
Pro Cys Gly Gly Tyr Cys Asn Val Val Met Gln Gly Cys Met Ala Gly
            275                 280                 285
Val Val Glu Ile Asp Lys Tyr Trp Arg Glu Tyr Ile Leu Ser Leu Glu
            290                 295                 300
Glu Leu Val Asn Gly Met Tyr Arg Ile Tyr Asp Met Glu Asn Val Leu
305                 310                 315                 320
Leu Gly Leu Phe Ser Thr Ile His Asp Ser Ile Gln Tyr Val Gln Lys
                325                 330                 335
Asn Ala Gly Lys Leu Thr Thr Thr Ile Gly Lys Leu Cys Ala His Ser
            340                 345                 350
Gln Gln Arg Gln Tyr Arg Ser Ala Tyr Tyr Pro Glu Asp Leu Phe Ile
            355                 360                 365
Asp Lys Lys Val Leu Lys Val Ala His Val Glu His Glu Glu Thr Leu
            370                 375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                405                 410                 415
Glu Asn Asp Thr Leu Cys Trp Asn Gly Gln Glu Leu Val Glu Arg Tyr
            420                 425                 430
Ser Gln Lys Ala Ala Arg Asn Gly Met Lys Asn Gln Phe Asn Leu His
            435                 440                 445
```

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
        580

<210> SEQ ID NO 158
<211> LENGTH: 1320
<212> TYPE: DNA
<213> ORGANISM: Homo sapiens
<220> FEATURE:
<221> NAME/KEY: misc_feature
<223> OTHER INFORMATION: Human GPC3 N Terminal Fragment Gene

<400> SEQUENCE: 158
gacgccacct gtcaccaagt ccgctccttc ttccagagac tgcagcccgg actcaagtgg      60
gtgccagaaa ctcccgtgcc aggatcagat ttgcaagtat gtctccctaa gggcccaaca     120
tgctgctcaa gaaagatgga agaaaaatac caactaacag cacgattgaa catggaacag     180
ctgcttcagt ctgcaagtat ggagctcaag ttcttaatta ttcagaatgc tgcggttttc     240
caagaggcct ttgaaattgt tgttcgccat gccaagaact acaccaatgc catgttcaag     300
aacaactacc caagcctgac tccacaagct tttgagtttg tgggtgaatt tttcacagat     360
gtgtctctct acatcttggg ttctgacatc aatgtagatg acatggtcaa tgaattgttt     420
gacagcctgt ttccagtcat ctatacccag ctaatgaacc aggcctgcc tgattcagcc      480 ttggacatca atgagtgcct ccgaggagca agacgtgacc tgaaagtatt gggaatttc      540 cccaagctta ttatgaccca ggtttccaag tcactgcaag tcactaggat cttccttcag     600
gctctgaatc ttggaattga agtgatcaac acaactgatc acctgaagtt cagtaaggac     660
tgtggccgaa tgctcaccag aatgtggtac tgctcttact gccagggact gatgatggtt     720
aaaccctgtg gcggttactg caatgtggtc atgcaaggct gtatggcagg tgtggtggag     780
attgacaagt actggagaga atacattctg tcccttgaag aacttgtgaa tggcatgtac     840
agaatctatg acatggagaa cgtactgctt ggtctctttt caacaatcca tgattctatc     900
cagtatgtcc agaagaatgc aggaaagctg accaccacta ttggcaagtt atgtgcccat     960
tctcaacaac gccaatatag atctgcttat tatcctgaag atctctttat tgacaagaaa    1020
gtattaaaag ttgctcatgt agaacatgaa gaaaccttat ccagccgaag aagggaacta    1080
attcagaagt tgaagtcttt catcagcttc tatagtgctt tgcctggcta catctgcagc    1140
catagccctg tggcggaaaa cgacacccctt tgctggaatg gacaagaact cgtggagaga    1200

```
tacagccaaa aggcagcaag gaatggaatg aaaaaccagt tcaatctcca tgagctgaaa      1260
atgaagggcc ctgagccagt ggtcagtcaa attattgaca aactgaagca cattaaccag      1320

<210> SEQ ID NO 159
<211> LENGTH: 327
<212> TYPE: DNA
<213> ORGANISM: Homo sapiens
<220> FEATURE:
<221> NAME/KEY: misc_feature
<223> OTHER INFORMATION: Human GPC3 C Terminal Fragment Gene

<400> SEQUENCE: 159
ctcctgagaa ccatgtctat gcccaaaggt agagttctgg ataaaaacct ggatgaggaa        60
gggtttgaaa gtggagactg cggtgatgat gaagatgagt gcattggagg ctctggtgat       120
ggaatgataa agtgaagaa tcagctccgc ttccttgcag aactggccta tgatctggat        180
gtggatgatg cgcctggaaa cagtcagcag gcaactccga aggacaacga gataagcacc       240
tttcacaacc tcgggaacgt tcattccccg ctgaagcttc tcaccagcat ggccatctcg       300
gtggtgtgct tcttcttcct ggtgcac                                          327

<210> SEQ ID NO 160
<211> LENGTH: 1743
<212> TYPE: DNA
<213> ORGANISM: Homo sapiens

<400> SEQUENCE: 160
atggccggga ccgtgcgcac cgcgtgcttg gtggtggcga tgctgctcag cttggacttc        60
ccgggacagg cgcagccccc gccgccgccg ccggacgcca cctgtcacca agtccgctcc       120
ttcttccaga gactgcagcc cggactcaag tgggtgccag aaactcccgt gccaggatca       180
gatttgcaag tatgtctccc taagggccca acatgctgct caagaaagat ggaagaaaaa       240
taccaactaa cagcacgatt gaacatgaaa cagctgcttc agtctgcaag tatggagctc       300
aagttcttaa ttattcagaa tgctgcggtt ttccaagagg cctttgaaat tgttgttcgc       360
catgccaaga actacaccaa tgccatgttc aagaacaact acccaagcct gactccacaa       420
gcttttgagt ttgtgggtga atttttcaca gatgtgtctc tctacatctt gggttctgac       480
atcaatgtag atgacatggt caatgaattg tttgacagcc tgtttccagt catctatacc       540
cagctaatga acccaggcct gcctgattca gccttggaca tcaatgagtg cctccgagga       600
gcaagacgtg acctgaaagt atttgggaat tcccccaagc ttattatgac ccaggttttcc       660 aagtcactgc aagtcactag gatcttcctt caggctctga tcttggaat tgaagtgatc        720 aacacaactg atcacctgaa gttcagtaag gactgtggcc gaatgctcac cagaatgtgg       780
tactgctctt actgccaggg actgatgatg gttaaaccct gtggcggtta ctgcaatgtg       840
gtcatgcaag gctgtatggc aggtgtggtg gagattgaca agtactggag agaatacatt       900
ctgtcccttg aagaacttgt gaatggcatg tacagaatct atgacatgga gaacgtactg       960
cttggtctct tttcaacaat ccatgattct atccagtatg tccagaagaa tgcaggaaag      1020
ctgaccacca ctattggcaa gttatgtgcc cattctcaac aacgccaata tagatctgct      1080
tattatcctg aagatctctt tattgacaag aaagtattaa aagttgctca tgtagaacat      1140
gaagaaacct tatccagccg aagaagggaa ctaattcaga agttgaagtc tttcatcagc      1200
ttctatagtg ctttgcctgg ctacatctgc agccatagcc ctgtggcgga aaacgacacc      1260
ctttgctgga atggacaaga actcgtggag agatacagcc aaaaggcagc aaggaatgga      1320
```

| | | |
|---|---|---|
| atgaaaaacc agttcaatct ccatgagctg aaaatgaagg gccctgagcc agtggtcagt | | 1380 |
| caaattattg acaaactgaa gcacattaac cagctcctga gaaccatgtc tatgcccaaa | | 1440 |
| ggtagagttc tggataaaaa cctggatgag gaagggtttg aaagtggaga ctgcggtgat | | 1500 |
| gatgaagatg agtgcattgg aggctctggt gatggaatga taaaagtgaa gaatcagctc | | 1560 |
| cgcttccttg cagaactggc ctatgatctg gatgtggatg atgcgcctgg aaacagtcag | | 1620 |
| caggcaactc cgaaggacaa cgagataagc acctttcaca acctcgggaa cgttcattcc | | 1680 |
| ccgctgaagc ttctcaccag catggccatc tcggtggtgt gcttcttctt cctggtgcac | | 1740 |
| tga | | 1743 |

<210> SEQ ID NO 161
<211> LENGTH: 33
<212> TYPE: DNA
<213> ORGANISM: Artificial
<220> FEATURE:
<223> OTHER INFORMATION: F-1 Primer

<400> SEQUENCE: 161
tcccccgggg gacgccacct gtcaccaagt ccg        33

<210> SEQ ID NO 162
<211> LENGTH: 33
<212> TYPE: DNA
<213> ORGANISM: Artificial
<220> FEATURE:
<223> OTHER INFORMATION: R-7 Primer

<400> SEQUENCE: 162
tccccgcggc tggttaatgt gcttcagttt gtc        33

<210> SEQ ID NO 163
<211> LENGTH: 28
<212> TYPE: DNA
<213> ORGANISM: Artificial
<220> FEATURE:
<223> OTHER INFORMATION: F-8 Primer

<400> SEQUENCE: 163
tcccccgggg ctcctgagaa ccatgtct        28

<210> SEQ ID NO 164
<211> LENGTH: 33
<212> TYPE: DNA
<213> ORGANISM: Artificial
<220> FEATURE:
<223> OTHER INFORMATION: R-9 Primer

<400> SEQUENCE: 164
tccccgcggg tgcaccagga agaagaagca cac        33

<210> SEQ ID NO 165
<211> LENGTH: 241
<212> TYPE: PRT
<213> ORGANISM: Artificial
<220> FEATURE:
<223> OTHER INFORMATION: TF1413-02d028 scFv

<400> SEQUENCE: 165

Gln Val Gln Leu Lys Glu Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

-continued

Asn Met Asn Trp Val Lys Gln Ser Asn Gly Lys Ser Leu Glu Trp Ile
            35                  40                  45

Gly Asn Ile Asp Pro Tyr Tyr Gly Gly Thr Ser Tyr Asn Gln Lys Phe
        50                  55                  60

Lys Gly Lys Ala Thr Leu Thr Val Asp Lys Ser Ser Thr Ala Tyr
 65                  70                  75                  80

Met Gln Leu Lys Ser Leu Thr Ser Glu Asp Ser Ala Val Tyr Tyr Cys
                85                  90                  95

Ala Arg Gly Asp Tyr Arg Ala Tyr Tyr Phe Asp Tyr Trp Gly Gln Gly
                100                 105                 110

Thr Thr Leu Thr Val Ser Gly Gly Gly Ser Gly Gly Gly Ser
            115                 120                 125

Gly Gly Gly Ser Asp Ile Gln Met Thr Gln Ser Pro Lys Phe Met
        130                 135                 140

Ser Thr Ser Val Gly Asp Arg Val Ser Ile Thr Cys Lys Ala Ser Gln
145                 150                 155                 160

Asn Val Arg Thr Ala Val Ala Trp Tyr Gln Gln Lys Pro Gly Gln Ser
                165                 170                 175

Pro Lys Ala Leu Ile Tyr Leu Ala Ser Asn Arg His Thr Gly Val Pro
                180                 185                 190

Asp Arg Phe Thr Gly Ser Gly Ser Gly Thr Asp Phe Thr Leu Thr Ile
                195                 200                 205

Ser Asn Val Gln Ser Glu Asp Leu Ala Asp Tyr Phe Cys Leu Gln His
                210                 215                 220

Trp Asn Tyr Pro Leu Thr Phe Gly Ala Gly Thr Lys Leu Glu Leu Lys
225                 230                 235                 240

Arg

<210> SEQ ID NO 166
<211> LENGTH: 245
<212> TYPE: PRT
<213> ORGANISM: Artificial
<220> FEATURE:
<223> OTHER INFORMATION: TF1413-02d039 scFv

<400> SEQUENCE: 166

Glu Val Lys Leu Val Glu Ser Gly Gly Gly Leu Val Lys Pro Gly Gly
 1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
            35                  40                  45

Ala Tyr Ile Ser Ser Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg Arg Gly Leu Arg Arg Ala Met Asp Tyr Trp Gly Gln Gly Thr
                100                 105                 110

Ser Val Thr Val Ser Gly Gly Gly Gly Ser Gly Gly Gly Gly Ser Gly
            115                 120                 125

Gly Gly Gly Ser Asp Val Val Met Thr Gln Thr Pro Leu Ser Leu Pro
        130                 135                 140

```
Val Ser Leu Gly Asp Gln Ala Ser Ile Ser Cys Arg Ser Ser Gln Ser
145                 150                 155                 160

Leu Val His Ser Asn Gly Asn Thr Tyr Leu His Trp Tyr Leu Gln Lys
            165                 170                 175

Pro Gly Gln Ser Pro Lys Leu Leu Ile Tyr Lys Val Ser Asn Arg Phe
            180                 185                 190

Ser Gly Val Pro Asp Arg Phe Ser Gly Ser Gly Ser Gly Thr Asp Phe
            195                 200                 205

Thr Leu Lys Ile Ser Arg Val Glu Ala Glu Asp Leu Gly Val Tyr Phe
            210                 215                 220

Cys Ser Gln Ser Thr His Val Pro Leu Thr Phe Gly Ala Gly Thr Lys
225                 230                 235                 240

Leu Glu Leu Lys Arg
            245

<210> SEQ ID NO 167
<211> LENGTH: 237
<212> TYPE: PRT
<213> ORGANISM: Artificial
<220> FEATURE:
<223> OTHER INFORMATION: TF1413-02e004 scFv

<400> SEQUENCE: 167

Gln Val Gln Leu Gln Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Glu Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Tyr Tyr Ala Met Asp Tyr Trp Gly Gln Gly Thr Ser Val
            100                 105                 110

Thr Val Ser Gly Gly Gly Gly Ser Gly Gly Gly Gly Ser Gly Gly Gly
        115                 120                 125

Gly Ser Asp Ile Val Leu Thr Gln Ser Pro Lys Phe Met Ser Thr Ser
    130                 135                 140

Val Gly Asp Arg Val Ser Ile Thr Cys Lys Ala Ser Gln Asp Val Ser
145                 150                 155                 160

Thr Ala Val Ala Trp Tyr Gln Gln Lys Pro Gly Gln Ser Pro Lys Leu
            165                 170                 175

Leu Ile Tyr Ser Ala Ser Tyr Arg Tyr Thr Gly Val Pro Asp Arg Phe
            180                 185                 190

Thr Gly Ser Gly Ser Gly Thr Asp Phe Thr Phe Thr Ile Ser Ser Val
            195                 200                 205

Gln Ala Glu Asp Leu Ala Val Tyr Tyr Cys Gln Gln His Tyr Ser Thr
            210                 215                 220

Pro Thr Phe Gly Gly Gly Thr Lys Leu Glu Ile Lys Arg
225                 230                 235

<210> SEQ ID NO 168
<211> LENGTH: 243
```

```
<212> TYPE: PRT
<213> ORGANISM: Artificial
<220> FEATURE:
<223> OTHER INFORMATION: TF1413-02e014 scFv

<400> SEQUENCE: 168

Gln Val Gln Leu Lys Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gly Tyr Tyr Asp Tyr Asp Gly Tyr Ala Met Asp Tyr Trp Gly
                100                 105                 110

Gln Gly Thr Ser Val Thr Val Ser Gly Gly Gly Ser Gly Gly Gly
            115                 120                 125

Gly Ser Gly Gly Gly Gly Ser Asp Ile Val Leu Thr Gln Ser Pro Lys
        130                 135                 140

Phe Met Ser Thr Ser Val Gly Asp Arg Val Ser Ile Thr Cys Lys Ala
145                 150                 155                 160

Ser Gln Asp Val Gly Thr Ala Val Ala Trp Tyr Gln Gln Lys Pro Gly
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
        195                 200                 205

Thr Ile Ser Asn Val Gln Ser Glu Asp Leu Ala Asp Tyr Phe Cys Gln
210                 215                 220

Gln Tyr Ser Ser Tyr Pro Leu Thr Phe Gly Gly Gly Thr Lys Leu Glu
225                 230                 235                 240

Ile Lys Arg

<210> SEQ ID NO 169
<211> LENGTH: 246
<212> TYPE: PRT
<213> ORGANISM: Artificial
<220> FEATURE:
<223> OTHER INFORMATION: TF1413-02e030 scFv

<400> SEQUENCE: 169

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asn Thr Ile Tyr Asp Pro Lys Phe
        50                  55                  60

Gln Gly Lys Ala Ser Ile Thr Ala Asp Thr Ser Ser Asn Thr Ala Tyr
65                  70                  75                  80
```

```
Leu Gln Leu Ser Ser Leu Thr Ser Glu Asp Thr Ala Val Tyr Tyr Cys
                 85                  90                  95

Ala Ile Ser Thr Met Ile Thr Thr Leu Asp Tyr Trp Gly Gln Gly Thr
            100                 105                 110

Thr Leu Thr Val Ser Gly Gly Gly Gly Ser Gly Gly Gly Gly Ser Gly
            115                 120                 125

Gly Gly Gly Ser Asp Ile Gln Met Thr Gln Ser Pro Ser Ser Leu Ala
130                 135                 140

Met Ser Val Gly Gln Lys Val Thr Met Ser Cys Lys Ser Ser Gln Ser
145                 150                 155                 160

Leu Leu Asn Ser Ser Asn Gln Lys Asn Tyr Leu Ala Trp Tyr Gln Gln
                165                 170                 175

Lys Pro Gly Gln Ser Pro Lys Leu Leu Val Tyr Phe Ala Ser Thr Arg
            180                 185                 190

Glu Ser Gly Val Pro Asp Arg Phe Ile Gly Ser Gly Ser Gly Thr Asp
            195                 200                 205

Phe Thr Leu Thr Ile Ser Ser Val Gln Ala Glu Asp Leu Ala Asp Tyr
            210                 215                 220

Phe Cys Gln Gln His Tyr Ser Thr Pro Leu Thr Phe Gly Ala Gly Thr
225                 230                 235                 240

Lys Leu Glu Leu Lys Arg
            245

<210> SEQ ID NO 170
<211> LENGTH: 239
<212> TYPE: PRT
<213> ORGANISM: Artificial
<220> FEATURE:
<223> OTHER INFORMATION: TF1413-02e040 scFv

<400> SEQUENCE: 170

Glu Val Met Leu Val Glu Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ser Tyr Asn Gln Asn Phe
50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Tyr Tyr Gly Arg Phe Asp Tyr Trp Gly Gln Gly Thr Thr
            100                 105                 110

Leu Thr Val Ser Gly Gly Gly Gly Ser Gly Gly Gly Gly Ser Gly Gly
            115                 120                 125

Gly Gly Ser Asp Ile Leu Leu Thr Gln Ser Pro Lys Phe Met Ser Thr
130                 135                 140

Ser Val Gly Asp Arg Val Ser Ile Thr Cys Lys Ala Ser Gln Asn Val
145                 150                 155                 160

Arg Thr Ala Val Ala Trp Tyr Gln Gln Lys Pro Gly Gln Ser Pro Lys
                165                 170                 175

Ala Leu Ile Tyr Leu Ala Ser Asn Arg His Thr Gly Val Pro Asp Arg
            180                 185                 190
```

```
Phe Thr Gly Ser Gly Ser Gly Thr Asp Phe Thr Leu Thr Ile Ser Asn
            195                 200                 205

Val Gln Ser Glu Asp Leu Ala Asp Tyr Phe Cys Leu Gln His Trp Asn
    210                 215                 220

Tyr Pro Leu Thr Phe Gly Ala Gly Thr Lys Leu Glu Leu Lys Arg
225                 230                 235

<210> SEQ ID NO 171
<211> LENGTH: 238
<212> TYPE: PRT
<213> ORGANISM: Artificial
<220> FEATURE:
<223> OTHER INFORMATION: TF1413-03e001 scFv

<400> SEQUENCE: 171

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Val Lys Ser Leu Glu Trp Ile
        35                  40                  45

Gly Arg Ile Asn Pro Tyr Asn Gly Ala Thr Ser Tyr Asn Gln Asn Phe
    50                  55                  60

Lys Asp Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Asn Tyr Gly Tyr Phe Asp Tyr Trp Gly Gln Gly Thr Thr Leu
            100                 105                 110

Thr Val Ser Gly Gly Gly Gly Ser Gly Gly Gly Ser Gly Gly Gly
        115                 120                 125

Gly Ser Asp Ile Lys Met Thr Gln Ser Pro Lys Phe Met Ser Thr Ser
    130                 135                 140

Val Gly Asp Arg Val Ser Val Thr Cys Glu Ala Ser Gln Asn Val Asp
145                 150                 155                 160

Asn Asn Val Val Trp Tyr Gln Gln Lys Pro Gly Gln Ser Pro Lys Ala
                165                 170                 175

Leu Ile Tyr Ser Ala Ser Tyr Arg Tyr Ser Gly Val Pro Asp Arg Phe
            180                 185                 190

Thr Gly Ser Gly Ser Gly Thr Asp Phe Thr Leu Thr Ile Ser Asn Val
        195                 200                 205

Gln Ser Glu Asp Leu Ala Glu Tyr Phe Cys Gln Gln Tyr Asn Ser Tyr
    210                 215                 220

Pro Leu Thr Phe Gly Ala Gly Thr Lys Leu Glu Ile Lys Arg
225                 230                 235

<210> SEQ ID NO 172
<211> LENGTH: 238
<212> TYPE: PRT
<213> ORGANISM: Artificial
<220> FEATURE:
<223> OTHER INFORMATION: TF1413-03e004 scFv

<400> SEQUENCE: 172

Gln Val Gln Leu Lys Gln Ser Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30
```

-continued

Trp Met Asn Trp Val Lys Gln Arg Pro Gly Arg Gly Leu Glu Trp Ile
            35                  40                  45

Gly Arg Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Tyr Tyr Gly Ser Asn Tyr Trp Gly Gln Gly Thr Thr Leu
            100                 105                 110

Thr Val Ser Gly Gly Gly Gly Ser Gly Gly Gly Gly Ser Gly Gly Gly
            115                 120                 125

Gly Ser Asp Ile Lys Met Thr Gln Ser Pro Lys Phe Met Ser Thr Ser
    130                 135                 140

Val Gly Asp Arg Val Ser Val Thr Cys Lys Ala Ser Gln Asn Val Gly
145                 150                 155                 160

Thr Asn Val Ala Trp Tyr Gln Gln Lys Pro Gly Gln Ser Pro Lys Ala
                165                 170                 175

Leu Ile Tyr Ser Ala Ser Tyr Arg Tyr Ser Gly Val Pro Asp Arg Phe
            180                 185                 190

Thr Gly Ser Gly Ser Gly Thr Asp Phe Thr Leu Thr Ile Ser Asn Val
            195                 200                 205

Gln Ser Glu Asp Leu Ala Glu Tyr Phe Cys Gln Gln Tyr Asn Ser Tyr
    210                 215                 220

Pro Leu Thr Phe Gly Ala Gly Thr Lys Leu Glu Leu Lys Arg
225                 230                 235

<210> SEQ ID NO 173
<211> LENGTH: 243
<212> TYPE: PRT
<213> ORGANISM: Artificial
<220> FEATURE:
<223> OTHER INFORMATION: TF1413-03e005 scFv

<400> SEQUENCE: 173

Gln Val Gln Leu Lys Glu Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Phe Tyr Tyr Asp Tyr Asp Gly Tyr Ala Met Asp Tyr Trp Gly
            100                 105                 110

Gln Gly Thr Ser Val Thr Val Ser Gly Gly Gly Gly Ser Gly Gly Gly
            115                 120                 125

Gly Ser Gly Gly Gly Gly Ser Asp Val Val Met Thr Gln Thr Pro Ser
    130                 135                 140

Ser Leu Ser Ala Ser Leu Gly Glu Arg Val Ser Leu Thr Cys Arg Ala
145                 150                 155                 160

Ser Gln Glu Ile Ser Gly Tyr Leu Ser Trp Leu Gln Lys Pro Asp
                165                 170                 175

Gly Thr Ile Lys Arg Leu Ile Tyr Ala Ala Ser Thr Leu Asp Ser Gly
            180                 185                 190

Val Pro Lys Arg Phe Ser Gly Ser Arg Ser Gly Ser Asp Tyr Ser Leu
            195                 200                 205

Thr Ile Ser Ser Leu Glu Ser Glu Asp Phe Ala Asp Tyr Tyr Cys Leu
    210                 215                 220

Gln Tyr Ala Ser Tyr Pro Leu Thr Phe Gly Ala Gly Thr Lys Leu Glu
225                 230                 235                 240

Leu Lys Arg

<210> SEQ ID NO 174
<211> LENGTH: 242
<212> TYPE: PRT
<213> ORGANISM: Artificial
<220> FEATURE:
<223> OTHER INFORMATION: TF1413-03e015 scFv

<400> SEQUENCE: 174

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Asp Tyr Tyr Pro Pro Tyr Ala Met Asp Tyr Trp Gly Gln
            100                 105                 110

Gly Thr Ser Val Thr Val Ser Gly Gly Gly Gly Ser Gly Gly Gly Gly
        115                 120                 125

Ser Gly Gly Gly Gly Ser Asp Ile Val Met Ser Gln Ser Pro Lys Phe
    130                 135                 140

Met Ser Thr Ser Val Gly Asp Arg Val Ser Val Thr Cys Lys Ala Ser
145                 150                 155                 160

Gln Asn Val Gly Thr Asn Val Ala Trp Tyr Gln Gln Lys Pro Gly Gln
                165                 170                 175

Ser Pro Lys Pro Leu Ile Tyr Ser Ala Ser Tyr Arg Tyr Ser Gly Val
            180                 185                 190

Pro Asp Arg Phe Thr Gly Ser Gly Ser Gly Thr Asp Phe Thr Leu Thr
        195                 200                 205

Ile Ser Asn Val Gln Ser Glu Asp Leu Ala Glu Tyr Phe Cys Gln Gln
    210                 215                 220

Tyr Asn Arg Tyr Pro Leu Thr Phe Gly Val Gly Thr Lys Leu Glu Ile
225                 230                 235                 240

Lys Arg

<210> SEQ ID NO 175
<211> LENGTH: 241
<212> TYPE: PRT

```
<213> ORGANISM: Artificial
<220> FEATURE:
<223> OTHER INFORMATION: TF1413-03e034 scFv

<400> SEQUENCE: 175
```

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asn Tyr Gly Tyr Tyr Ala Met Asp Tyr Trp Gly Gln Gly
            100                 105                 110

Thr Ser Val Thr Val Ser Gly Gly Gly Gly Ser Gly Gly Gly Gly Ser
            115                 120                 125

Gly Gly Gly Gly Ser Asp Ile Val Met Ser Gln Ser Pro Lys Phe Met
        130                 135                 140

Ser Thr Ser Val Gly Asp Arg Val Ser Ile Thr Cys Lys Ala Ser Gln
145                 150                 155                 160

Asn Val Arg Thr Ala Val Ala Trp Tyr Gln Gln Lys Pro Gly Gln Ser
                165                 170                 175

Pro Lys Ala Leu Ile Tyr Leu Ala Ser Asn Arg His Thr Gly Val Pro
            180                 185                 190

Asp Arg Phe Thr Gly Ser Gly Ser Gly Thr Asp Phe Thr Leu Thr Ile
        195                 200                 205

Ser Asn Val Gln Ser Glu Asp Leu Ala Asp Tyr Phe Cys Leu Gln His
    210                 215                 220

Trp Asn Tyr Pro Leu Thr Phe Gly Ala Gly Thr Lys Leu Glu Leu Lys
225                 230                 235                 240

Arg

```
<210> SEQ ID NO 176
<211> LENGTH: 20
<212> TYPE: DNA
<213> ORGANISM: Artificial
<220> FEATURE:
<223> OTHER INFORMATION: T7 primer

<400> SEQUENCE: 176
taatacgact cactataggg                                           20

<210> SEQ ID NO 177
<211> LENGTH: 21
<212> TYPE: DNA
<213> ORGANISM: Artificial
<220> FEATURE:
<223> OTHER INFORMATION: cp3R primer

<400> SEQUENCE: 177
gccagcattg acaggaggtt g                                         21

<210> SEQ ID NO 178
```

<211> LENGTH: 241
<212> TYPE: PRT
<213> ORGANISM: Artificial
<220> FEATURE:
<223> OTHER INFORMATION: #5 VH1-15-VL1

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Asn Met Asn Trp Val Arg Gln Ala Pro Gly Gln Gly Leu Glu Trp Ile
            35                  40                  45

Gly Asn Ile Asp Pro Tyr Tyr Gly Gly Thr Ser Tyr Asn Gln Lys Phe
        50                  55                  60

Lys Gly Arg Ala Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Tyr Arg Ala Tyr Tyr Phe Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asn Val Arg Thr Ala Val Ala Trp Tyr Gln Gln Lys Pro Gly Lys
                165                 170                 175

Ala Pro Lys Ala Leu Ile Tyr Leu Ala Ser Asn Arg His Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Leu Gln
    210                 215                 220

His Trp Asn Tyr Pro Leu Thr Phe Gly Gly Gly Thr Lys Val Glu Ile
225                 230                 235                 240

Lys

<210> SEQ ID NO 179
<211> LENGTH: 241
<212> TYPE: PRT
<213> ORGANISM: Artificial
<220> FEATURE:
<223> OTHER INFORMATION: #5 VH2-15-VL1

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Asn Met Asn Trp Val Arg Gln Ala Pro Gly Gln Gly Leu Glu Trp Ile
            35                  40                  45

Gly Asn Ile Asp Pro Tyr Tyr Gly Gly Thr Ser Tyr Asn Gln Lys Phe
        50                  55                  60

Lys Gly Arg Val Thr Leu Thr Val Asp Thr Ser Thr Ser Thr Ala Tyr
65                  70                  75                  80

```
Met Glu Leu Arg Ser Leu Arg Ser Asp Asp Thr Ala Val Tyr Tyr Cys
                85                  90                  95

Ala Arg Gly Asp Tyr Arg Ala Tyr Tyr Phe Asp Tyr Trp Gly Gln Gly
            100                 105                 110

Thr Thr Val Thr Val Ser Ser Gly Gly Gly Ser Gly Gly Gly Gly
            115                 120                 125

Ser Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asn Val Arg Thr Ala Val Ala Trp Tyr Gln Gln Lys Pro Gly Lys
                165                 170                 175

Ala Pro Lys Ala Leu Ile Tyr Leu Ala Ser Asn Arg His Thr Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Leu Gln
        210                 215                 220

His Trp Asn Tyr Pro Leu Thr Phe Gly Gly Gly Thr Lys Val Glu Ile
225                 230                 235                 240

Lys

<210> SEQ ID NO 180
<211> LENGTH: 241
<212> TYPE: PRT
<213> ORGANISM: Artificial
<220> FEATURE:
<223> OTHER INFORMATION: #5 VH3-15-VL1

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Asn Met Asn Trp Val Arg Gln Ala Pro Gly Gln Gly Leu Glu Trp Ile
            35                  40                  45

Gly Asn Ile Asp Pro Tyr Tyr Gly Gly Thr Ser Tyr Asn Gln Lys Phe
    50                  55                  60

Lys Gly Arg Val Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Tyr Arg Ala Tyr Tyr Phe Asp Tyr Trp Gly Gln Gly
            100                 105                 110

Thr Thr Val Thr Val Ser Ser Gly Gly Gly Ser Gly Gly Gly Gly
            115                 120                 125

Ser Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asn Val Arg Thr Ala Val Ala Trp Tyr Gln Gln Lys Pro Gly Lys
                165                 170                 175

Ala Pro Lys Ala Leu Ile Tyr Leu Ala Ser Asn Arg His Thr Gly Val
            180                 185                 190
```

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Leu Gln
    210                 215                 220

His Trp Asn Tyr Pro Leu Thr Phe Gly Gly Gly Thr Lys Val Glu Ile
225                 230                 235                 240

Lys

<210> SEQ ID NO 181
<211> LENGTH: 245
<212> TYPE: PRT
<213> ORGANISM: Artificial
<220> FEATURE:
<223> OTHER INFORMATION: #6 VH1-15-VL1

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Arg Ala Met Asp Tyr Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Asp Ile Val Met Thr Gln Ser Pro Leu Ser Leu
    130                 135                 140

Pro Val Thr Pro Gly Glu Pro Ala Ser Ile Ser Cys Arg Ser Ser Gln
145                 150                 155                 160

Ser Leu Val His Ser Asn Gly Asn Thr Tyr Leu His Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Ser Gln Ser Thr His Val Pro Leu Thr Phe Gly Gly Gly Thr
225                 230                 235                 240

Lys Val Glu Ile Lys
            245

<210> SEQ ID NO 182
<211> LENGTH: 245
<212> TYPE: PRT
<213> ORGANISM: Artificial
<220> FEATURE:
<223> OTHER INFORMATION: #6 VH1-15-VL2

<400> SEQUENCE: 182

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Arg Arg Ala Met Asp Tyr Trp Gly Gln Gly Thr
                100                 105                 110

Met Val Thr Val Ser Ser Gly Gly Gly Ser Gly Gly Gly Gly Ser
            115                 120                 125

Gly Gly Gly Gly Ser Asp Ile Val Met Thr Gln Ser Pro Leu Ser Leu
            130                 135                 140

Pro Val Thr Pro Gly Glu Pro Ala Ser Ile Ser Cys Arg Ser Ser Gln
145                 150                 155                 160

Ser Leu Val His Ser Ser Gly Asn Thr Tyr Leu His Trp Tyr Leu Gln
                165                 170                 175

Lys Pro Gly Gln Ser Pro Gln Leu Leu Ile Tyr Lys Val Ser Asn Arg
                180                 185                 190

Phe Ser Gly Val Pro Asp Arg Phe Ser Gly Ser Gly Ser Gly Thr Asp
                195                 200                 205

Phe Thr Leu Lys Ile Ser Arg Val Glu Ala Glu Asp Val Gly Val Tyr
        210                 215                 220

Tyr Cys Ser Gln Ser Thr His Val Pro Leu Thr Phe Gly Gly Gly Thr
225                 230                 235                 240

Lys Val Glu Ile Lys
            245

<210> SEQ ID NO 183
<211> LENGTH: 245
<212> TYPE: PRT
<213> ORGANISM: Artificial
<220> FEATURE:
<223> OTHER INFORMATION: #6 VH2-15-VL1

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Tyr Ile Ser Ser Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Arg Arg Ala Met Asp Tyr Trp Gly Gln Gly Thr
                100                 105                 110
```

Met Val Thr Val Ser Ser Gly Gly Gly Gly Ser
115                 120                 125

Gly Gly Gly Gly Ser Asp Ile Val Met Thr Gln Ser Pro Leu Ser Leu
130                 135                 140

Pro Val Thr Pro Gly Glu Pro Ala Ser Ile Ser Cys Arg Ser Ser Gln
145                 150                 155                 160

Ser Leu Val His Ser Asn Gly Asn Thr Tyr Leu His Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Ser Gln Ser Thr His Val Pro Leu Thr Phe Gly Gly Gly Thr
225                 230                 235                 240

Lys Val Glu Ile Lys
            245

<210> SEQ ID NO 184
<211> LENGTH: 245
<212> TYPE: PRT
<213> ORGANISM: Artificial
<220> FEATURE:
<223> OTHER INFORMATION: #6 VH2-15-VL2

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Tyr Ile Ser Ser Gly Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Arg Arg Ala Met Asp Tyr Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Leu Ser Leu
130                 135                 140

Pro Val Thr Pro Gly Glu Pro Ala Ser Ile Ser Cys Arg Ser Ser Gln
145                 150                 155                 160

Ser Leu Val His Ser Asn Gly Asn Thr Tyr Leu His Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Ser Gln Ser Thr His Val Pro Leu Thr Phe Gly Gly Gly Thr
225                 230                 235                 240

Lys Val Glu Ile Lys
            245

<210> SEQ ID NO 185
<211> LENGTH: 283
<212> TYPE: PRT
<213> ORGANISM: Artificial
<220> FEATURE:
<223> OTHER INFORMATION: hCD8-hCD28-h4-1BB-hCD3

<400> SEQUENCE: 185

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg Ser Lys Arg Ser Arg Leu Leu His Ser Asp Tyr Met
                85                  90                  95

Asn Met Thr Pro Arg Arg Pro Gly Pro Thr Arg Lys His Tyr Gln Pro
            100                 105                 110

Tyr Ala Pro Pro Arg Asp Phe Ala Ala Tyr Arg Ser Arg Phe Ser Val
        115                 120                 125

Val Lys Arg Gly Arg Lys Lys Leu Leu Tyr Ile Phe Lys Gln Pro Phe
    130                 135                 140

Met Arg Pro Val Gln Thr Thr Gln Glu Glu Asp Gly Cys Ser Cys Arg
145                 150                 155                 160

Phe Pro Glu Glu Glu Glu Gly Gly Cys Glu Leu Arg Val Lys Phe Ser
                165                 170                 175

Arg Ser Ala Asp Ala Pro Ala Tyr Gln Gln Gly Gln Asn Gln Leu Tyr
            180                 185                 190

Asn Glu Leu Asn Leu Gly Arg Arg Glu Glu Tyr Asp Val Leu Asp Lys
        195                 200                 205

Arg Arg Gly Arg Asp Pro Glu Met Gly Gly Lys Pro Arg Arg Lys Asn
    210                 215                 220

Pro Gln Glu Gly Leu Tyr Asn Glu Leu Gln Lys Asp Lys Met Ala Glu
225                 230                 235                 240

Ala Tyr Ser Glu Ile Gly Met Lys Gly Glu Arg Arg Arg Gly Lys Gly
                245                 250                 255

His Asp Gly Leu Tyr Gln Gly Leu Ser Thr Ala Thr Lys Asp Thr Tyr
            260                 265                 270

Asp Ala Leu His Met Gln Ala Leu Pro Pro Arg
        275                 280

<210> SEQ ID NO 186
<211> LENGTH: 277
<212> TYPE: PRT
<213> ORGANISM: Artificial
<220> FEATURE:
<223> OTHER INFORMATION: hCD8-hCD28-h4-1BB-hCD3

<400> SEQUENCE: 186

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Arg Ser Lys
65                  70                  75                  80

Arg Ser Arg Leu Leu His Ser Asp Tyr Met Asn Met Thr Pro Arg Arg
                85                  90                  95

Pro Gly Pro Thr Arg Lys His Tyr Gln Pro Tyr Ala Pro Pro Arg Asp
            100                 105                 110

Phe Ala Ala Tyr Arg Ser Arg Phe Ser Val Val Lys Arg Gly Arg Lys
        115                 120                 125

Lys Leu Leu Tyr Ile Phe Lys Gln Pro Phe Met Arg Pro Val Gln Thr
    130                 135                 140

Thr Gln Glu Glu Asp Gly Cys Ser Cys Arg Phe Pro Glu Glu Glu Glu
145                 150                 155                 160

Gly Gly Cys Glu Leu Arg Val Lys Phe Ser Arg Ser Ala Asp Ala Pro
                165                 170                 175

Ala Tyr Gln Gln Gly Gln Asn Gln Leu Tyr Asn Glu Leu Asn Leu Gly
            180                 185                 190

Arg Arg Glu Glu Tyr Asp Val Leu Asp Lys Arg Arg Gly Arg Asp Pro
        195                 200                 205

Glu Met Gly Gly Lys Pro Arg Arg Lys Asn Pro Gln Glu Gly Leu Tyr
    210                 215                 220

Asn Glu Leu Gln Lys Asp Lys Met Ala Glu Ala Tyr Ser Glu Ile Gly
225                 230                 235                 240

Met Lys Gly Glu Arg Arg Arg Gly Lys Gly His Asp Gly Leu Tyr Gln
                245                 250                 255

Gly Leu Ser Thr Ala Thr Lys Asp Thr Tyr Asp Ala Leu His Met Gln
            260                 265                 270

Ala Leu Pro Pro Arg
            275

<210> SEQ ID NO 187
<211> LENGTH: 276
<212> TYPE: PRT
<213> ORGANISM: Artificial
<220> FEATURE:
<223> OTHER INFORMATION: hCD8-hCD28-h4-1BB-hCD3

<400> SEQUENCE: 187

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Arg Ser Lys Arg
65                  70                  75                  80

```
Ser Arg Leu Leu His Ser Asp Tyr Met Asn Met Thr Pro Arg Arg Pro
                85                  90                  95

Gly Pro Thr Arg Lys His Tyr Gln Pro Tyr Ala Pro Pro Arg Asp Phe
            100                 105                 110

Ala Ala Tyr Arg Ser Arg Phe Ser Val Val Lys Arg Gly Arg Lys Lys
            115                 120                 125

Leu Leu Tyr Ile Phe Lys Gln Pro Phe Met Arg Pro Val Gln Thr Thr
        130                 135                 140

Gln Glu Glu Asp Gly Cys Ser Cys Arg Phe Pro Glu Glu Glu Glu Gly
145                 150                 155                 160

Gly Cys Glu Leu Arg Val Lys Phe Ser Arg Ser Ala Asp Ala Pro Ala
                165                 170                 175

Tyr Gln Gln Gly Gln Asn Gln Leu Tyr Asn Glu Leu Asn Leu Gly Arg
            180                 185                 190

Arg Glu Glu Tyr Asp Val Leu Asp Lys Arg Arg Gly Arg Asp Pro Glu
            195                 200                 205

Met Gly Gly Lys Pro Arg Arg Lys Asn Pro Gln Glu Gly Leu Tyr Asn
        210                 215                 220

Glu Leu Gln Lys Asp Lys Met Ala Glu Ala Tyr Ser Glu Ile Gly Met
225                 230                 235                 240

Lys Gly Glu Arg Arg Arg Gly Lys Gly His Asp Gly Leu Tyr Gln Gly
                245                 250                 255

Leu Ser Thr Ala Thr Lys Asp Thr Tyr Asp Ala Leu His Met Gln Ala
            260                 265                 270

Leu Pro Pro Arg
        275

<210> SEQ ID NO 188
<211> LENGTH: 19
<212> TYPE: PRT
<213> ORGANISM: Homo sapiens

<400> SEQUENCE: 188

Met Asp Trp Thr Trp Arg Ile Leu Phe Leu Val Ala Ala Ala Thr Gly
1               5                   10                  15

Ala His Ser
```